US010850092B2

(12) United States Patent
Hastings et al.

(10) Patent No.: US 10,850,092 B2
(45) Date of Patent: *Dec. 1, 2020

(54) LEADLESS CARDIAC STIMULATION SYSTEMS

(71) Applicant: BOSTON SCIENTIFIC SCIMED, INC., Maple Grove, MN (US)

(72) Inventors: Roger Hastings, Naples, FL (US); Anupama Sadasiva, Maple Grove, MN (US); Michael J. Pikus, Golden Valley, MN (US); Graig L. Kveen, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 111 days.

This patent is subject to a terminal disclaimer.

(21) Appl. No.: 16/041,138

(22) Filed: Jul. 20, 2018

(65) Prior Publication Data

US 2018/0326203 A1    Nov. 15, 2018

Related U.S. Application Data

(60) Continuation of application No. 15/380,160, filed on Dec. 15, 2016, now Pat. No. 10,029,092, which is a
(Continued)

(51) Int. Cl.
*A61N 1/05* (2006.01)
*A61N 1/372* (2006.01)
(Continued)

(52) U.S. Cl.
CPC ........... *A61N 1/0587* (2013.01); *A61N 1/057* (2013.01); *A61N 1/059* (2013.01); *A61N 1/0573* (2013.01);
(Continued)

(58) Field of Classification Search
CPC .... A61N 1/0587; A61N 1/059; A61N 1/3756; A61N 1/37288
See application file for complete search history.

(56) References Cited

U.S. PATENT DOCUMENTS 1,076,658 A    10/1913    Bechdoldt
3,057,356 A    10/1962    Greatbatch
(Continued)

FOREIGN PATENT DOCUMENTS

EP    0758542 A1    2/1997
EP    1166820 A2    1/2002
(Continued)

OTHER PUBLICATIONS

U.S. Appl. No. 11/316,120, Response filed Aug. 27, 2010 to Non Final Office Action dated May 27, 2010, 13 pgs.
(Continued)

*Primary Examiner* — Tammie K Marlen
(74) *Attorney, Agent, or Firm* — Seager, Tufte & Wickhem LLP

(57) ABSTRACT

Various configurations of systems that employ leadless electrodes to provide pacing therapy are provided. In one example, a system that provides multiple sites for pacing of myocardium of a heart includes wireless pacing electrode assemblies that are implantable at sites proximate the myocardium using a percutaneous, transluminal, catheter delivery system. Also disclosed are various configurations of such systems, wireless electrode assemblies, and delivery catheters for delivering and implanting the electrode assemblies.

20 Claims, 26 Drawing Sheets

Related U.S. Application Data continuation of application No. 14/223,506, filed on Mar. 24, 2014, now Pat. No. 9,545,513, which is a continuation of application No. 13/717,027, filed on Dec. 17, 2012, now Pat. No. 10,076,658, which is a continuation of application No. 11/745,105, filed on May 7, 2007, now Pat. No. 8,340,780, which is a division of application No. 11/075,376, filed on Mar. 7, 2005, now Pat. No. 7,647,109, which is a continuation-in-part of application No. 10/971,550, filed on Oct. 20, 2004, now Pat. No. 7,532,933.

(51) Int. Cl.
    *A61N 1/375*     (2006.01)
    *A61N 1/378*     (2006.01)
    *A61N 1/362*     (2006.01)

(52) U.S. Cl.
    CPC .......... *A61N 1/362* (2013.01); *A61N 1/3756* (2013.01); *A61N 1/3787* (2013.01); *A61N 1/37205* (2013.01); *A61N 1/37229* (2013.01); *A61N 1/37512* (2017.08)

(56) References Cited

U.S. PATENT DOCUMENTS

| | | |
|---|---|---|
| 3,357,434 A | 12/1967 | Abell |
| 3,596,662 A | 8/1971 | Bolduc |
| 3,667,477 A | 6/1972 | Susset et al. |
| 3,713,449 A | 1/1973 | Mulier |
| 3,727,616 A | 4/1973 | Lenzkes |
| 3,814,104 A | 6/1974 | Irnich |
| 3,835,864 A | 9/1974 | Rasor et al. |
| 3,902,501 A | 9/1975 | Citron |
| 3,942,535 A | 3/1976 | Schulman |
| 3,943,936 A | 3/1976 | Rasor et al. |
| 4,010,756 A | 3/1977 | Dumont et al. |
| 4,157,720 A | 6/1979 | Greatbatch |
| 4,162,679 A | 7/1979 | Reenstierna |
| 4,198,991 A | 4/1980 | Harris |
| 4,256,115 A | 3/1981 | Bilitch |
| 4,441,210 A | 4/1984 | Hochmair et al. |
| 4,524,774 A | 6/1985 | Hildebrandt |
| 4,525,774 A | 6/1985 | Kino et al. |
| 4,641,664 A | 2/1987 | Botvidsson |
| 4,644,957 A | 2/1987 | Ricciardelli et al. |
| 4,681,111 A | 7/1987 | Silvian |
| 4,721,118 A | 1/1988 | Harris |
| 4,830,006 A | 5/1989 | Haluska et al. |
| 4,858,623 A | 8/1989 | Bradshaw et al. |
| 4,860,750 A | 8/1989 | Frey et al. |
| 4,953,564 A | 9/1990 | Berthelsen |
| 4,987,897 A | 1/1991 | Funke |
| 5,012,806 A | 5/1991 | De Bellis |
| 5,078,736 A | 1/1992 | Behl |
| 5,143,090 A | 9/1992 | Dutcher et al. |
| 5,178,149 A | 1/1993 | Imburgia et al. |
| 5,193,539 A | 3/1993 | Schulman et al. |
| 5,193,540 A | 3/1993 | Schulman et al. |
| 5,234,437 A | 8/1993 | Sepetka |
| 5,246,014 A | 9/1993 | Williams et al. |
| 5,250,071 A | 10/1993 | Palermo |
| 5,255,693 A | 10/1993 | Dutcher et al. |
| 5,261,916 A | 11/1993 | Engelson |
| 5,300,107 A | 4/1994 | Stokes et al. |
| 5,304,195 A | 4/1994 | Twyford, Jr. et al. |
| 5,312,415 A | 5/1994 | Palermo |
| 5,312,439 A | 5/1994 | Loeb |
| 5,324,316 A | 6/1994 | Schulman et al. |
| 5,324,325 A | 6/1994 | Moaddeb |
| 5,342,408 A | 8/1994 | Decoriolis et al. |
| 5,350,397 A | 9/1994 | Palermo et al. |
| 5,383,915 A | 1/1995 | Adams |
| 5,383,924 A | 1/1995 | Brehier |
| 5,405,367 A | 4/1995 | Schulman et al. |
| 5,411,535 A | 5/1995 | Fujii et al. |
| 5,411,537 A | 5/1995 | Munshi et al. |
| 5,447,533 A | 9/1995 | Vachon et al. |
| 5,487,760 A | 1/1996 | Villafana |
| 5,531,780 A | 7/1996 | Vachon |
| 5,571,148 A | 11/1996 | Loeb et al. |
| 5,622,168 A | 4/1997 | Keusch et al. |
| 5,735,887 A | 4/1998 | Barreras, Sr. et al. |
| 5,755,764 A | 5/1998 | Schroeppel |
| 5,775,331 A | 7/1998 | Raymond et al. |
| 5,779,715 A | 7/1998 | Tu |
| 5,800,535 A | 9/1998 | Howard, III |
| 5,814,089 A | 9/1998 | Stokes et al. |
| 5,833,715 A | 11/1998 | Vachon et al. |
| 5,851,227 A | 12/1998 | Spehr |
| 5,871,532 A | 2/1999 | Schroeppel |
| 5,876,431 A | 3/1999 | Spehr et al. |
| 6,035,239 A | 3/2000 | Patag et al. |
| 6,053,873 A | 4/2000 | Govari et al. |
| 6,115,636 A | 9/2000 | Ryan |
| 6,141,588 A | 10/2000 | Cox et al. |
| 6,141,591 A | 10/2000 | Weber et al. |
| 6,144,880 A | 11/2000 | Ding et al. |
| 6,161,029 A | 12/2000 | Spreigl et al. |
| 6,164,284 A | 12/2000 | Schulman et al. |
| 6,200,303 B1 | 3/2001 | Verrior et al. |
| 6,208,894 B1 | 3/2001 | Schulman et al. |
| 6,223,079 B1 | 4/2001 | Bakels et al. |
| 6,240,316 B1 | 5/2001 | Richmond et al. |
| 6,266,567 B1 | 7/2001 | Ishikawa et al. |
| 6,315,721 B2 | 11/2001 | Schulman et al. |
| 6,317,615 B1 | 11/2001 | KenKnight et al. |
| 6,322,559 B1 | 11/2001 | Daulton et al. |
| 6,345,202 B2 | 2/2002 | Richmond et al. |
| 6,351,673 B1 | 2/2002 | Ding et al. |
| 6,360,127 B1 | 3/2002 | Ding et al. |
| 6,363,938 B2 | 4/2002 | Saadat et al. |
| 6,370,434 B1 | 4/2002 | Zhang et al. |
| 6,381,495 B1 | 4/2002 | Jenkins |
| 6,385,472 B1 | 5/2002 | Hall et al. |
| 6,409,674 B1 | 6/2002 | Brockway et al. |
| 6,442,413 B1 | 8/2002 | Silver |
| 6,445,953 B1 | 9/2002 | Bulkes et al. |
| 6,456,256 B1 | 9/2002 | Amundson et al. |
| 6,501,983 B1 | 12/2002 | Natarajan et al. |
| 6,510,345 B1 | 1/2003 | Van Bentem |
| 6,522,926 B1 | 2/2003 | Kieval et al. |
| 6,542,775 B2 | 4/2003 | Ding et al. |
| 6,556,874 B2 | 4/2003 | Audoglio |
| 6,564,807 B1 | 5/2003 | Schulman et al. |
| 6,571,127 B1 | 5/2003 | Ben-Haim et al. |
| 6,574,510 B2 | 6/2003 | Von Arx et al. |
| 6,582,441 B1 | 6/2003 | He et al. |
| 6,589,230 B2 | 7/2003 | Gia et al. |
| 6,614,406 B2 | 9/2003 | Amundson et al. |
| 6,647,291 B1 | 11/2003 | Bonner et al. |
| 6,647,292 B1 | 11/2003 | Bardy et al. |
| 6,783,499 B2 | 8/2004 | Schwartz |
| 6,856,836 B2 | 2/2005 | Ding et al. |
| 6,859,665 B2 | 2/2005 | Ding et al. |
| 6,895,265 B2 | 5/2005 | Silver |
| 6,895,280 B2 | 5/2005 | Meadows et al. |
| 6,901,294 B1 | 5/2005 | Whitehurst et al. |
| 6,907,285 B2 | 6/2005 | Denker et al. |
| 6,917,833 B2 | 7/2005 | Denker et al. |
| 6,947,792 B2 | 9/2005 | Ben-Haim et al. |
| 6,970,742 B2 | 11/2005 | Mann et al. |
| 6,978,173 B2 | 12/2005 | Stoll et al. |
| 7,003,350 B2 | 2/2006 | Denker et al. |
| 7,006,864 B2 | 2/2006 | Echt et al. |
| 7,050,849 B2 | 5/2006 | Echt et al. |
| 7,076,305 B2 | 7/2006 | Imran et al. |
| 7,103,408 B2 | 9/2006 | Haller et al. |
| 7,120,992 B2 | 10/2006 | He et al. |
| 7,132,173 B2 | 11/2006 | Daulton |
| 7,177,698 B2 | 2/2007 | Klosterman et al. |
| 7,184,830 B2 | 2/2007 | Echt et al. |
| 7,209,783 B2 | 4/2007 | Fellows et al. |

(56) References Cited

U.S. PATENT DOCUMENTS

| | | |
|---|---|---|
| 7,231,260 B2 | 6/2007 | Wallace et al. |
| 7,410,497 B2 | 8/2008 | Hastings et al. |
| 7,418,298 B2 * | 8/2008 | Shiroff ............... A61B 17/0469 607/126 |
| 7,428,438 B2 | 9/2008 | Parramon et al. |
| 7,437,193 B2 | 10/2008 | Parramon et al. |
| 7,522,962 B1 | 4/2009 | Doron et al. |
| 7,532,932 B2 | 5/2009 | Denker et al. |
| 7,532,933 B2 | 5/2009 | Hastings et al. |
| 7,558,631 B2 | 7/2009 | Cowan et al. |
| 7,606,621 B2 | 10/2009 | Brisken et al. |
| 7,610,092 B2 | 10/2009 | Cowan et al. |
| 7,615,010 B1 | 11/2009 | Najafi et al. |
| 7,647,109 B2 | 1/2010 | Hastings et al. |
| 7,650,186 B2 | 1/2010 | Hastings et al. |
| 7,702,392 B2 | 4/2010 | Echt et al. |
| 7,765,001 B2 | 7/2010 | Echt et al. |
| 7,809,438 B2 | 10/2010 | Echt et al. |
| 7,822,480 B2 | 10/2010 | Park et al. |
| 7,840,281 B2 | 11/2010 | Kveen et al. |
| 7,848,815 B2 | 12/2010 | Brisken et al. |
| 7,848,823 B2 | 12/2010 | Drasler et al. |
| 7,890,173 B2 | 2/2011 | Brisken et al. |
| 7,894,904 B2 | 2/2011 | Cowan et al. |
| 7,894,907 B2 | 2/2011 | Cowan et al. |
| 7,894,910 B2 | 2/2011 | Cowan et al. |
| 7,899,541 B2 | 3/2011 | Cowan et al. |
| 7,899,542 B2 | 3/2011 | Cowan et al. |
| 7,937,161 B2 | 5/2011 | Hastings et al. |
| 7,996,087 B2 | 8/2011 | Cowan et al. |
| 8,050,774 B2 | 11/2011 | Kveen et al. |
| 8,185,213 B2 | 5/2012 | Kveen et al. |
| 8,204,605 B2 | 6/2012 | Hastings et al. |
| 8,340,780 B2 | 12/2012 | Hastings et al. |
| 8,386,048 B2 | 2/2013 | McClure et al. |
| 9,545,513 B2 | 1/2017 | Hastings et al. |
| 10,029,092 B2 | 7/2018 | Hastings et al. |
| 2001/0018547 A1 | 8/2001 | Mechlenburg et al. |
| 2002/0018379 A1 | 2/2002 | Hakuchoh et al. |
| 2002/0026228 A1 | 2/2002 | Schauerte |
| 2002/0052632 A1 | 5/2002 | Ben-Haim et al. |
| 2002/0065543 A1 | 5/2002 | Gomperz et al. |
| 2002/0077556 A1 | 6/2002 | Schwartz |
| 2002/0077685 A1 | 6/2002 | Sundquist et al. |
| 2002/0103424 A1 | 8/2002 | Swoyer et al. |
| 2002/0123774 A1 | 9/2002 | Loeb et al. |
| 2002/0123785 A1 | 9/2002 | Zhang et al. |
| 2002/0128546 A1 | 9/2002 | Silver |
| 2002/0138009 A1 | 9/2002 | Brockway et al. |
| 2002/0138100 A1 | 9/2002 | Stoll et al. |
| 2002/0183791 A1 | 12/2002 | Denker et al. |
| 2002/0188323 A1 | 12/2002 | Penner et al. |
| 2002/0198604 A1 | 12/2002 | Schulman et al. |
| 2003/0036773 A1 | 2/2003 | Whitehurst et al. |
| 2003/0050681 A1 | 3/2003 | Pianca et al. |
| 2003/0055465 A1 | 3/2003 | Ben-Haim et al. |
| 2003/0055466 A1 | 3/2003 | Ben-Haim et al. |
| 2003/0055467 A1 | 3/2003 | Ben-Haim et al. |
| 2003/0074041 A1 | 4/2003 | Parry et al. |
| 2003/0088278 A1 | 5/2003 | Bardy et al. |
| 2003/0109914 A1 | 6/2003 | Westlund et al. |
| 2003/0114735 A1 | 6/2003 | Silver et al. |
| 2003/0114742 A1 | 6/2003 | Lewkowicz et al. |
| 2003/0158584 A1 | 8/2003 | Cates et al. |
| 2003/0181958 A1 | 9/2003 | Dobak, III |
| 2003/0181959 A1 | 9/2003 | Dobak, III |
| 2003/0204206 A1 | 10/2003 | Padua et al. |
| 2003/0216729 A1 | 11/2003 | Marchitto et al. |
| 2003/0236518 A1 | 12/2003 | Marchitto et al. |
| 2004/0019364 A1 | 1/2004 | Kieval et al. |
| 2004/0059280 A1 | 3/2004 | Makower et al. |
| 2004/0059392 A1 | 3/2004 | Parramon et al. |
| 2004/0073267 A1 | 4/2004 | Holzer |
| 2004/0087831 A1 | 5/2004 | Michels et al. |
| 2004/0097805 A1 | 5/2004 | Verard et al. |
| 2004/0098068 A1 | 5/2004 | Carbunaru et al. |
| 2004/0102830 A1 | 5/2004 | Williams |
| 2004/0103906 A1 | 6/2004 | Schulman et al. |
| 2004/0106954 A1 | 6/2004 | Whitehurst et al. |
| 2004/0127895 A1 | 7/2004 | Flock et al. |
| 2004/0147969 A1 | 7/2004 | Mann et al. |
| 2004/0147973 A1 | 7/2004 | Hauser |
| 2004/0167580 A1 | 8/2004 | Mann et al. |
| 2004/0171355 A1 | 9/2004 | Yu et al. |
| 2004/0172083 A1 | 9/2004 | Penner |
| 2004/0176672 A1 | 9/2004 | Silver et al. |
| 2004/0176822 A1 | 9/2004 | Thompson et al. |
| 2004/0193092 A1 | 9/2004 | Deal |
| 2004/0193229 A1 | 9/2004 | Starkebaum et al. |
| 2004/0210282 A1 | 10/2004 | Flock et al. |
| 2004/0215092 A1 | 10/2004 | Fischell et al. |
| 2004/0230090 A1 | 11/2004 | Hegde et al. |
| 2004/0230255 A1 | 11/2004 | Dobak, III |
| 2004/0230281 A1 | 11/2004 | Heil et al. |
| 2005/0021108 A1 | 1/2005 | Klosterman et al. |
| 2005/0025797 A1 | 2/2005 | Wang et al. |
| 2005/0043765 A1 | 2/2005 | Williams et al. |
| 2005/0057905 A1 | 3/2005 | He et al. |
| 2005/0065575 A1 | 3/2005 | Dobak |
| 2005/0080346 A1 | 4/2005 | Gianchandani et al. |
| 2005/0080459 A1 | 4/2005 | Jacobson et al. |
| 2005/0096702 A1 | 5/2005 | Denker et al. |
| 2005/0131511 A1 | 6/2005 | Westlund |
| 2005/0136385 A1 | 6/2005 | Mann et al. |
| 2005/0165456 A1 | 7/2005 | Mann et al. |
| 2005/0182456 A1 | 8/2005 | Ziobro et al. |
| 2005/0182465 A1 | 8/2005 | Ness |
| 2005/0251238 A1 | 11/2005 | Wallace et al. |
| 2005/0251240 A1 | 11/2005 | Doan |
| 2005/0256549 A1 | 11/2005 | Holzer |
| 2005/0261741 A1 | 11/2005 | Libbus et al. |
| 2005/0273014 A1 | 12/2005 | Gianchandani et al. |
| 2005/0288727 A1 | 12/2005 | Penner |
| 2006/0015097 A1 | 1/2006 | Mulier et al. |
| 2006/0020316 A1 | 1/2006 | Martinez et al. |
| 2006/0084965 A1 | 4/2006 | Young |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095089 A1 | 5/2006 | Soykan et al. |
| 2006/0136001 A1 | 6/2006 | Ortega et al. |
| 2006/0136004 A1 | 6/2006 | Cowan et al. |
| 2006/0173504 A1 | 8/2006 | Zhu et al. |
| 2006/0173505 A1 | 8/2006 | Salo et al. |
| 2006/0178719 A1 | 8/2006 | Ideker et al. |
| 2006/0206170 A1 | 9/2006 | Denker et al. |
| 2007/0075905 A1 | 4/2007 | Denker et al. |
| 2007/0106357 A1 | 5/2007 | Denker et al. |
| 2007/0135882 A1 | 6/2007 | Drasler et al. |
| 2007/0135883 A1 | 6/2007 | Drasler et al. |
| 2007/0150009 A1 | 6/2007 | Kveen et al. |
| 2007/0150037 A1 | 6/2007 | Hastings et al. |
| 2007/0150038 A1 | 6/2007 | Hastings et al. |
| 2007/0203556 A1 | 8/2007 | Rutten et al. |
| 2007/0219590 A1 | 9/2007 | Hastings et al. |
| 2007/0239248 A1 | 10/2007 | Hastings et al. |
| 2008/0021505 A1 | 1/2008 | Hastings et al. |
| 2008/0021532 A1 | 1/2008 | Kveen et al. |
| 2008/0039904 A1 | 2/2008 | Bulkes et al. |
| 2008/0046040 A1 | 2/2008 | Denker et al. |
| 2008/0077184 A1 | 3/2008 | Denker et al. |
| 2008/0077188 A1 | 3/2008 | Denker et al. |
| 2008/0109054 A1 | 5/2008 | Hastings et al. |
| 2008/0119911 A1 | 5/2008 | Rosero |
| 2008/0319502 A1 | 12/2008 | Sunagawa et al. |
| 2009/0018599 A1 | 1/2009 | Hastings et al. |
| 2010/0100144 A1 | 4/2010 | Shuros et al. |
| 2010/0314775 A1 | 12/2010 | Schwarzbauer |
| 2011/0034939 A1 | 2/2011 | Kveen et al. |

(56) References Cited

U.S. PATENT DOCUMENTS

| | | |
|---|---|---|
| 2011/0213233 A1 | 9/2011 | Stevenson et al. |
| 2013/0268042 A1 | 10/2013 | Hastings et al. |

FOREIGN PATENT DOCUMENTS

| | | |
|---|---|---|
| EP | 1166832 A1 | 1/2002 |
| EP | 1264572 A1 | 12/2002 |
| EP | 1809372 A2 | 7/2007 |
| EP | 1812104 A1 | 8/2007 |
| EP | 1835962 A1 | 9/2007 |
| FR | 2559391 A1 | 8/1985 |
| JP | 61203730 A | 9/1986 |
| JP | 62254770 A | 11/1987 |
| JP | 02307481 A | 12/1990 |
| JP | 05076501 A | 3/1993 |
| JP | 05245215 A | 9/1993 |
| JP | 06510459 A | 11/1994 |
| JP | 716299 A | 1/1995 |
| JP | 09508054 A | 8/1997 |
| JP | 10509901 A | 9/1998 |
| JP | 2000502931 A | 3/2000 |
| JP | 2001511406 A | 8/2001 |
| JP | 2002510222 A | 4/2002 |
| JP | 2002514478 A | 5/2002 |
| JP | 2004173790 A | 6/2004 |
| JP | 2010509901 A | 3/2010 |
| NZ | 526115 A | 10/2006 |
| NZ | 539770 A | 10/2007 |
| NZ | 539771 A | 10/2007 |
| WO | 9116864 A1 | 11/1991 |
| WO | 9510226 A1 | 4/1995 |
| WO | 9620754 A1 | 7/1996 |
| WO | 9639932 A1 | 12/1996 |
| WO | 9725098 A1 | 7/1997 |
| WO | 9826840 A1 | 6/1998 |
| WO | 9829030 A1 | 7/1998 |
| WO | 9903533 A1 | 1/1999 |
| WO | 9906102 A1 | 2/1999 |
| WO | 9958191 A1 | 11/1999 |
| WO | 9964104 A1 | 12/1999 |
| WO | 0030534 A1 | 6/2000 |
| WO | 0100114 A1 | 1/2001 |
| WO | 0187137 A2 | 11/2001 |
| WO | 03041793 A2 | 5/2003 |
| WO | 03053491 A2 | 7/2003 |
| WO | 03076010 A1 | 9/2003 |
| WO | 03082403 A2 | 10/2003 |
| WO | 03096918 A1 | 11/2003 |
| WO | 03099102 A2 | 12/2003 |
| WO | 2004002572 A1 | 1/2004 |
| WO | 2004012811 A1 | 2/2004 |
| WO | 2004032788 A2 | 4/2004 |
| WO | 2004078025 A2 | 9/2004 |
| WO | 2005058143 A2 | 6/2005 |
| WO | 2005096954 A2 | 10/2005 |
| WO | 2005101660 A1 | 10/2005 |
| WO | 2005107852 A1 | 11/2005 |
| WO | 2005107863 A2 | 11/2005 |
| WO | 2005117737 A2 | 12/2005 |
| WO | 2006045073 A1 | 4/2006 |
| WO | 2006045074 A2 | 4/2006 |
| WO | 2006045075 A1 | 4/2006 |
| WO | 2006096685 A1 | 9/2006 |
| WO | 2007067231 A1 | 6/2007 |
| WO | 2007067253 A1 | 6/2007 |
| WO | 2007078770 A2 | 7/2007 |
| WO | 2007115044 A2 | 10/2007 |
| WO | 2008011626 A1 | 1/2008 |
| WO | 2008034005 A2 | 3/2008 |
| WO | 2008111998 A1 | 9/2008 |

OTHER PUBLICATIONS

U.S. Appl. No. 11/316,120, Response filed Mar. 25, 2011 to Final Office Action dated Oct. 28, 2011, 8 pgs.

U.S. Appl. No. 11/316,120, Response filed May 14, 2008 to Non Final Office Action dated Apr. 11, 2008, 12 pgs.

U.S. Appl. No. 11/316,120, Supplemental Notice of Allowance dated Sep. 1, 2011, 4 pgs.

U.S. Appl. No. 11/394,601, Decision on Pre-Appeal Brief Request dated Oct. 6, 2010, 2 pgs.

U.S. Appl. No. 11/394,601, Final Office Action dated Mar. 22, 2010, 7 pgs.

U.S. Appl. No. 11/394,601, Non-Final Office Action dated Sep. 2, 2009, 6 pgs.

U.S. Appl. No. 11/394,601, Notice of Allowance dated Dec. 28, 2010, 8 pgs.

U.S. Appl. No. 11/394,601, Pre-Appeal Brief Request filed Jul. 21, 2010, 5 pgs.

U.S. Appl. No. 11/394,601, Response filed Dec. 2, 2009 to Non Final Office Action dated Sep. 2, 2009, 11 pgs.

U.S. Appl. No. 11/394,601, Response filed May 4, 2009 to Restriction Requirement dated Apr. 2, 2009, 9 pgs.

U.S. Appl. No. 11/394,601, Restriction Requirement dated Apr. 2, 2009, 10 pgs.

U.S. Appl. No. 11/490,576 Non Final Office Action dated Jul. 9, 2008, 15 pgs.

U.S. Appl. No. 11/490,576 Non-Final Office Action dated Feb. 17, 2009, 8 pgs.

U.S. Appl. No. 11/490,576 Notice of Allowance dated Jun. 4, 2012, 8 pgs.

U.S. Appl. No. 11/490,576 Response filed Nov. 10, 2008 to Non-Final Office Action dated Jul. 9, 2008, 20 pgs.

U.S. Appl. No. 11/490,576, Decision on Pre-Appeal Brief Request dated Aug. 30, 2011, 2 pgs.

U.S. Appl. No. 11/490,576, Final Office Action dated Jan. 19, 2011, 12 pgs.

U.S. Appl. No. 11/490,576, Non Final Office Action dated Nov. 9, 2011, 8 pgs.

U.S. Appl. No. 11/490,576, Non-Final Office Action dated Jul. 12, 2010, 8 pgs.

U.S. Appl. No. 11/490,576, Pre-Appeal Brief Request filed May 12, 2011, 5 pgs.

U.S. Appl. No. 11/490,576, Response filed Apr. 9, 2012 to Non Final Office Action dated Nov. 9, 2011, 11 pgs.

U.S. Appl. No. 11/490,576, Response filed Mar. 5, 2010 to Non Final Office Action dated Oct. 5, 2009, 13 pgs.

U.S. Appl. No. 11/490,576, Response filed Oct. 4, 2010 to Non Final Office Action dated Jul. 12, 2010, 15 pgs.

U.S. Appl. No. 11/490,916 Restriction Requirement dated Dec. 11, 2008, 8 pgs.

U.S. Appl. No. 11/490,916, Examiner Interview Summary dated Apr. 12, 2010, 3 pgs.

U.S. Appl. No. 11/490,916, Examiner Interview Summary dated Aug. 19, 2009, 2 pgs.

U.S. Appl. No. 11/490,916, Final Office Action dated Dec. 17, 2009, 11 pgs.

U.S. Appl. No. 11/490,916, Non Final Office Action dated May 5, 2009, 10 pgs.

U.S. Appl. No. 11/490,916, Notice of Allowance dated Jul. 9, 2010, 4 pgs.

U.S. Appl. No. 11/490,916, Response filed Apr. 15, 2010 to Final Office Action dated Dec. 17, 2009, 12 pgs.

U.S. Appl. No. 11/490,916, Response filed Jan. 12, 2009 to Restriction Requirement dated Dec. 11, 2008, 7 pgs.

U.S. Appl. No. 11/490,916, Supplemental Notice of Allowability dated Oct. 14, 2010, 2 pgs.

U.S. Appl. No. 11/511,152 Response filed Mar. 23, 2009 to Non Final Office Action dated Dec. 23, 2008, 11 pgs.

U.S. Appl. No. 11/511,152, Non-Final Office Action dated Dec. 30, 2009, 13 pgs.

U.S. Appl. No. 11/511,152, Notice of Allowance dated Jul. 28, 2010, 6 pgs.

U.S. Appl. No. 11/511,152, Preliminary Amendment filed Oct. 17, 2006, 3 pgs.

U.S. Appl. No. 11/511,152, Response filed Jun. 30, 2010 to Non-Final Office Action dated Dec. 30, 2009, 12 pgs.

(56) References Cited

OTHER PUBLICATIONS

U.S. Appl. No. 11/511,152, Response filed Nov. 12, 2009 to Final Office Action dated Aug. 10, 2009, 13 pgs.
U.S. Appl. No. 11/549,352, Appeal Brief filed Sep. 9, 2009, 36 Pgs.
U.S. Appl. No. 11/549,352, Appeal Decision dated Jul. 17, 2012, 9 pgs.
U.S. Appl. No. 11/549,352, Examiner Interview Summary dated Jun. 25, 2008, 2 pgs.
U.S. Appl. No. 11/549,352, Examiner's Answer dated Nov. 27, 2009 to Appeal Brief filed Sep. 9, 2009, 12 pgs.
U.S. Appl. No. 11/549,352, Final Office Action dated Aug. 26, 2008, 13 pgs.
U.S. Appl. No. 11/549,352, Final Office Action dated Mar. 9, 2009, 10 pgs.
U.S. Appl. No. 11/549,352, Non-Final Office Action dated Feb. 5, 2008, 11 pgs.
U.S. Appl. No. 11/549,352, Notice of Panel Decision from Pre-Appeal Brief Review dated Feb. 2, 2009, 2 pgs.
U.S. Appl. No. 11/549,352, Pre-Appeal Brief for Review filed Dec. 20, 2008, 5 pgs.
U.S. Appl. No. 11/549,352, Reply Brief filed Jan. 27, 2010, 8 pgs.
U.S. Appl. No. 11/549,352, Response filed Jul. 7, 2008 to Non-Final Office Action dated Feb. 5, 2008, 17 pgs.
U.S. Appl. No. 11/683,577, Examiner Interview Summary dated Jul. 7, 2009, 4 pgs.
U.S. Appl. No. 11/683,577, Final Office Action dated Nov. 9, 2009, 14 pgs.
U.S. Appl. No. 11/683,577, Non-Final Office Action dated Mar. 5, 2009, 13 pgs.
U.S. Appl. No. 11/683,577, Response filed Aug. 5, 2009 to Non Final Office Action dated Mar. 5, 2009, 10 pgs.
U.S. Appl. No. 11/683,577, Response filed May 7, 2010 to Final Office Action dated Nov. 9, 2009, 14 pgs.
U.S. Appl. No. 11/683,584, Examiner Interview Summary dated Jul. 7, 2009, 4 pgs.
U.S. Appl. No. 11/683,584, Final Office Action dated Jan. 29, 2010, 9 pgs.
U.S. Appl. No. 11/683,584, Non-Final Office Action dated Apr. 1, 2009, 9 pgs.
U.S. Appl. No. 11/683,584, Preliminary Amendment filed Mar. 8, 2007, 1 pg.
U.S. Appl. No. 11/683,584, Response filed Jul. 1, 2009 to Non Final Office Action dated Apr. 1, 2009, 7 pgs.
U.S. Appl. No. 11/683,584, Response filed Jul. 21, 2010 to Final Office Action dated Jan. 29, 2010, 12 pgs.
U.S. Appl. No. 11/745,070, Final Office Action dated Dec. 11, 2009, 18 pgs.
U.S. Appl. No. 11/745,070, Non Final Office Action dated Apr. 27, 2009, 11 pgs.
U.S. Appl. No. 11/745,070, Response filed Jul. 27, 2009 to Non Final Office Action dated Apr. 27, 2009, 11 pgs.
U.S. Appl. No. 11/745,105, Final Office Action dated Mar. 30, 2010, 9 pgs.
U.S. Appl. No. 11/745,105, Non Final Office Action dated Feb. 7, 2012, 12 pgs.
U.S. Appl. No. 11/745,105, Non Final Office Action dated May 11, 2011, 13 pgs.
U.S. Appl. No. 11/745,105, Non-Final Office Action dated Sep. 18, 2009, 9 pgs.
U.S. Appl. No. 11/745,105, Notice of Allowance dated Aug. 20, 2012, 5 pgs.
U.S. Appl. No. 11/745,105, Notice of Allowance dated Oct. 31, 2011, 5 pgs.
U.S. Appl. No. 11/745,105, Response filed Aug. 6, 2012 to Non Final Office Action dated Feb. 7, 2012, 11 pgs.
U.S. Appl. No. 11/745,105, Response filed Jan. 19, 2010 to Non Final Office Action dated Sep. 18, 2009, 12 pgs.
U.S. Appl. No. 11/745,105, Response filed Jul. 29, 2010 to Final Office Action dated Mar. 30, 2010, 12 pgs.
U.S. Appl. No. 11/745,105, Response filed Jun. 22, 2009 to Restriction Requirement dated May 21, 2009, 6 pgs.
U.S. Appl. No. 11/745,105, Response filed Sep. 12, 2011 to Non-Final OfiSce Action dated May 11, 2011, 13 pgs.
U.S. Appl. No. 11/745,105, Restriction Requirement dated May 21, 2009, 6 pgs.
U.S. Appl. No. 12/361,884, Final Office Action dated Jul. 3, 2012, 17 pgs.
U.S. Appl. No. 12/361,884, Non Final Office Action dated Oct. 12, 2011, 15 pgs.
U.S. Appl. No. 12/361,884, Preliminary Amendment filed Jun. 30, 2011, 12 pgs.
U.S. Appl. No. 12/361,884, Response filed Apr. 12, 2012 to Non Final Office Action dated Oct. 12, 2011, 21 pgs.
U.S. Appl. No. 12/361,884, Supplemental Preliminary Amendment filed Jul. 27, 2011, 12 pgs.
U.S. Appl. No. 12/365,428, Non Final Office Action dated Aug. 31, 2011, 9 pgs.
U.S. Appl. No. 12/365,428, Notice of Allowance dated Feb. 22, 2012, 7 pgs.
U.S. Appl. No. 12/365,428, Response filed Jan. 30, 2012 to Non Final Office Action dated Aug. 31, 2011, 15 pgs.
U.S. Appl. No. 12/910,106, Non Final Office Action dated Apr. 4, 2011, 9 pgs.
U.S. Appl. No. 12/910,106, Notice of Allowance dated Jan. 26, 2012, 6 pgs.
U.S. Appl. No. 12/910,106, Notice of Allowance dated Oct. 27, 2011, 5 pgs.
U.S. Appl. No. 12/910,106, Response filed Aug. 2, 2011 to Non-Final Office Action dated Apr. 4, 2011, 14 pgs.
U.S. Appl. No. 13/717,027 Preliminary Amendment filed Jun. 25, 2013, 6 pgs.
U.S. Appl. No. 11/075,375,Non-Final Office Action dated Aug. 11, 2008, 15 pgs.
Wagner "Electrodes, Leads, and Biocompatibility", Chapter 6Design of Cardiac Pacemakers, edited by John G Webster., ??. 133-160, 1993.
PCT Application No. PCT/US2007/074135, Written Opinion dated Nov. 6, 2007, 8 pgs.
Piella, "Energy management, wireless and system solutions for highly integrated implantable devices", Doctoral Thesis by Jordi Parramon I Piella for the Universitat Autonoma de Barcelona, certified Dec. 2001, 62 pgs, 2001.
Si et al., "A Frequency Control Method for Regulating Wireless Power to Implantable Devices", IEEE Transactions on Biomedical Circuits and Systems, vol. 2(1), Mar. 22-29, 2008.
Swain "Breakthrough Products Could Put Lesser-Known Firms on the map", MDDI, 6 pgs, Apr. 2004.
U.S. Appl. No. 10/971,550 Response filed Feb. 22, 2007 to Restriction Requirement dated Jan. 22, 2007, 1 pg.
U.S. Appl. No. 10/971,550 Notice of Allowance dated Dec. 22, 2008, 4 pgs.
U.S. Appl. No. 10/971,550 Notice of Allowance dated Jul. 14, 2008, 4 pgs.
U.S. Appl. No. 10/971,550 Restriction Requirement dated Jan. 22, 2007, 22 pgs.
U.S. Appl. No. 10/971,550, 312 Amendment filed Mar. 20, 2009, 6 pgs.
U.S. Appl. No. 10/971,550, ??? Response to 312 Amendment dated Apr. 6, 2009, 2 pgs.
U.S. Appl. No. 10/971,550, Amendment Under 37 C.F.R. Sec. 1.312 filed Mar. 20, 2009, 6 pgs.
U.S. Appl. No. 10/971,550, Examiner Interview Summary dated Jan. 22, 2008, 4 pgs.
U.S. Appl. No. 10/971,550, Non Final Office Action dated Mar. 19, 2007, 11 pgs.
U.S. Appl. No. 10/971,550, Non-Final Office Action dated Nov. 5, 2007, 19 pgs.
U.S. Appl. No. 10/971,550, Response filed Mar. 25, 2008 to Non Final Office Action dated Nov. 5, 2007, 17 pgs.
U.S. Appl. No. 10/971,550, Response filed Sep. 4, 2007 to Non-Final Office Action dated Mar. 19, 2007, 15 pgs.

(56) References Cited

OTHER PUBLICATIONS

U.S. Appl. No. 11/075,375 Response and Preliminary Amendment filed May 7, 2007 to Restriction Requirement dated Apr. 10, 2007, 8 pgs.
U.S. Appl. No. 11/075,375 Restriction Requirement dated Apr. 10, 2007, 6 pgs.
U.S. Appl. No. 11/075,375, Amendment and Response filed Jan. 12, 2009 to Non-Final Office Action dated Aug. 11, 2008, 18 pgs.
U.S. Appl. No. 11/075,375, Examiner Interview Summary dated Jan. 12, 2009, 4 pgs.
U.S. Appl. No. 11/075,375, Examiner Interview Summary dated May 1, 2008, 4 pgs.
U.S. Appl. No. 11/075,375, Final Office Action dated Apr. 16, 2009, 10 pgs.
U.S. Appl. No. 11/075,375, Final Office Action dated Jan. 23, 2008, 10 pgs.
U.S. Appl. No. 11/075,375, Non-Final Office Action dated Jun. 8, 2007, 11 pgs.
U.S. Appl. No. 11/075,375, Notice of Allowance dated Sep. 4, 2009, 6 pgs.
U.S. Appl. No. 11/075,375, Response filed Jul. 16, 2009 to Final Office Action dated Apr. 16, 2009, 13 pgs.
U.S. Appl. No. 11/075,375, Response filed May 22, 2008 to Final Office Action dated Jan. 23, 2008, 16 pgs.
U.S. Appl. No. 11/075,375, Response filed Oct. 26, 2007 to Non-Final Office Action dated Jun. 8, 2007, 10 pgs.
U.S. Appl. No. 11/075,376, Examiner Interview Summary dated Apr. 2, 2008, 4 pgs.
U.S. Appl. No. 11/075,376, Examiner Interview Summary dated Jan. 12, 2009, 4 pgs.
U.S. Appl. No. 11/075,376, Final Office Action dated Apr. 8, 2009, 17 pgs.
U.S. Appl. No. 11/075,376, Final Office Action dated Jan. 7, 2008, 11 pgs.
U.S. Appl. No. 11/075,376, Non-Final Office Action dated Aug. 20, 2008, 16 pgs.
U.S. Appl. No. 11/075,376, Non-Final Office Action dated Jun. 26, 2007, 9 pgs.
U.S. Appl. No. 11/075,376, Notice of Allowance dated Aug. 24, 2009, 6 pgs.
U.S. Appl. No. 11/075,376, Response filed Jan. 21, 2009 to Non-Final Office Action dated Aug. 20, 2008, 22 pgs.
U.S. Appl. No. 11/075,376, Response filed Jul. 8, 2009 to Final Office Action dated Apr. 8, 2009, 11 pgs.
U.S. Appl. No. 11/075,376, Response filed Jun. 9, 2008 to Final Office Action dated Jan. 7, 2008, 20 pgs.
U.S. Appl. No. 11/075,376, Response filed May 7, 2007 to Restriction Requirement dated Apr. 10, 2007, 10 pgs.
U.S. Appl. No. 11/075,376, Response filed Oct. 26, 2007 to Non-Final Office Action dated Jun. 26, 2007, 14 pgs.
U.S. Appl. No. 11/075,376, Restriction Requirement dated Apr. 10, 2007, 6 pgs.
U.S. Appl. No. 11/316,120 Final Office Action dated Aug. 20, 2008, 8 pgs.
U.S. Appl. No. 11/316,120 Response filed Dec. 22, 2008 to Final Office Action dated Aug. 20, 2008, 13 pgs.
U.S. Appl. No. 11/316,120, Decision on Pre-Appeal Brief Request dated Apr. 19, 2011, 2 pgs.
U.S. Appl. No. 11/316,120, Final Office Action dated Oct. 28, 2010, 8 pgs.
U.S. Appl. No. 11/316,120, Non Final Office Action dated Apr. 11, 2008, 7 pgs.
U.S. Appl. No. 11/316,120, Non-Final Office Action dated May 27, 2010, 7 pgs.
U.S. Appl. No. 11/316,120, Notice of Allowance dated Jun. 20, 2011, 7 pgs.
U.S. Appl. No. 11/316,120, Pre-Appeal Brief Request filed Mar. 25, 2011, 5 pgs.
U.S. Appl. No. 11/316,120, Response filed Apr. 12, 2010 to Final Office Action dated Nov. 12, 2009, 12 pgs.
Busch et al., "On the Heating of Inductively Coupled Resonators (Stents) During MRI Examinations", Magnetic Resonance in Medicine, vol. 54, ??. 775-785, 2005.
European Application Serial No. 05815206.7, Communication dated Dec. 18, 2009, 4 pgs.
European Application Serial No. 05815206.7, Office Action dated May 16, 2012, 5 pgs.
European Application Serial No. 05815206.7, Response filed Apr. 19, 2010 to Communication dated Dec. 18, 2009, 27 pgs.
European Application Serial No. 05815215.8, Communication dated Dec. 18, 2009, 2 pgs.
European Application Serial No. 05815215.8, Response filed Mar. 19, 2010 to Communication dated Dec. 18, 2009, 12 pgs.
European Application Serial No. 05817448.3, Communication dated Dec. 18, 2009, 2 pgs.
European Application Serial No. 05817448.3, Office Action dated May 16, 2012, 5 pgs.
European Application Serial No. 05817448.3, Response filed Mar. 19, 2010 to Communication dated Dec. 18, 2009, 9 pgs.
European Application Serial No. 06790023.3, Office Action dated Mar. 4, 2009, 6 pgs.
European Application Serial No. 06825988.6, Office Action dated Mar. 4, 2009., 7 pgs.
European Application Serial No. 07759589.0 Office Action Response filed Jun. 24, 2010, 6 pgs.
European Application Serial No. 07759589.0, Office Action dated Feb. 18, 2010, 3 pgs.
European Application Serial No. 07759589.0, Office Action dated Jan. 29, 2009, 3 pgs.
European Application Serial No. 07759589.0, Response filed Jun. 24, 2010 to Office Action dated Feb. 18, 2010, 6 pgs.
European Application Serial No. 07759589.0, Response filed Jun. 5, 2009 to Office Action dated Jan. 29, 2009, 6 pgs.
European Application Serial No. 07759589.0, Summons to Attend Oral Proceedings dated May 17, 2011, 3 pgs.
European Application Serial No. 07759589.0, Written Submission filed Dec. 5, 2011 to Summons to Attend Oral Proceedings dated May 17, 2011, 16 pgs.
International Application Serial No. PCT/US2005/037978, International Search Report dated Jun. 13, 2006, 5 pgs.
International Application Serial No. PCT/US2005/037978, Written Opinion dated Jun. 13, 2006, 12 pgs.
International Application Serial No. PCT/US2005/037979, International Search Report dated Mar. 21, 2006, 4 pgs.
International Application Serial No. PCT/US2005/037979,Written Opinion dated Mar. 21, 2006, 8 pgs.
International Application Serial No. PCT/US2006/040291, Search Report dated Apr. 4, 2007, 5 pgs.
International Application Serial No. PCT/US2006/040291, Written Opinion dated Apr. 4, 2007, 9 pgs.
International Application Serial No. PCT/US2007/078405, International Search Report dated May 20, 2008, 5 pgs.
International Application Serial No. PCT/US2007/078405, International Search Report dated May 20, 2008, ?.220, 7 pgs.
International Application Serial No. PCT/US2007/078405, Written Opinion dated May 20, 2008, ?. 237, 7 pgs.
International Application Serial No. PCT/US2009/000693, International Search Report dated May 8, 2009, 5 pgs.
International Application Serial No. PCT/US2009/000693, Written Opinion dated May 8, 2009, 8 pgs.
Japanese Application Serial No. 2007-538087, Office Action dated Apr. 11, 2011, (w/ English Translation), 5 pgs.
Japanese Application Serial No. 2007-538087, Office Action dated Apr. 17, 2012, (w/ English Translation, 8 pgs.
Japanese Application Serial No. 2007-538087, Office Action dated Oct. 5, 2011, (w/ English Translation), 14 pgs.
Japanese Application Serial No. 2007-538087, Response filed Jul. 13, 2012 to Office Action dated Apr. 17, 2012, w/ English Translation of Amended Claims), 13 pgs.
Japanese Application Serial No. 2007-538087, Response filed Jun. 27, 2011 to Office Action dated Apr. 11, 2011, (w/ English Translation of Amended Claims), 12 pgs.

(56) References Cited

OTHER PUBLICATIONS

Japanese Application Serial No. 2007-538087, Response filed Mar. 23, 2012 to Office Action dated Oct. 5, 2011, (w/ English Translation of Claims), 9 pgs.

Japanese Application Serial No. 2007-538088, Notice of Final Rejection dated Dec. 6, 2011, (w/ English Translation), 9 pgs.

Japanese Application Serial No. 2007-538088, Office Action dated Jun. 13, 2011, (w/ English Translation), 5 pgs.

Japanese Application Serial No. 2007-538088, Response filed Aug. 25, 2011 to Office Action dated Jun. 13, 2011, (w/ English Translation of Amended Claims), 9 pgs.

Japanese Application Serial No. 2007-538088, Response filed Mar. 27, 2012 to Final Office Action dated Dec. 6, 2011, (w/ English Translation of Claims), 11 pgs.

Japanese Application Serial No. 2007-538089, Office Action dated Mar. 3, 2011, (w/ English Translation), 6 pgs.

Japanese Application Serial No. 2007-538089, Response filed May 25, 2011 to Office Action dated Mar. 3, 2011, (w/ English Translation of Amended Claims), 8 pgs.

Japanese Application Serial No. 2008-544322, Response filed Mar. 19, 2012 to Office Action dated Nov. 29, 2011, (w/ English Translation of Amended Claims), 9 pgs.

Japanese Application Serial No. 2008-544324, Office Action dated May 22, 2012, (w/ English Translation), 5 pgs.

Japanese Application Serial No. 2008-544324, Office Action dated Nov. 22, 2011, (w/ English Translation), 5 pgs.

Japanese Application Serial No. 2008-544324, Response filed Jan. 27, 2012, (w/ English Translation of Amended Claims), 10 pgs.

Japanese Application Serial No. 2008-544332, Office Action dated Nov. 29, 2011, (w/ English Translation), 5 pgs.

Japanese Application Serial No. 2009-503252, Office Action dated Mar. 21, 2012, (w/ English Translation), 9 pgs.

Japanese Application Serial No. 2009-503252, Response filed Jun. 20, 2012 to Office Action dated Mar. 21, 2012, (w/ English Claims), 9 pgs.

Manoharan et al, "Novel passive implantable atrial defibrillator using transcutaneous radiofrequency energy transmission successfully cardioverts atrial fibrillation.", Circulation, vol. 108(11), ??. 1382-1388, Sep. 16, 2003.

PCT Application No. PCT/US2007/074135, International Search Report dated Nov. 6, 2007, 4 pgs.

\* cited by examiner

LEADLESS CARDIAC STIMULATION SYSTEMS

CLAIM OF PRIORITY

This application is a continuation of U.S. patent application Ser. No. 15/380,160, filed on Dec. 15, 2016, now issued as U.S. Pat. No. 10,029,092, which is a continuation of U.S. patent application Ser. No. 14/223,506, filed on Mar. 24, 2014, now issued as U.S. Pat. No. 9,545,513, which is a continuation of U.S. patent application Ser. No. 13/717,027, filed on Dec. 17, 2012, now issued as U.S. Pat. No. 10,076,658, which is a continuation of U.S. patent application Ser. No. 11/745,105, filed on May 7, 2007, now issued as U.S. Pat. No. 8,340,780, which is a divisional of U.S. patent application Ser. No. 11/075,376 filed on Mar. 7, 2005, now issued as U.S. Pat. No. 7,647,109, which is a continuation-in-part of U.S. patent application Ser. No. 10/971,550, filed on Oct. 20, 2004, now issued as U.S. Pat. No. 7,532,933, the benefit of priority of each of which is hereby presently claimed, and the entire contents of each of which is hereby incorporated by reference.

TECHNICAL FIELD

This document relates to systems that electrically stimulate cardiac or other tissue and that do so without using leads that extend into the heart or other surrounding tissue or organs, along with systems and methods for introducing such stimulators.

BACKGROUND

Pacemakers provide electrical stimulus to heart tissue to cause the heart to contract and hence pump blood. Conventionally, pacemakers include a pulse generator that is implanted, typically in a patient's pectoral region just under the skin. One or more leads extend from the pulse generator and into chambers of the heart, most commonly into the right ventricle and the right atrium, although sometimes also into a vein over the left chambers of the heart. An electrode is at a far end of a lead and provides the electrical contact to the heart tissue for delivery of the electrical pulses generated by the pulse generator and delivered to the electrode through the lead.

The conventional use of leads that extend from the pulse generator and into the heart chambers has various drawbacks. For example, leads have at their far ends a mechanism, such as tines or a "j-hook," that causes the lead to be secured to a tissue region where a physician positions the lead. Over time, the heart tissue becomes intertwined with the lead to keep the lead in place. Although this is advantageous in that it ensures the tissue region selected by the physician continues to be the region that is paced even after the patient has left the hospital, it is also disadvantageous in the event of a lead failure or in the event it is later found that it would be more desirable to pace a different location than the tissue region initially selected. Failed leads cannot always be left in the patient's body, due to any potential adverse reaction the leads may have on heart function, including infection, thrombosis, valve dysfunction, etc. Therefore, difficult lead removal procedures sometimes must be employed.

The conventional use of leads also limits the number of sites of heart tissue at which electrical energy may be delivered. The reason the use of leads is limiting is that leads most commonly are positioned within cardiac veins. As shown in FIG. 17, up to three leads 2, 3 and 4 are implanted in conventional pacing systems that perform multiple-site pacing of the heart 1, with the leads exiting the right atrium 5 via the superior vena cava 6. Multiple leads may block a clinically significant fraction of the cross section of the vena cava and branching veins leading to the pacemaker implant.

No commercial pacing lead has been indicated for use in the chambers of the left side of the heart. This is because the high pumping pressure on the left side of the heart may eject a thrombus or clot that forms on a lead or electrode into distal arteries feeding critical tissues and causing stroke or other embolic injury. Thus, conventional systems, as shown in FIG. 17, designed to pace the left side of the heart thread a pacing lead 2 through the coronary sinus ostium 7, located in the right atrium 5, and through the coronary venous system 8 to a location 9 in a vein over the site to be paced on the left side. While a single lead may occlude a vein over the left heart locally, this is overcome by the fact that other veins may compensate for the occlusion and deliver more blood to the heart. Nevertheless, multiple leads positioned in veins would cause significant occlusion, particularly in veins such as the coronary sinus that would require multiple side-by-side leads.

There are several heart conditions that may benefit from pacing at multiple sites of heart tissue. One such condition is congestive heart failure (CHF). It has been found that CHF patients have benefited from bi-ventricular pacing, that is, pacing of both the left ventricle and the right ventricle in a timed relationship. Such therapy has been referred to as "resynchronization therapy." It is believed that many more patients could benefit if multiple sites in the left and right ventricles could be synchronously paced. In addition, pacing at multiple sites may be beneficial where heart tissue through which electrical energy must propagate is scarred or dysfunctional, which condition halts or alters the propagation of an electrical signal through that heart tissue. In these cases multiple-site pacing may be useful to restart the propagation of the electrical signal immediately downstream of the dead or sick tissue area. Synchronized pacing at multiple sites on the heart may inhibit the onset of fibrillation resulting from slow or aberrant conduction, thus reducing the need for implanted or external cardiac defibrillators. Arrhythmias may result from slow conduction or enlargement of the heart chamber. In these diseases, a depolarization wave that has taken a long and/or slow path around a heart chamber may return to its starting point after that tissue has had time to re-polarize In this way, a never ending "race-track" or "circus" wave may exist in one or more chambers that is not synchronized with normal sinus rhythm. Atrial fibrillation, a common and life threatening condition, may often be associated with such conduction abnormalities. Pacing at a sufficient number of sites in one or more heart chambers, for example in the atria, may force all tissue to depolarize in a synchronous manner to prevent the race-track and circus rhythms that lead to fibrillation.

Systems using wireless electrodes that are attached to the epicardial surface of the heart to stimulate heart tissue have been suggested as a way of overcoming the limitations that leads pose. In the suggested system, wireless electrodes receive energy for generating a pacing electrical pulse via inductive coupling of a coil in the electrode to a radio frequency (RF) antenna attached to a central pacing controller, which may also be implanted. The wireless electrodes are screwed into the outside surface of the heart wall.

SUMMARY

The invention is directed to various configurations of systems that employ leadless electrodes to provide pacing therapy and that are commercially practicable. One of the findings of the inventors is that a significant issue to be considered in achieving a commercially practicable system is the overall energy efficiency of the implanted system. For example, the energy transfer efficiency of two inductively coupled coils decreases dramatically as the distance between the coils increases. Thus, for example, a transmitter coil implanted in the usual upper pectoral region may only be able to couple negligible energy to a small seed electrode coil located within the heart.

One aspect of the invention may include a catheter delivery system for implantation of at least a portion of a wireless electrode assembly through endocardium tissue and into myocardium tissue. The catheter delivery system may include a first elongate member having a proximal end and a distal end and defining a lumen passing therethrough. The system may also include a second elongate member having a proximal end and a distal end. The system may further include a wireless electrode assembly attachable to the distal end of the second elongate member. When the electrode assembly is attached to the second elongate member, the second elongate member may be passable through the lumen to deliver at least a portion of the electrode assembly through the endocardium and into the myocardium.

In some embodiments, the electrode assembly may include an attachment mechanism that has at least one fastener to penetrate through the endocardium and into the myocardium. The attachment mechanism may be operable to secure at least a portion of the electrode assembly to the myocardium. In some instances, the attachment mechanism may include at least one helical tine and at least one curled tine. For example, the attachment mechanism may include a distally extending helical tine to penetrate through the endocardium and into the myocardium and a plurality of radially extending curled tines. In other instances, the fastener of the attachment mechanism may include a tine, screw, barb, or hook.

In further embodiments, the second elongate member may have a detachment mechanism at the distal end to release the electrode assembly from the second elongate member after delivery of the electrode assembly to the myocardium. In some instances, the detachment mechanism may include a threaded member that releasably engages a portion of the electrode assembly. In other instances, the detachment mechanism may include an adjustable locking member that releasably engages a portion of the electrode assembly.

In certain embodiments, the first elongate member includes a steering mechanism to direct the distal end of the first elongate member to a selected site proximate to the endocardium. The first elongate member may include an electrode at its distal end for sensing a local electrocardiogram at the selected site proximate to the endocardium.

In some embodiments, the system also includes an access catheter having a proximal end and a distal end and having a lumen passing therethrough. The first elongate member may be a delivery catheter that is passable through the lumen of the access catheter. An image device may be disposed near the distal end of the access catheter. The image device may include an ultrasonic device to provide visualization of a selected site distal of the access catheter.

In another aspect, an implantable wireless electrode assembly may include a first electrode to discharge a pacing electrical pulse. The assembly may also include an attachment mechanism having at least one fastener to penetrate through endocardium tissue and into myocardium tissue. At least a portion of the attachment mechanism may be disposed proximate to the electrode such that, when the fastener penetrates through the endocardium and into the myocardium, the electrode is positioned proximate to the myocardium.

In some embodiments, the wireless electrode assembly also includes a second electrode. The second electrode may be spaced apart from the first electrode such that, when the fastener penetrates through endocardium and into the myocardium, the first electrode is positioned proximate to the myocardium while the second electrode is exposed to blood in an internal heart chamber.

In further embodiments, the wireless electrode assembly may also include an induction device to receive electromagnetic energy from an external source. The first electrode may be electrically connected to a circuit such that the pacing electrical pulse is generated from at least a portion of the electromagnetic energy received by the induction device. The circuit may include an energy storage element to store the electromagnetic energy received by the induction device. The energy storage element may be operable to periodically discharge electrical energy to the electrode.

In certain embodiments, the wireless electrode assembly may include a induction device comprising a coil that is inductively coupled to the external source.

In some embodiments, the wireless electrode assembly may include an attachment mechanism that comprises at least one helical tine and at least one curled tine. The attachment mechanism may include a distally extending helical tine to penetrate through the endocardium and into the myocardium and may include a plurality of radially extending tines that are adapted to a curl into the endocardium or myocardium after the helical tine penetrates into the myocardium.

In other embodiments, the wireless electrode assembly may include attachment mechanism that comprises a tine, screw, barb, or hook.

In further embodiments, the wireless electrode assembly also includes a detachment mechanism spaced apart from the fastener of the attachment mechanism. The detachment mechanism may include a threaded member and may be operable to release the wireless electrode assembly from a delivery system after the fastener penetrates through endocardium and into the myocardium.

Yet another aspect may include a method of delivering a wireless electrode assembly into an internal heart chamber and proximate the myocardium. The method may include directing a distal end of a first elongate member into an internal heart chamber. The first elongate member may have the distal end, a proximal end, and a lumen passing therethrough. The method may also include directing a wireless electrode assembly through the lumen of the first elongate member toward the distal end of the first elongate member. The method may further include penetrating at least a portion of the wireless electrode assembly through endocardium tissue and into the myocardium.

In some embodiments, the method may employ a wireless electrode assembly that is attached to a distal end of a second elongate member. The second elongate member may be passable through the lumen of the first elongate member. In such cases, the method may also include operating a detachment mechanism to release the wireless electrode assembly from the first elongate member. Furthermore, the method may also include withdrawing the second elongate member and the first elongate member away from endocardium.

In certain embodiments, the method may also include measuring a local electrocardiogram with a sensor at the distal end of the first elongate member after at least a portion of the wireless electrode assembly penetrates the endocardium. In such cases, the method may also include deploying one or more adjustable tines of the wireless electrode assembly after measuring the local electrocardiogram. In certain circumstances, the method may include withdrawing the wireless electrode assembly from the myocardium after measuring the local electrocardiogram and penetrating at least a portion of the wireless electrode assembly through a different portion the endocardium and into a different portion of the myocardium.

In some embodiments, the operation of penetrating at least a portion of the wireless electrode assembly through endocardium tissue includes causing an attachment mechanism of the electrode assembly to penetrate through the endocardium.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

This document describes various configurations of systems that employ leadless electrodes to provide pacing therapy or other tissue excitation and that are commercially practicable. One of the findings of the inventors is that a significant issue to be considered in achieving a commercially practicable system is the overall energy efficiency of the implanted system. For example, the energy transfer efficiency of two inductively coupled coils decreases dramatically as the distance between the coils increases. Thus, for example, a transmitter coil implanted in the usual upper pectoral region may only be able to couple negligible energy to a small seed electrode coil located within the heart.

Figure 1:
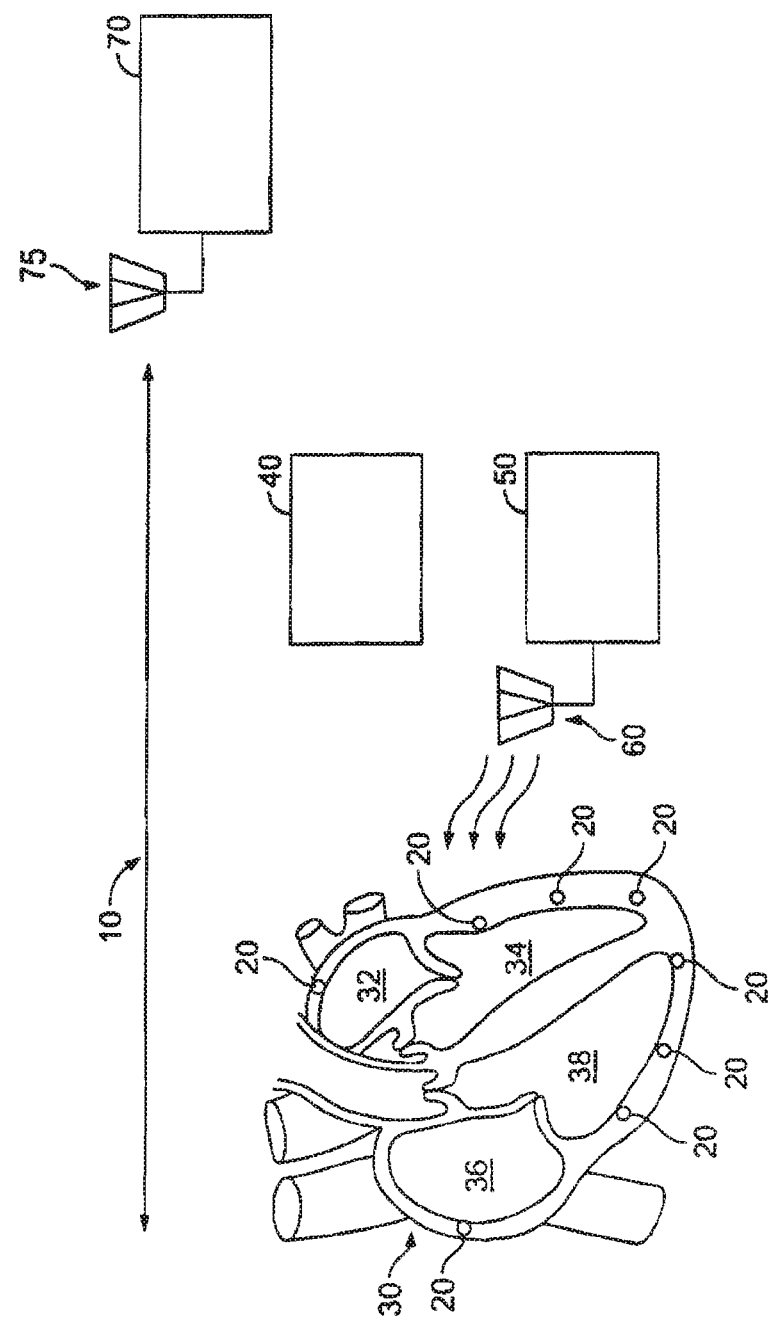
FIG. 1 is a conceptual diagram of a leadless cardiac stimulation system (with leadless, or wireless, electrode assemblies shown implanted in a heart) and of an external programmer.

FIG. 1 shows a general depiction of such a system 10 and an external programming device 70. The system 10 includes a number of wireless electrode assemblies 20, herein referred to simply as "seeds." The seeds 20 are implanted within chambers of the heart 30. In this example, there are eight seeds 20, there being one implanted in the left atrium 32, three implanted in the left ventricle 34, one implanted in the right atrium 36, and three implanted in the right ventricle 38. In one embodiment, each of the seeds 20 has an internal coil that is inductively coupled with an external power source coil to charge an electrical charge storage device contained within the seed 20, and also has a triggering mechanism to deliver stored electrical charge to adjacent heart tissue.

In another embodiment, one or more of the seeds has no energy storage device such as a battery or capacitor. In such a situation, each seed may be comprised, for example, of a ferrite core having caps at each end with ring electrodes encircling the caps, so as to form a dumbbell-shaped configuration. A number of turns of fine insulated wire may be wrapped around the central portion of the core so as to receive energy from a magnetic field produced by a shaped driving signal and designed to activate the electrodes. Such a configuration is discussed below in greater detail with reference to FIGS. 18A to 18C.

Referring again to FIG. 1, the system 10 also includes a pacing controller 40 and a transmitter 50 that drives an antenna 60 for communication with the seeds 20. Generally, the pacing controller 40 includes circuitry to sense and analyze the heart's electrical activity, and to determine if and when a pacing electrical pulse needs to be delivered and by which of the seeds 20. The sensing capability may be made possible by having sense electrodes included within the physical assembly of the pacing controller 40. Alternatively, a conventional single or dual lead pacemaker (not shown in FIG. 1; although see FIG. 2B) may sense the local cardiac electrocardiogram (ECG) and transmit this information to antenna 60 for use by controller 40 in determination of the timing of seed firing. In either case, the seed 20 need not be provided with sensing capability, and also the seeds 20 need not be equipped with the capability of communicating to the pacing controller 40 (for example, to communicate information about sensed electrical events). In alternative embodiments, the seeds may communicate sensed information to each other and/or to the controller 40.

The transmitter 50—which is in communication with, and is controlled by, the pacing controller 40—drives an RF signal onto the antenna 60. In one embodiment, the transmitter 50 provides both 1) a charging signal to charge the electrical charge storage devices contained within the seeds 20 by inductive coupling, and 2) an information signal, such as a pacing trigger signal, that is communicated to a selected one or more of the seeds 20, commanding that seed to deliver its stored charge to the adjacent tissue.

An important parameter of the seed 20 that is a driver of the system 10 design is the maximum energy required to pace the ventricle. This energy requirement can include a typical value needed to pace ventricular myocardium, but also can include a margin to account for degradation of contact between the electrodes and tissue over time. It is assumed that each seed may require the maximum pacing threshold energy. This threshold energy is supplied to the seeds between heartbeats by an external radio frequency generator (which may also be implanted), or other suitable energy source that may be implanted within the body. Typical values are:

Threshold pacing voltage=2.5 Volts
Typical lead impedance=600 Ohms
Typical pulse duration=0.4 mSec
Derived threshold energy=4 micro-Joules Because RF fields at frequencies higher than about 100 kHz are attenuated by the body's electrical conductivity, and because electric fields of any frequency are attenuated within the body, energy transmission through the body may be accomplished via a magnetic field at about 20-100 kHz (or by a magnetic field pulse that contains major frequency components in this range), and preferably by transmission of magnetic fields in the range of 20-30 kHz when transmission is through relatively conductive blood and heart muscle.

As will be seen later in some of the specifically described configurations of the system 10, the pacing controller 40 and the transmitter 50 may be housed in a single enclosure that is body implantable within a patient. In such a configuration, the single enclosure device may have a single energy source (battery) that may be either rechargeable or non-rechargeable. In another configuration, the pacing controller 40 and the transmitter 50 may be physically separate components. As an example of such a configuration, the pacing controller 50 may be implantable, for example in the conventional pacemaker configuration, whereas the transmitter 50 (along with the antenna 60) may be adapted to be worn externally, such as in a harness that is worn by the patient. In the latter example, the pacing controller 40 would have its own energy source (battery), and that energy would not be rechargeable given the relatively small energy requirements of the pacing controller 40 as compared to the energy requirements of the transmitter 50 to be able to electrically charge the seeds 20.

In this case, the pacing controller 40 would sense the local cardiac ECG signal through a conventional pacing lead, and transmit the sensed information to the external controller. Again, transmission of information, as opposed to pacing energy, has a relatively low power requirement, so a conventional pacemaker enclosure and battery would suffice.

The external programmer 70 is used to communicate with the pacing controller 40, including after the pacing controller 40 has been implanted. The external programmer 70 may be used to program such parameters as the timing of stimulation pulses in relation to certain sensed electrical activity of the heart, the energy level of stimulation pulses, the duration of stimulation pulse (that is, pulse width), etc. The programmer 70 includes an antenna 75 to communicate with the pacing controller 40, using, for example, RF signals. The implantable pacing controller 40 is accordingly equipped to communicate with the external programmer 70, using, for example, RF signals. The antenna 60 may be used to provide such communications, or alternatively, the pacing controller 40 may have an additional antenna (not shown in FIG. 1) for external communications with the programmer 70, and in an embodiment where the transmitter 50 and antenna 60 are housed separately from the controller 40, for communications with the transmitter 50.

Figure 2A:
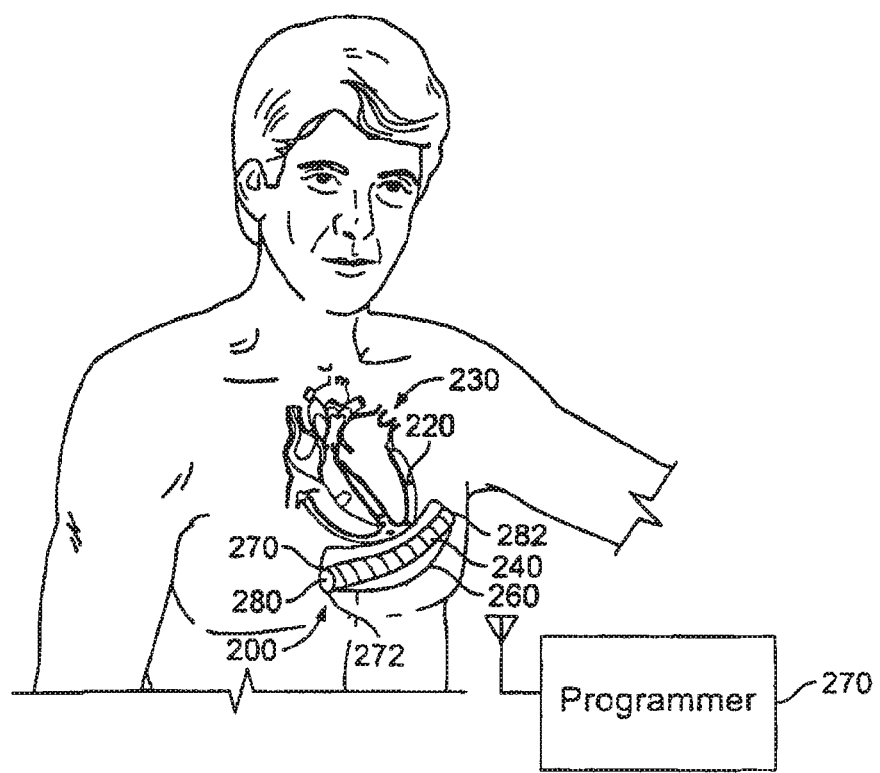
FIGS. 2A and 2B are exemplary systems of the type shown in FIG. 1, and shown implanted in a body.

FIG. 2A shows an example system 200 of the type shown in FIG. 1. The system 200 is shown as having been implanted in a patient, and in addition, a programmer 270 is also shown that is external to the patient. As shown, the system 200 is of a type that is entirely implantable. The system 200 includes several seed electrode assemblies 220, there being four such assemblies shown as having been implanted within the heart 230 in FIG. 2A. The system 200 also includes an implantable combined pacing controller and transmitter device 240 that has an antenna 260 for communicating, for example, to the seeds 220. The controller/transmitter device 240 is shaped generally elongate and slightly curved so that it may be anchored between two ribs of the patient, or possibly around two or more ribs. In one example, the controller/transmitter device 240 is 2 to 20 cm long and 1 to 10 centimeters (cm) in diameter, preferably 5 to 10 cm long and 3 to 6 cm in diameter. Such a shape of the controller/transmitter device 240, which allows the device 240 to be anchored on the ribs, allows an enclosure that is larger and heavier than conventional pacemakers, and allows a larger battery having more stored energy. Other sizes and configurations may also be employed as is practical.

The antenna 260 in the FIG. 2A example is a loop antenna comprised of a long wire whose two ends 270 and 272 extend out of the housing of the controller/transmitter device 240 at one end 280 of the controller/transmitter device 240. The opposite ends 270 and 272 of the loop antenna 260 are electrically connected across an electronic circuit contained within the controller/transmitter device 240, which circuit delivers pulses of RF current to the antenna, generating a magnetic field in the space around the antenna to charge the seeds, as well as RF control magnetic field signals to command the seeds to discharge. The loop antenna 260 may be made of a flexible conductive material so that it may be manipulated by a physician during implantation into a configuration that achieves improved inductive coupling between the antenna 260 and the coils within the implanted seeds 220. In one example, the loop antenna 260 may be 2 to 22 cm long, and 1 to 11 cm wide, preferably 5 to 11 cm long, and 3 to 7 cm wide. Placement of the antenna over the ribs allows a relatively large antenna to be constructed that has improved efficiency in coupling RF energy to the pacing seeds.

In FIG. 2A, the loop antenna 260 has been configured to extend generally around the periphery of the housing of the controller/transmitter device 240. In particular, the loop antenna 260 extends from its first end 270 (located at the first end 280 of the controller/transmitter device 240) outwardly and then generally parallel to the elongately shaped controller/transmitter device 240 to the second end 282 of the controller/transmitter device 240. From there, the loop antenna 260 extends outwardly and again generally parallel to the controller/transmitter device 240, albeit on an opposite side of the transmitter/controller device 240, and back to the first end 280 of the controller/transmitter device 240. As such, the loop antenna 260 may, like the controller/transmitter device 240, be anchored to the ribs of the patient.

In this configuration, the distance between the center of the loop antenna 260 and the seed electrode assemblies 220 will typically be, on average, about three inches (3"). As will be shown later, such a distance puts significant power demands on the controller/transmitter device 240, and so an internal battery included within the controller/transmitter device 240 may need to be rechargeable. In some embodiments, however, the controller/transmitter device 240 may be non-rechargeable. The loop antenna 260 may have a shape that is more complex than that shown in FIG. 2, with a larger antenna area, or multiple antenna lobes to capture more tissue volume. The antenna may consist of two or more wire loops, for example, one on the front of the patient's rib cage, and a second on the back, to gain magnetic field access to a larger tissue region.

Figure 2B:
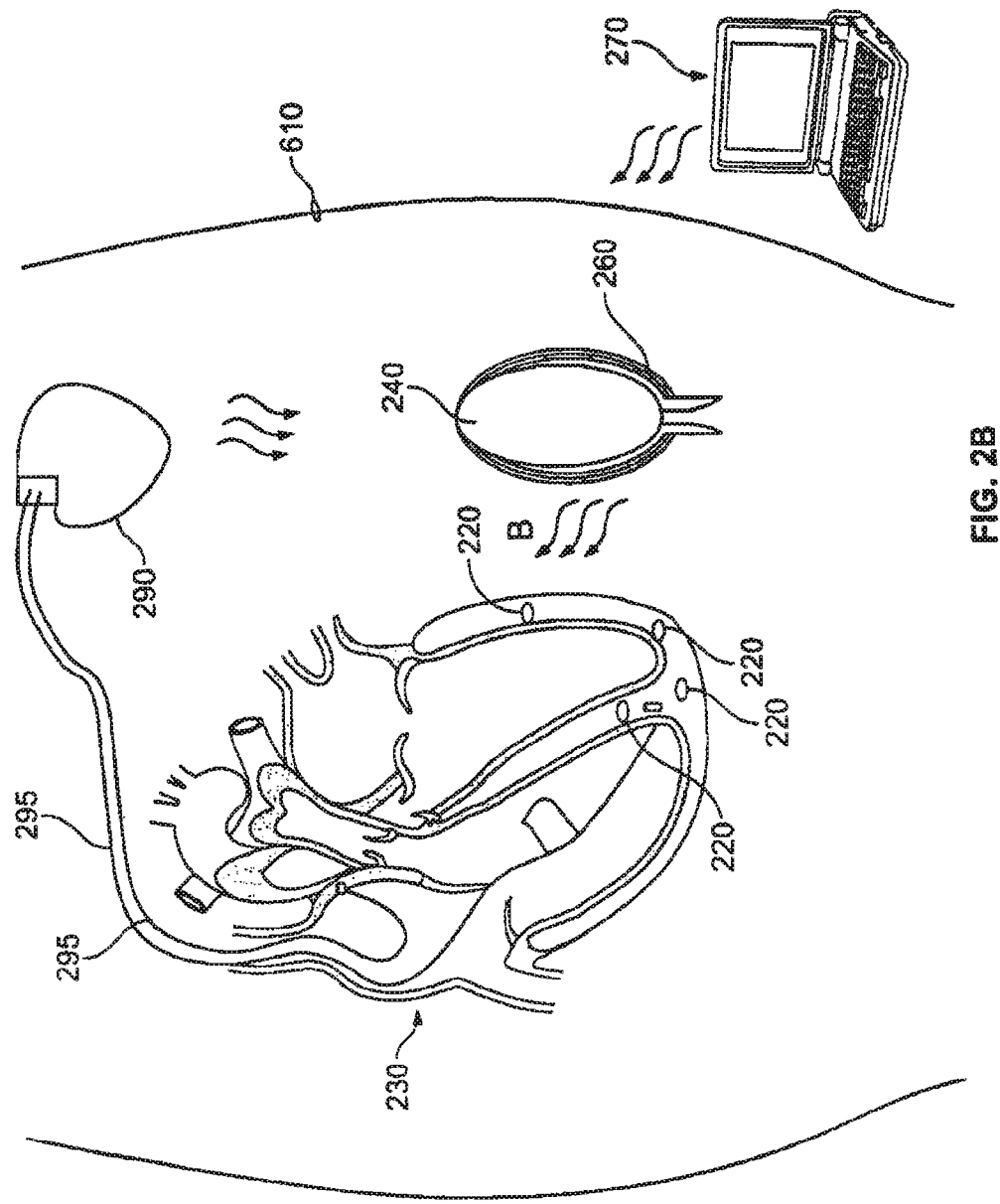

Referring to FIG. 2B, there is shown an embodiment as shown in FIG. 2A, but which also includes a conventional pacemaker, or pulse generator, 290 and associated wired leads 295 which extend from the pulse generator 290 and into chambers of the heart 600. As such, the pulse generator 290 may be used to sense the internal ECG, and may also communicate with the controller/transmitter 240 as discussed previously.

Figure 3:
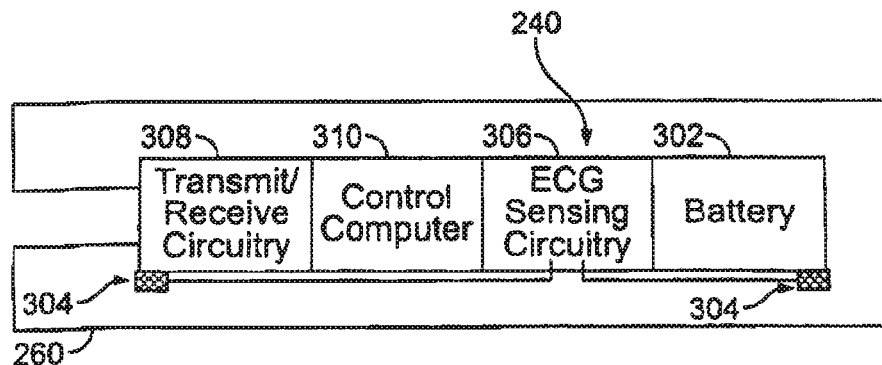
FIG. 3 is a block diagram of an exemplary embodiment of a combined controller/transmitter device and associated antenna that may be used as part of the FIG. 2A or 2B system.

Referring to FIG. 3, an embodiment of the controller/transmitter 240 and associated loop antenna 260 is shown in block diagram form. Included within the pacing controller 240 is: a battery 302, which may be recharged by receiving RF energy from a source outside the body via antenna 260; ECG sensing electrodes 304 and associated sensing circuitry 306; circuitry 308 for transmitting firing commands to the implanted seeds, transmitting status information to the external programmer, receiving control instructions from the external programmer and receiving power to recharge the battery; and a controller or computer 310 that is programmed to control the overall functioning of the pacing control implant. In alternative embodiments, antenna 260 may receive signals from the individual seeds 220 containing information regarding the local ECG at the site of each seed, and/or antenna 260 may receive signals from a more conventional implanted pacemaker regarding the ECG signal at the sites of one or more conventional leads implanted on the right side of the heart.

Figure 4:
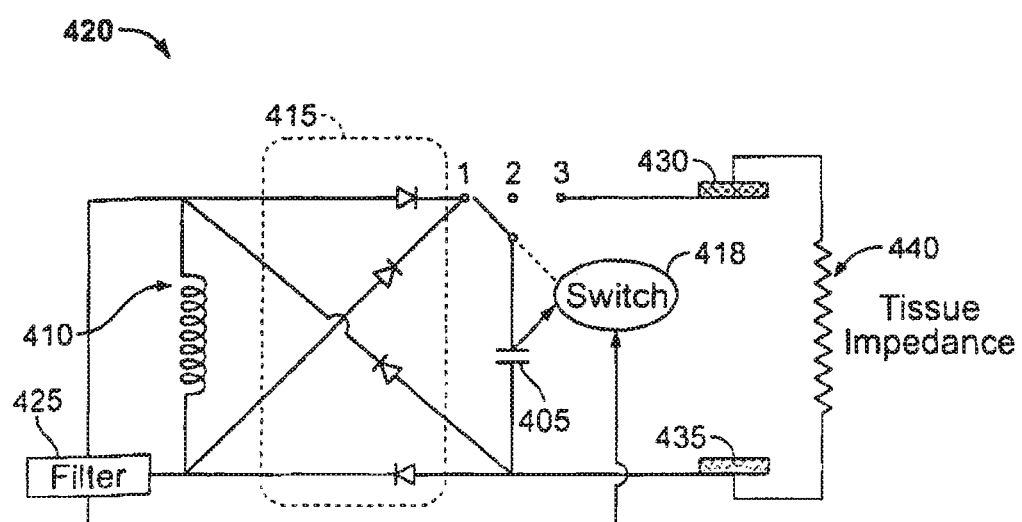
FIG. 4 is a schematic diagram of a portion of the circuitry included in a wireless electrode assembly as is shown in FIGS. 1 and 2A-B.

FIG. 4 is a schematic diagram of an exemplary wireless electrode assembly, or seed, 420 that may serve as the seeds 20 or 220 as shown in either FIG. 1 or FIGS. 2A-B. The seed 420 includes, firstly, a receiver coil 410 that is capable of being inductively coupled to a magnetic field source generating a time-varying magnetic field at the location of coil 410, such as would be generated by the transmitter 50 and the antenna 60 shown in FIG. 1. The RF current in the external antenna may be a pulsed alternating current (AC) or a pulsed DC current, and thus the current induced through the receiver coil 410 would likewise be an AC or pulsed DC current. The current induced in coil 410 is proportional to the time rate of change of the magnetic field generated at the site of coil 410 by the external RF current source. A four-diode bridge rectifier 415 is connected across the receiver coil 410 to rectify the AC or pulsed DC current that is induced in the receiver coil 410. A three-position switch device 418 is connected so that when the switch device 418 is in a first position, the rectifier 415 produces a rectified output that is imposed across a capacitor 405. As such, when the switch device 418 is in the position 1 (as is the case in FIG. 4), the capacitor 405 stores the induced electrical energy.

The switch device 418, in this example, is a voltage-controlled device and is connected to sense a voltage across the capacitor 405 to determine when the capacitor 405 has been sufficiently charged to a specified pacing threshold voltage level. When the capacitor 405 is sensed to have reached the specified pacing threshold level, the voltage-controlled switch device 418 moves to a position 2, which disconnects the capacitor 405 from the coil 510. With the switch device 418 in the position 2, the capacitor 405 is electrically isolated and remains charged, and thus is ready to be discharged. The voltage controlled switch device 418 may consist of a solid state switch, such as a field effect transistor, with its gate connected to the output of a voltage comparator that compares the voltage on capacitor 405 to a reference voltage. The reference voltage may be set at the factory, or adjusted remotely after implant via signals sent from the physician programmer unit, received by coil 410 and processed by circuitry not shown in FIG. 4. Any electronic circuitry contained within the seed, including the voltage controlled switch, is constructed with components that consume very little power, for example CMOS. Power for such circuitry is either taken from a micro-battery contained within the seed, or supplied by draining a small amount of charge from capacitor 405.

A narrow band pass filter device 425 is also connected across the receiver coil 410, as well as being connected to the three-position switch device 418. The band pass filter device 425 passes only a single frequency of communication signal that is induced in the coil 410. The single frequency of the communication signal that is passed by the filter device 425 is unique for the particular seed 20 as compared to other implanted seeds. When the receiver coil 410 receives a short magnetic field burst at this particular frequency, the filter device 425 passes the voltage to the switch device 418, which in turn moves to a position 3.

With the switch device in the position 3, the capacitor 405 is connected in series through two bipolar electrodes 430 and 435, to the tissue to be stimulated. As such, at least some of the charge that is stored on the capacitor 405 is discharged through the tissue. When this happens, the tissue becomes electrically depolarized. In one example embodiment that will be shown in more detail later, the bipolar electrodes 430 and 435 across which stimulation pulses are provided are physically located at opposite ends of the seed 420. After a predetermined, or programmed, period of time, the switch returns to position 1 so the capacitor 405 may be charged back up to the selected threshold level.

It should be noted that, for sake of clarity, the schematic diagram of FIG. 4 shows only the seed electrical components for energy storage and switching. Not shown are electronics to condition the pacing pulse delivered to the tissues, which circuitry would be known to persons skilled in the art. Some aspects of the pulse, for example pulse width and amplitude, may be remotely programmable via encoded signals received through the filter device 425 of the seed 420. In this regard, filter 425 may be a simple band pass filter with a frequency unique to a particular seed, and the incoming signal may be modulated with programming information. Alternatively, filter 425 may consist of any type of demodulator or decoder that receives analog or digital information induced by the external source in coil 410. The received information may contain a code unique to each seed to command discharge of capacitor 405, along with more elaborate instructions controlling discharge parameters such as threshold voltage for firing, duration and shape of the discharge pulse, etc.

Using seeds of the type shown in FIG. 4, all of the implanted seeds may be charged simultaneously by a single burst of an RF charging field from a transmitter antenna 60. Because back reaction of the tiny seeds on the antenna 60 is small, transmitter 50 (FIG. 1) losses are primarily due to Ohmic heating of the transmit antenna 60 during the transmit burst, Ohmic heating of the receive coil 410, and Ohmic heating of conductive body tissues by eddy currents induced in these tissues by the applied RF magnetic field. By way of comparison, if eight seeds are implanted and each is addressed independently for charging, the transmitter 50 would be turned ON eight times as long, requiring almost eight times more transmit energy, the additional energy being primarily lost in heating of the transmit antenna 60 and conductive body tissues. With the seed 420 of FIG. 4, however, all implanted seeds are charged simultaneously with a burst of RF current in antenna 260, and antenna and body tissue heating occurs only during the time required for this single short burst. Each seed is addressed independently through its filter device 425 to trigger pacing. The transmitted trigger fields can be of much smaller amplitude, and therefore lose much less energy to Ohmic heating, than the transmitted charging pulse.

Figure 5:
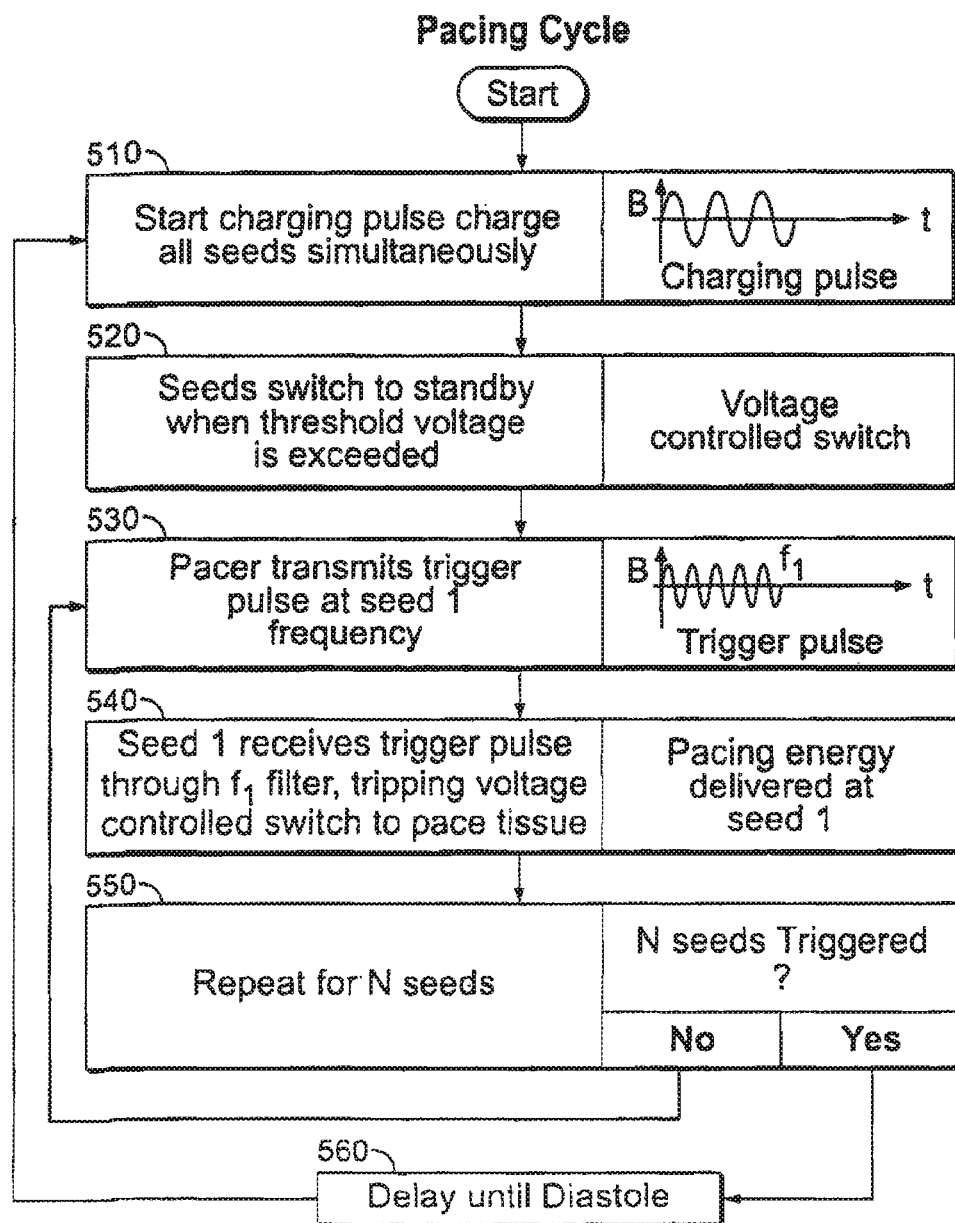
FIG. 5 is a flow chart of a method of providing stimulation pulses in a pacing cycle in a system such as shown in FIGS. 1 and 2A-B.

FIG. 5 is a flowchart of a pacing cycle that shows such a mode of operation of charging all implanted seeds 20 simultaneously, and triggering the discharge of each seed 20 independently. The method starts at step 510 with the start of a charging pulse that charges all of the seeds simultaneously. When a pacing threshold voltage is attained or exceeded, at step 520, the seeds switch to a standby mode (for example, switch 418 in seed 420 moves to position 2). Next, in step 530, at the appropriate time, a controller/transmitter device such as device 240 shown in FIG. 2, transmits a trigger pulse at a particular frequency (f1) that is passed through a band pass filter (such as filter device 425) in the seed to be fired (for example, seed 1). Then, at step 540, that seed, namely seed 1, receives the trigger pulse through the band pass filter, which in turn trips the switch to pace the tissue. This process may be repeated for each of the N number of seeds that have been implanted, as indicated at step 550, which returns to step 530 where there are additional seeds that have been charged and are to be fired. Next, at step 560 there is a delay until the next diastole, after which time the process begins anew at step 510. The exact time of firing of the first seed may be programmed by the physician in relation to the ECG signal features measured by the sensing electrodes 304 in FIG. 3, or in relation to ECG information transmitted to the controller 240 by the pacing seeds themselves, or in relation to pacing information transmitted to the controller 240 by a conventional implanted pacemaker, or in relation to pacing information received from a conventional implanted pacemaker through an implanted hard wire connection to controller 240. Subsequent timing of the firing of each additional seed may be programmed by the physician at the time of implant. Note that seeds may be programmed not to discharge. For example, an array of seeds may be implanted, but only a subset may be programmed to receive firing commands from the controller 240.

In the case of FIG. 2A and other similar embodiments, it is envisioned that the controller/transmitter device 240 and associated antenna 260 would first be implanted subcutaneously in a designed location (for example, between the ribs in the case of the FIG. 2A embodiment). The physician then may program the controller/transmitter 240 by delivering telemetric signals through the skin using the programmer 270 in a conventional manner, although this programming may also be done, at least in part, before implantation. One of the adjustable parameters is the timing of firing of each seed 220, determined by a time at which a short burst of current at the frequency for the particular seed 220 is delivered to the antenna 260. The controller/transmitter device 240 may have a pair of sensing electrodes on its surface to detect the subcutaneous electrocardiogram (ECG), or it may contain multiple electrodes to provide a more detailed map of electrical activity from the heart. This local ECG signal sensed by the controller/transmitter device 240 may be used to trigger the onset of seed pacing when the patient has a functioning sinus node. In any case, the signals sensed by the controller/transmitter device 240 are used to monitor ECG signals from the paced heart. In some cases, these ECG signals, or other physiologic sensor input signals, may be used to adjust or adapt the timing of firing of the pacing seeds 220.

Alternatively, the controller 240 may receive local ECG or pacing information through an RF link from a conventional pacemaker 290 implanted in the pectoral region of the patient, as shown in FIG. 28. This may be desirable in patients who already have a conventional pacemaker, or when local ECG data from the conventional atrial or right ventricular apex pacing sites are desired to coordinate the timing of firing of the implanted seeds 220. Finally, the seeds 220 could themselves transmit information to controller 240 concerning the local bi-polar ECG measured at their sites. Alternatively, the seeds 220 could sense the local ECG and discharge based upon this local data, with no firing instructions from the controller 240 required, or the seeds 220 could transmit information from seed 220 to seed concerning local ECG and onset of their discharge. All of the above embodiments, a combination, or a subset, may be implemented in this invention.

In an example embodiment, the seeds 220 would be delivered to their respective sites in the cardiac veins, within the heart wall, or on the epicardial surface of the heart via a catheter, as will be described in more detail later. A distal portion, or tip of the catheter, may contain a single electrode or a pair of electrodes, each being connected to a signal recorder via leads extending to a proximal end of the catheter. As such, it is possible to obtain a uni-polar or bipolar ECG at the catheter distal tip. The physician would select the implantation site based upon features of the ECG signal sensed using the catheter. The seed then may be injected through a needle extended from the catheter tip, or it may be pushed into the tissue and then released from the catheter. Many mechanisms may be used for seed release, including the release or addition of fluid pressure to the catheter tip.

Once implanted, the seed 220 may be charged and then fired to observe the altered electrogram proximate the seed at the location of the catheter tip. The physician can adjust the timing of seed firing by programming the controller/ transmitter device 240. When satisfied with the local and controller/transmitter device 240 electrograms, the catheter (or a seed delivery mechanism residing within the catheter) may be removed, and a new delivery mechanism containing the next pacing seed may be inserted and navigated to the next pacing site. Because seeds can be fired in any order, or not fired at all, a physician may deliver the seeds in any order. When the heart is deemed to be beating in synchrony, no further seeds need be implanted. Alternatively, if it has been determined that the seeds are small enough that they do not substantially impair local tissue function, then an array of seeds may be delivered to the veins and/or heart wall, and the physician can program a subset of seeds to fire in a sequence that optimizes the pumping efficiency of the heart. Ejection fraction and cardiac output may be measured to determine pumping efficiency. On any given heartbeat, some or all of the seeds would fire. The controller 240 may be programmed to sequentially fire seeds, or some seeds may fire simultaneously.

Figure 6:
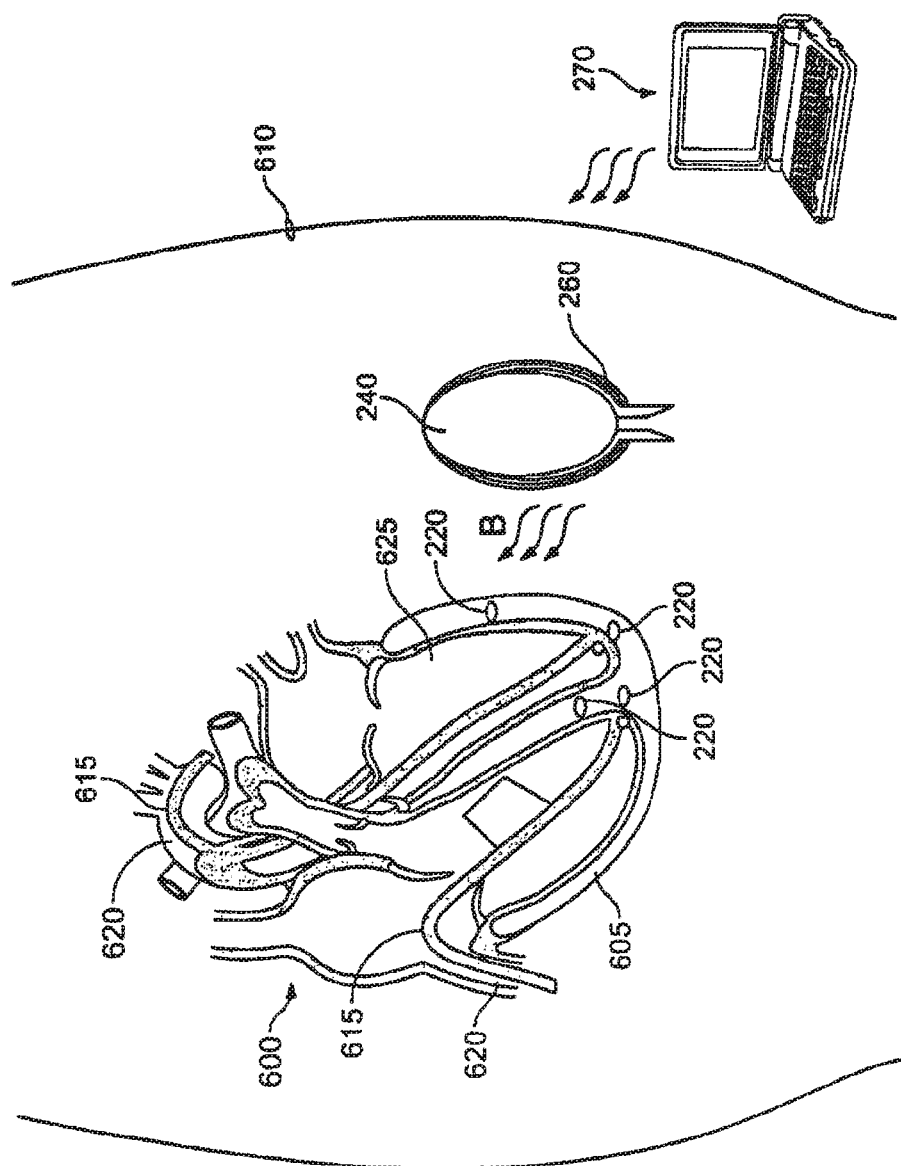
FIG. 6 is a diagram of the system shown in FIG. 2A and of an example wireless electrode assembly delivery catheter.

FIGS. 6-10 show an example of a mechanical design for a seed electrode assembly and an example seed delivery device and method. Referring first to FIG. 6, a system of the type shown in FIG. 2 is shown where three seed electrode assemblies 220 have been implanted within tissue of the heart 600, and in particular, within a myocardial wall 605 of the heart 600. In addition, the controller/transmitter device 240 is shown implanted beneath the skin 610 of the patient. The antenna 260 extends from within the controller/transmitter device 240 at one end of the device 240, and then extends around the periphery of the device 240, as described previously. The external programming device 270 is also shown, which is used to communicate with the implanted controller/transmitter 240.

Figure 9:
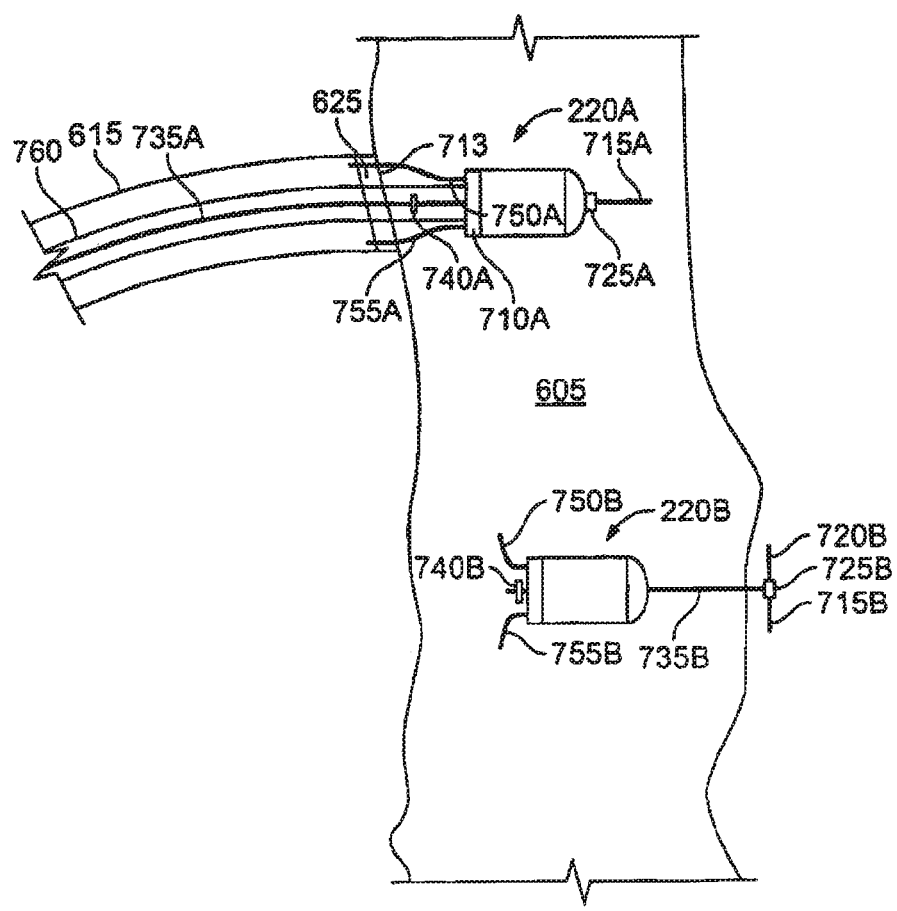
FIG. 9 is a diagram illustrating the delivery of a wireless electrode assembly from the delivery catheter and into the myocardial wall.

Distal portions of two seed delivery catheters 615 are shown in FIG. 6, each extending within a chamber of the heart 600 and to a site near where one of the seeds 220 is located. Generally, the delivery catheter 615 enables placement of a seed 220 and the ability to sense the electrical activity at the distal tip of delivery catheter 615 through catheter tip electrode 625, so that a physician can determine if the location is a good candidate location for implantation of seed 220. If the location is a good candidate, the seed 220 may be partially inserted into the tissue as shown in FIG. 9. With the seed 220 still tethered to a pull wire 735A, the seed 220 may be charged and then discharged into the tissue, while the physician observes electrograms, including the local electrogram arising from electrode 625, and perhaps an electrogram from the distal seed electrode taken through the pull wire 735A. Upon firing the seed, if the physician determines it is not in the proper location to optimize cardiac output, then the seed 220 may be removed from that site and positioned elsewhere. If it is an appropriate location, then the seed 220 has an anchoring mechanism that can be activated to implant the seed 220 permanently within the tissue so that it retains its location.

Each of the catheters 615 is shown in FIG. 6 extending into the heart 600 through a heart entry vessel 620 such as the inferior vena cava (for right chamber entry) or aortic valve (for left chamber entry). A distal portion 625 of the delivery catheter 615 includes a sensing electrode for sensing the electrical activity at a tissue site where the seed 220 may be implanted.

Figure 7:
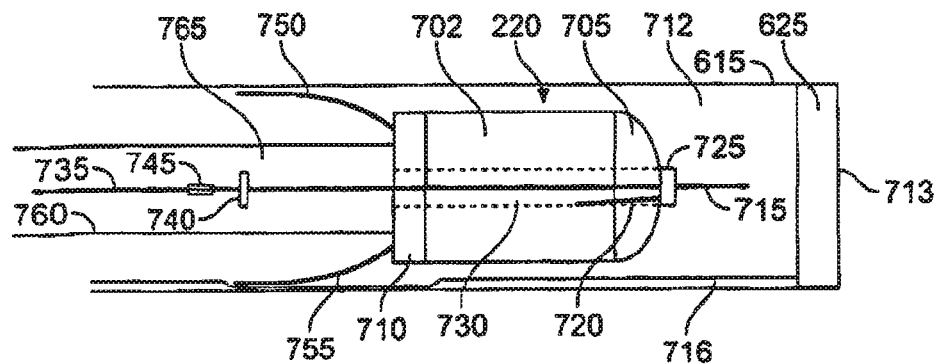
FIG. 7 is a side-view diagram of the delivery catheter shown in FIG. 6, with portions removed to show a wireless electrode assembly and additional assemblies inside the catheter.

FIG. 7 shows one of many possible embodiments of a wireless electrode assembly, or seed, 220. The seed 220 is shown in FIG. 7 within a distal portion of the seed delivery catheter 615. The seed 220 has a main body 702 that, in this example, is bullet shaped and has two bipolar electrodes 705 and 710. One of the electrodes, namely electrode 705, is located at a distal tip of the bullet-shaped seed body 702, and the other electrode 710 is located at a proximal end of the seed body 702. The bullet shape of the seed body 702 enables it to be extended into tissue such as the myocardial wall 605, as will be illustrated in later figures. In other embodiments, the "nose," or distal tip, of the seed body 702 may be more cone-shaped than the embodiment shown in FIG. 7. While the distal and proximal electrodes 705 and 710 are shown on the seed itself, other locations are possible, including placing the distal and proximal electrodes 705 and 710 at the ends of the attachment tines to achieve the maximum separation between electrodes.

The seed delivery catheter 615 consists of an elongate tube with a main lumen 712 extending though its entire length. The catheter 615 has an opening 713 at its distal end so that the seed 220 may be released from the delivery catheter 615. The catheter 615 also has the previously discussed electrode 625, which as shown extends around the periphery of the distal opening 713. An electrically conductive lead 716 is attached to the electrode 625 and extends proximally through the entire length of catheter lumen 712, or through the wall of the catheter, and outside the body (not shown in FIG. 7). The lead 716 is made of an electrically conductive material, and thus provides the local electrocardiogram (ECG) appearing at the distal electrode 625. As such, the electrical activity appearing at the location of the distal seed electrode 705 may be viewed external of the patient to determine if that is an appropriate location to implant the seed 220.

By way of example, the main lumen 712 of the seed delivery catheter 615 may have an internal diameter of about two-and-a-half millimeters, and the seed delivery catheter 615 may have an outside diameter that is slightly larger than that. In this case, the seed body 702 may have a width of about two millimeters, and the length of the seed body 702 may be about five to ten millimeters, for example. This enables the seed 220 to be implanted entirely within a myocardial wall 605, which may, for example, be about 20 millimeters thick in the left ventricle.

The seed 220 has a pair of forward-end tines 715 and 720 that each extend from a common junction point 725. Each of the tines 715 and 720 may be about three to eight millimeters in length, for example. The seed body 702 also has a central bore 730 extending longitudinally through a center of the seed body 702. In FIG. 7, which shows the seed 220 not yet implanted, one of the forward-end tines, namely tine 720, extends proximally into the bore 730, while the other forward-end tine 715 extends distally to enable it to pierce through tissue. As will be described in more detail later, the junction point 725 for the tines 715 and 720 may be pushed forward of the seed 220 body, and when the constrained tine 720 clears the central bore 730, the tines 720 and 715 are biased to snap into a lateral configuration that will be shown in a later figure. The junction point 725 is physically larger than the diameter of the central bore 730, and thus enables the seed 220 to be pulled in a proximal direction by pulling on extraction wire 735.

The seed extraction wire 735 is attached to the junction point 725, and extends proximally through the entire length of the seed central bore 730, and from there continues proximally through the delivery catheter 615 and outside the body (not shown in FIG. 7). The wire 735 may be made of an electrically conductive material so as to sense an electrical signal appearing at a distal end of the wire 735, thus serving as an extraction pull wire and as a temporary ECG lead for distal electrode 705. This is a means of sensing a bipolar electrocardiogram at a proposed implantation site before permanently implanting the seed 220, using electrode 705 (with wire lead 735) as a first electrode, and using the catheter electrode 625 and lead 716 as a second electrode.

In that the extraction wire 735 extends outside the patient's body, a physician may pull the wire 735, and given that the junction point 725 is too large to be pulled into the seed body central bore 730, pulling the wire 735 pulls the seed 220 proximally within the delivery catheter 615. The extraction wire 735 is also constructed of a material and of a diameter such that the wire 735 is rigid enough to be pushed forward to extend the junction point 725 forward of the seed 220 body and hence free the forward-end tine 720 from the constraining central bore 730. The wire 735 has stopper device 740 that is attached to the wire 735 at a point that is proximal of the seed 220 body. The stopper device 740, like the junction point 725, is larger than the seed body central bore 730, and thus constrains how far the lead junction point 725 can be extended forward of the seed body 702. The stopper device 740 is positioned on the wire 735 at a location that is far enough away from the rear-end of the seed body 702 such that wire 735 may be pushed distally far enough to free the constrained tine 720 from the seed body central bore 730.

The extraction wire 735 has a detachment mechanism 745 located on the wire 735 at a point that is immediately distal of the stopper device 740. The detachment mechanism 745 may be activated by a physician to detach the portion of wire 735 that is proximal of the detachment mechanism 745. Various detachment mechanisms may be used for the detachment mechanism 745. For example, the detachment mechanism 745 may be a high-resistance portion of a conductive line that extends proximally to a point external of the patient, and that can be heated and detached by injecting current of a specified amount into the conductive line. In this case the wire 735 may serve three purposes: extraction of a seed 220 from a location that does not provide optimal cardiac resynchronization; conduction of the tip electrode 705 ECG signal to a recorder outside the body; conduction of a burst of current to detach itself at a point 745 of relatively high electrical resistance. Another example for the detachment mechanism 745 is a mechanical configuration where the proximal detachable portion of the lead 735 may be unscrewed from the remainder of the lead 735, or where the lead 735 is pushed and turned in a certain way to effect detachment of the proximal portion from the remainder of the lead 735. A mechanical skiving or shearing means (not shown) may alternatively be applied at point 745.

The seed 220 also has a pair of tines 750 and 755 that extend from the rear end of the seed body 702. In the shown example, there are two such tines 750 and 755, though it will be understood that there may be more than two tines, or a single tine. The tines 750 and 755 assist in securing the seed 220 at a desired location within the tissue, such as within a desired location of the myocardial wall 605, to prevent the seed from migrating under the repeated stress of heart muscle contraction. The tines 750 and 755, in this example, are attached to the rear-end electrode 710 near a periphery of the electrode 710, and extend from their attachment points in a direction that is about 45 degrees from a longitudinal axis of the seed body 702. As shown in FIG. 7, however, far ends of the tines 750 and 755 are constrained by an outer wall of the catheter lumen 712, and become bent toward the longitudinal axis of the catheter 615. When the seed 220 is pushed out of the distal end of catheter 615, the tines 750 and 755 spring outwardly into their normal position (not shown in FIG. 7).

A tube 760 that is movable longitudinally within the catheter 615 is used to push the seed 220 distally within the catheter 615 and out of the catheter distal opening 713. The tube has a lumen 765 extending longitudinally through its entire length so that the wire 735 extends through the tube lumen 765. The cross-sectional diameter of the pusher tube 760 may be, for example, about half that of the catheter lumen 712. As such, where the catheter lumen 712 diameter is about 2.5 mm, the tube cross-sectional diameter may be about 1.25 mm.

Figure 8:
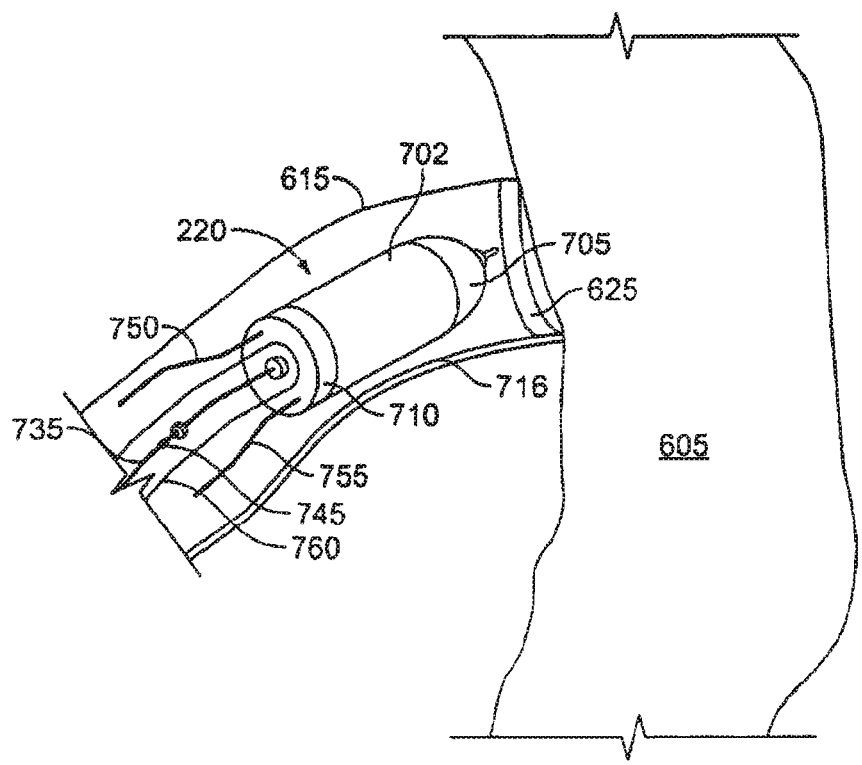
FIG. 8 is a diagram similar to FIG. 7, with a distal end of the delivery catheter pressed against a myocardial wall.

In FIG. 8, the seed delivery catheter 615, with a seed 220 contained within, is shown with its circular distal electrode 625 pressed against the myocardial wall 605. In the configuration shown, it is possible for the electrical activity occurring at that site of the myocardial wall 605 to be monitored at a proximal end of the lead 716 to determine if the site is an appropriate candidate site in which to implant the seed 220.

Turning now to FIG. 9, two seeds 220A and 220B are shown. The first seed 220A is shown during the process of implanting the seed 220A within the myocardial wall 605, with the assistance of the seed delivery catheter 615. The second seed 220B is shown as having already been permanently implanted within the myocardial wall 605.

The first seed 220A is shown as having been pushed nearly entirely within the myocardial wall 605. This was accomplished by the physician pushing the push tube 760 within the seed delivery catheter 615 so as to push the seed 220A out of the catheter's distal opening 713. The forwardly extending distal tine 715 served to pierce the myocardial wall 615 and permit implantation within the wall 615.

In the position shown in FIG. 9, the seed's rear-end tines 750A and 755A are still partially within the seed delivery catheter 615 and thus are still being constrained from extending outwardly from the seed body's longitudinal axis. As such, it is still possible for the physician to pull back the seed 220A from this position by pulling on the seed extraction wire 735A. If the seed 220A were to have been pushed a little further so that the proximal tines 750A and 755A become extended, then it may not be possible to pull back the seed 220A. As discussed previously, seed 220A may be charged and commanded to discharge while wire 735 serves as a lead to monitor the electrical activity at the forward end of the seed 220A. The physician may determine that the present positioning is not appropriate, and wire 735 may then be pulled to extract the seed, which may then be moved to an alternate location.

Also in the position shown in FIG. 9, the wire 735 has not yet been pushed forward to deploy the distal tines 715A and 720A (750A not shown in FIG. 9). Deploying the distal tines 715A and 720A is done as follows. First, the pushing tube 760 is used to push the seed 220A so that, firstly, the proximal tines 750A and 755A are freed from the delivery catheter 615 and thus extend outwardly, and secondly, the seed's distal tine junction point 725A extends distally of the seed, and preferably entirely through the myocardial wall 605. In particular, the junction point 725A and one of the forward-end tines 715 are both positioned outside the myocardial wall 605 in FIG. 9. Next, the wire 735A is pushed distally until the lead stopper device 740 becomes flush with the proximal seed electrode 710A. When this occurs, the constrained tine 720A becomes removed from the seed body central bore, thus allowing the two distal tines 715A and 720A to pop into the lateral position. Seed 220B is shown in the deployed position, the proximal tines 750B and 755B are shown extended, and the two distal tines 715B and 720B are outside the myocardial wall 605 and extend laterally from the junction point 725B.

Figure 10:
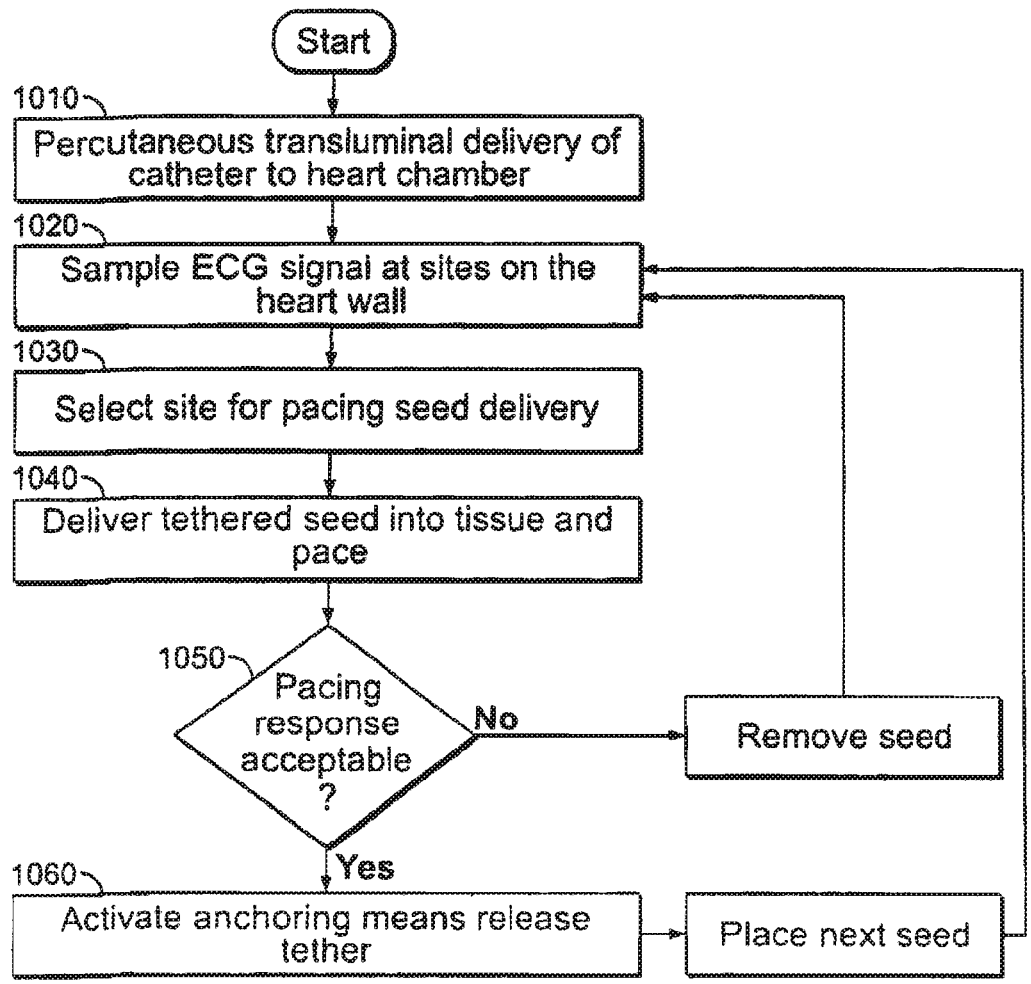
FIG. 10 is a flow chart of a method for delivering and implanting wireless electrode assemblies.

Referring now to FIG. 10, a flowchart is shown that describes a method of delivering a seed 220 using the catheter 615 or another similar delivery device. The method begins at step 1010 with the percutaneous transluminal delivery of the catheter 615 to the heart chamber. This may be accomplished in the following manner. First, an introducer is used to provide entry into, for example, the femoral vein or artery (depending on where the seed 220 is to be delivered). The catheter 615 is then inserted so that its distal end is snaked through the inferior vena cava and into the right atrium, for example. Thus, a seed 220 may be delivered in the right atrium. The distal end of the catheter 615 may also be moved from the right atrium, through the tricuspid valve, and into the right ventricle, for delivery of a seed 220 there. The distal end of the catheter may also be pushed through the fossa ovalis, accessed on the right atrial septum, for placement of seeds 220 in the left heart chambers. Alternatively, the distal end of the catheter 615 may be snaked through the femoral artery and descending aorta, through the aortic valve and into the left ventricle, and from the left ventricle may be moved through the mitral valve into the left atrium. Navigating the catheter 615 may require that the catheter 615 have some type of navigational capability such as push and pull wires commonly used with electrophysiology catheters.

Next, at step 1020, a sample ECG signal may be taken at sites on the heart inner wall. This may be done with the catheter 615 positioned as shown in FIG. 8, for example. At step 1030, the physician selects a site at which to deliver the seed 220. Then, at step 1040, the physician delivers the seed 220 into the myocardial wall tissue, such as shown with seed 220A in FIG. 9. At this point, the seed 220 is still tethered by the lead 735A so that the seed may be pulled back into the delivery catheter 615 if necessary. Further at step 1040 a test pace is performed to test the response at this site. This may be done using the programmer 270 shown in FIG. 6 to instruct the controller/transmitter device 240 to send a charging signal and then a trigger signal to the particular seed 220.

If the pacing response is found, at step 1050, to be unacceptable, then the seed 220 may be removed and the process may be performed again starting at step 1020. If, on the other hand, the pacing response is found to be acceptable, then, at step 1060, the anchoring means for the seed 220 may be activated, for example, by moving the seed 220 entirely out of the catheter 615 and freeing the proximal tines 750 and 755 from the constraints of the catheter 615 and pushing the lead 735 to release the distal tines 715 and 720. Also at step 1060, the tether to the seed 220 may be released, for example, using the detachment mechanism 745. Having completed the implantation of the seed, it is now possible at step 1070 to begin placement of the next seed 220.

As discussed previously, each of the seeds 220 may have a filter 425 (see FIG. 4) that allows passage of a signal of a particular frequency. Thus, for example, where eight seeds 220 are implanted, each of the seeds 220 may have a band pass filter 425 of a different center frequency. To make this possible, seeds 220 may be manufactured as having one of sixteen different band pass frequencies. Thus, up to sixteen seeds 220 may be implanted so that each seed is separately controllable. A code for the particular pass frequency may be labeled directly on the seed 220 itself, or alternatively, may be labeled on the packaging for the seed 220. As such, when programming the system 200 using the programmer 270, the particular band pass frequency for each seed 220 is communicated to the pacing controller 240.

Figure 11A:
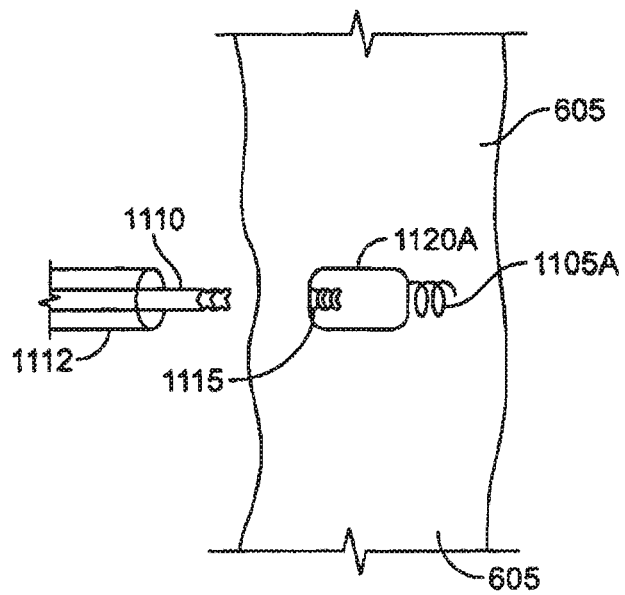
FIGS. 11A-11D are diagrams of alternative embodiments of wireless electrode assemblies and associated delivery catheters, with the wireless electrode assemblies shown being implanted within a myocardial wall.
Figure 11B:
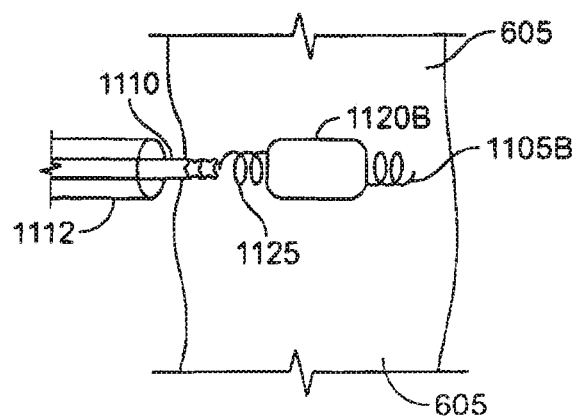
Figure 11C:
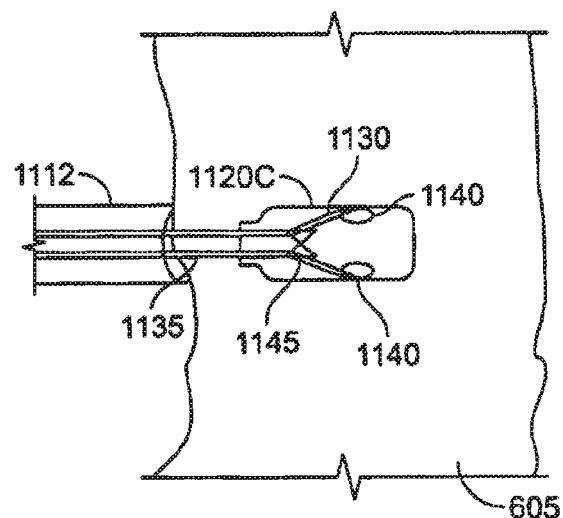
Figure 11D:
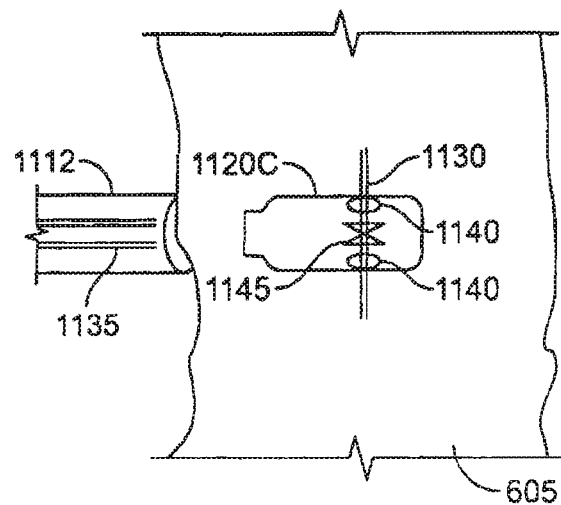

A variety of alternative embodiments are envisioned for seed delivery and detachment. For example, FIG. 11A shows a seed 1120A that is secured into the myocardium 605 with a distal spring 1105A, or "cork screw." A delivery rod 1110 provided by a delivery catheter 1112 is detached from the seed 1120A by turning the rod 1110 to engage the spring into tissue and also unscrew the threaded distal rod section 1115 from the seed 1120A. In FIG. 11B, a distal spring 1105B is screwed into the myocardium 605 using a clockwise rotation of the seed 1120B, which also unscrews the delivery rod from the seed. Upon removal of the delivery rod, proximal spring 1125 is exposed to the myocardium 605. Clockwise spring 1105B and counter-clockwise spring 1125 together prevent rotation and translation of the seed through the myocardium. A mechanism for release of the springs is not shown in the figure. A small push rod passing through the delivery rod and seed could be used to push the distal spring from the seed and into a locked position. A thin sheath could cover proximal spring 1125. The thin sheath would be retracted along with the delivery rod. Alternate means for detachment of the delivery rod include Ohmic heating of a high resistance portion of the rod, and mechanical shearing. In FIG. 11C-D, tines 1130 are pushed, using a push rod 1135 provided through the main lumen of the delivery catheter 1112, from the central portion of the seed 1120C, out through channels 1140 and into the myocardium 605, so that the tines 1130 extend laterally from the seed 1120C body (as shown in FIG. 11D), and so that the seed 1120C becomes secured within the tissue. The push rod 1135 is removable, at an attachment point, from a proximal end junction point 1145 of the tines 1130. Various mechanisms for removing, or detaching the push rod 1135 from the tine proximal end junction point 1145 may be employed, as discussed previously in connection with the FIG. 7 embodiment.

Referring now to FIGS. 11E-K, some embodiments that are envisioned for seed delivery and detachment include a seed 1120E having a helical tine 1105E and one or more adjustable tines 1110E that secure the seed 1120E to the myocardium 605. In such embodiments, detachment mechanisms 1145E and 1165E may be used to release the seed 1120E from an elongate shaft 1160E after the seed 1120E is secured to the myocardium 605.

Figure 11E:
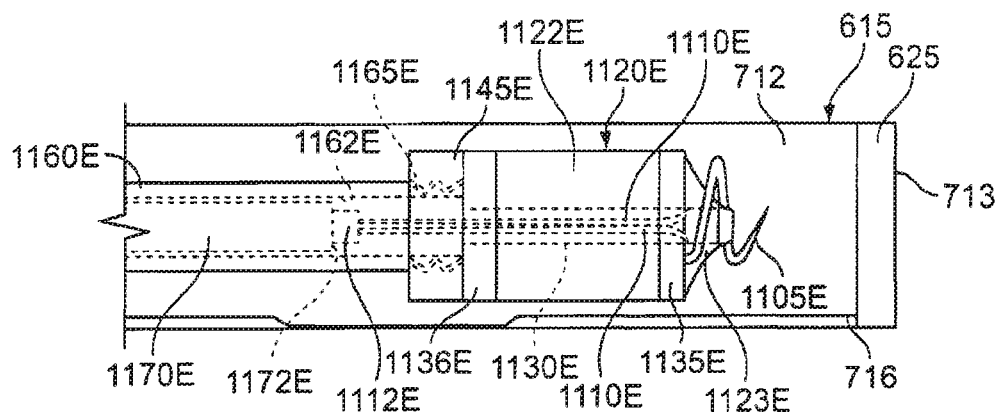
FIGS. 11E-11W are diagrams of alternative embodiments of wireless electrode assemblies and associated delivery catheters.

Referring to FIG. 11E, the seed 1120E is shown within a distal portion of the seed delivery catheter 615. The seed 1120E has a main body 1122E that, in this example, is cylindrically shaped with a tip portion 1123E at a distal end. The seed 1120E may include two bipolar electrodes 1135E and 1136E that are capable of discharging an electrical pulse. Electrode 1135E is located at the distal end of seed body 1122E, and the other electrode 1136E is located at a proximal end of the seed body 1122E. In this embodiment, the tip portion 1123E of the seed body 1122E has a modified cone shape that facilitates delivery of the distal end of the seed 1120E into tissue such as the myocardial wall 605, as will be illustrated in later figures. The tip portion 1123E may serve as a strain relief mechanism for the adjustable tines 1110E that extend from the tip portion 1123E. Furthermore, the tip portion 1123E may also deliver a steroid elution to minimize the formation of fibrous tissue at the seed/myocardium interface. While the distal and proximal electrodes 1135E and 1136E are shown on the seed body itself, other locations are possible. For example, the distal electrode 1135E may be disposed at the end of the helical tine 1105E to achieve the maximum separation between electrodes, or may be an entire tine. In another example, the surface of tip portion 1123E on the seed body 1122E may function as the distal electrode 1135E, which may provide a more efficient use of space when the seed body 1122E is substantially smaller in size. Furthermore, using the surface of tip portion 1123E to function as the distal electrode 1135E may be desirable in circumstances where only the tip portion 1123E contacts the endocardium or myocardium tissue (described in more detail below).

As previously described, the seed delivery catheter 615 includes an elongate tube with a main lumen 712 extending though its entire length. The catheter 615 has an opening 713 at its distal end so that the seed 1120E may be released from the distal end of the delivery catheter 615. In some circumstances, all or a portion of the seed 1120E may extend from the delivery catheter 615 before the seed 1120E is secured to the heart tissue. In those cases, the main lumen 712 may still be sized to slidably engage the elongate shaft. The catheter 615 may also have an electrically conductive lead 716 and an electrode 625 that extends around the periphery of the distal opening 713 and is capable of providing local ECG information as previously described. In some embodiments, it may be necessary to secure the tip of the catheter 615 to the heart tissue during seed placement. For example, the distal end of the catheter 615 may include a screw mechanism to temporarily secure the catheter 615 to the heart tissue (described in more detain below in connection with FIG. 13).

In this embodiment, the seed 1120E has a plurality of adjustable tines 1110E that each extend from a common junction member 1112E. As shown in FIG. 11E, each of the adjustable tines 1110E generally extend from the junction member 1112E through a central bore 1130E of the seed body 1122E. FIG. 11E shows the seed 1120E not yet implanted, and only the helical tine 1105E extends from the seed body 1122E while the adjustable tines 1110E are disposed in the central bore 1130E. As will be described in more detail later, the junction member 1112E may be pushed in a distal direction by an actuation rod 1170E, thereby forcing the adjustable tines 1110E from the distal end of the central bore 1130E. When the constrained tines 1110E extend from the central bore 1130E, the tines 1110E are biased to extend in a curled or hook configuration. The junction member 1112E may be physically larger than the diameter of the central bore 1130E, providing a stopping point for actuation of the adjustable tines 1110E.

Still referring to FIG. 11E, the elongate shaft 1160E includes a detachment mechanism 1165E at a distal end that is capable of engaging/disengaging the detachment mechanism 1145E of the seed 1120E. In this embodiment, the detachment mechanism 1165E includes a threaded member that engages a complementary threaded member on the seed's detachment mechanism 1145E. The threaded engagement between the detachment mechanisms 1165E and 1145E may be arranged so that the threads would not release when the seed 1120E is being advanced into the tissue with the rotation of the helical tine 1105E.

From the detachment mechanism 1165E, the elongate shaft 1160E continues proximally through the delivery catheter 615 and outside the patient's body (not shown in FIG. 11E). In that the elongate shaft 1160E extends outside the patient's body, a physician may direct the seed body 1122E (via the elongate shaft 1160E coupled thereto) through the lumen 712 of the delivery catheter 615. (As described in more detail below in connection with FIG. 11I, the delivery catheter 615 may be navigated through an access catheter or other steerable sheath to the implantation site. The access catheter is capable of maintaining a stable valve crossing, which can reduce trauma to the valve and facilitate the implantation of multiple seeds into the wall of the heart chamber.) The elongate shaft 1160E may be constructed of a material and of a size and design such that the elongate shaft 1160E is sufficiently rigid to be rotated within the main lumen for purposes of engaging the helical tine 1105E with the myocardium tissue. Also, the elongate shaft 1160E may be sufficiently flexible so as to not impede navigation of the elongate shaft 1160E and the catheter 615 to the implantation site.

The actuation rod 1170E may be disposed in a lumen 1162E of the elongate shaft 1160E. The actuation rod 1170E includes an engagement surface 1172E that is adapted to contact the junction member 1112E. From the engagement surface 1172E, the actuation rod 1170E may continue proximally through the elongate shaft 1160E and outside the patient's body. In such embodiments, a physician may apply a force at the proximal end of the actuation rod 1170E so as to slide the rod 1170E within the elongate shaft 1160E. Such motion of the elongate rod 1170E may apply a distal force upon the junction member 1112E. The actuation rod 1170E may be constructed of a material and be of a size such that the actuation rod is sufficiently rigid to push against the junction member 1112E and force adjustable tines 1110E to extend from the distal end of the central bore 1130E. Also, the elongate rod 1170E may be sufficiently flexible so as to be guided through the lumen 1162E of the elongate shaft 1160E.

Figure 11F:
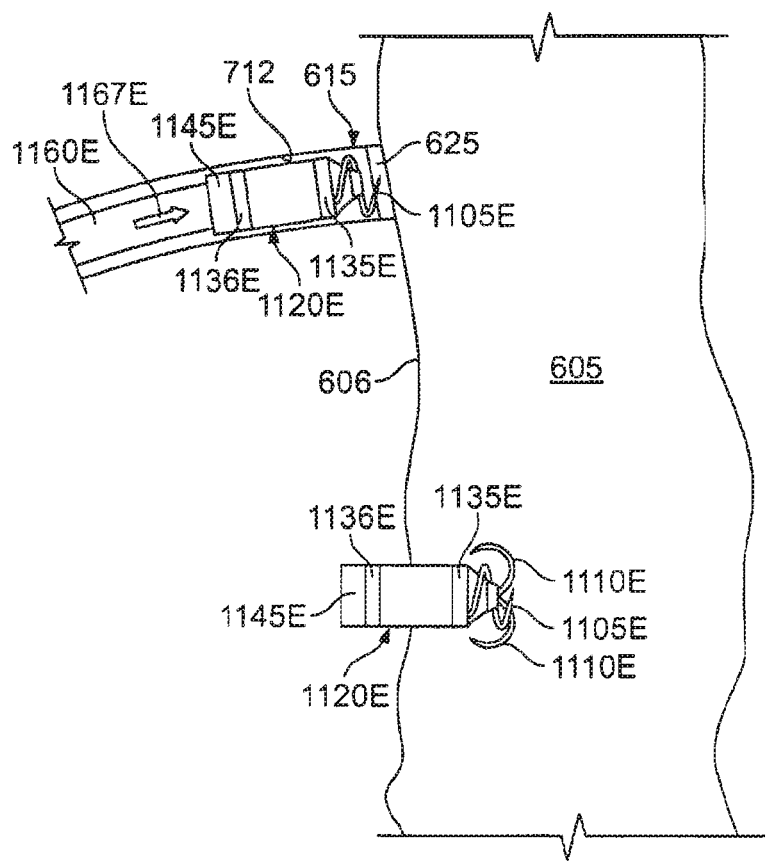
Figure 11G:
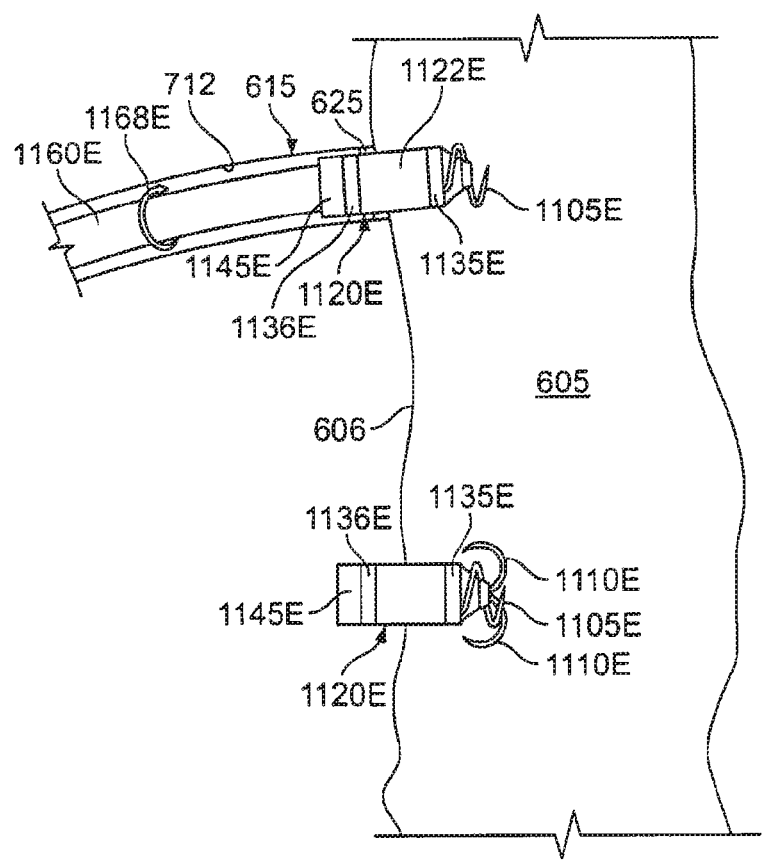
Figure 11H:
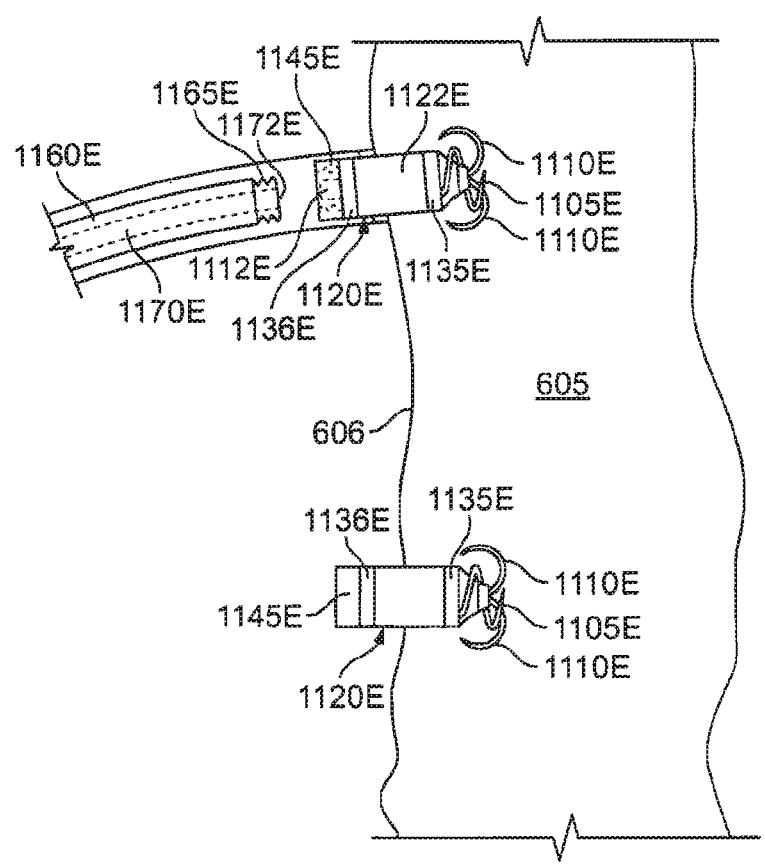

Referring now to FIGS. 11F-11H, at least a portion of the seed 1120E shown in FIG. 11E may be implanted into myocardium 605. As previously described in connection with FIG. 6, the delivery catheter 615 may be guided into a heart chamber (e.g., left atrium 32, left ventricle 34, right atrium 36, or right ventricle 38) to enable placement of at least a portion of the seed 1120E from the heart chamber into the myocardium 605. In such circumstances, the seed may pass necessarily from the distal opening 713 of the catheter 615, through an inner lining of the heart wall (e.g., the endocardium 606), and into the myocardium 605. FIGS. 11F-11H show a seed 1120E that is being implanted into the myocardium 605 and also show a neighboring seed 1120E (below the first seed 1120E) that was previously secured to the myocardium 605.

Referring to FIG. 11F, the seed 1120E in the lumen 712 of the delivery catheter 615 may be directed toward the distal end by a force 1167E from the elongate shaft 1160. The distal end of the delivery catheter 615 may abut (or be positioned proximate to) the inner surface of the heart chamber so that the seed 1120E is guided to a selected site of the heart wall. As shown in FIG. 11E, adjustable tines 1110E of the seed 1120E in the delivery catheter 615 are not in an actuated position where they extend from the distal end of the central bore 1130E (the adjustable tines 1110E of the neighboring seed 1120E that was previously implanted are shown in an actuated position). The helical tine 1105E is configured to penetrate through the endocardium 606 and into the myocardium 605, as described in more detail below.

Referring to FIG. 11G, the seed 1120E in the lumen 712 of the delivery catheter 615 may be rotated by a torsional force 1168E from the elongate shaft 1160. By rotating the seed body 1122E along its longitudinal axis, the helical tine 1105E may be "screwed" into the heart wall. In such circumstances, the helical tine 1105E penetrates through the endocardium 606 and into the myocardium 605. In some embodiments where the detachment mechanism 1145E includes a threaded member, the torsion force 1168E from the elongate shaft 1160E may serve to maintain or tighten the threaded engagement.

In the position shown in FIG. 11G, the seed's adjustable tines 1110E are not extended from the central bore 1130E (as shown by the neighboring seed). As such, it is still possible for the physician to pull back the seed 1110E from this position by rotating the elongate shaft 1160E in a direction opposite of force 1168E, which would cause the helical tine 1105E to "unscrew" from the myocardium tissue. The seed's distal electrode 1135E is in contact with the myocardium 605. As discussed previously, seed 1120E may be commanded to discharge a pacing electrical pulse while electrode 625 on the delivery catheter 615 monitors the electrical activity at the selected site. If the physician determines that the present positioning of the seed 1120E is not satisfactory, the seed 1120E may be retracted into the delivery catheter lumen 712, which may then be moved to an alternate location. At the alternate location, the helical tine 1105E would again penetrate through the endocardium and into the myocardium 605, in which case further monitoring of electrical activity may occur.

Referring to FIG. 11H, after the seed 1120E is secured to the heart wall (e.g., at least a portion of the helical tine 1105E and perhaps a portion of the seed body 1122E is penetrated into the endocardium) and after the physician determines that the positioning of the seed 1120E is proper, the adjustable tines 1110E may be forced to an actuated position. In this embodiment, the actuation rod 1170E disposed in the elongated shaft 1160E is capable of applying a force on the junction member 1112E. When the junction member 1112E is forced toward the seed body 1122E, the adjustable tines 1110E extend from the distal end of the central bore 1130E. In this embodiment, the adjustable tines 1110E are biased to have a curled or hook shape when unconstrained by the central bore 1130E. For example, the adjustable tines 1110E may comprise a shape memory alloy material, such as nitinol or the like, that is capable of returning to its biased shape after being elastically deformed within the central bore 1130E. The adjustable tines 1110E embed in the myocardium 605 to provide supplemental anchoring support and to substantially hinder additional rotation of the seed body 1122E. As such, the elongate shaft 1160E may be rotated backward relative to the seed body 1122E, which causes the threaded members of detachment mechanisms 1165E and 1145E to disengage one another. In this embodiment, the elongate shaft 1160E may be rotated relative to the seed body 1122E without extracting the seed 1120E from the myocardium 605 because the adjustable tines 1110E prevent the helical tine 1105E from being "unscrewed." After the seed 1120E is detached from the elongate shaft 1160E, the delivery catheter 615 and the elongate shaft 1160E may be withdrawn from the implantation site.

In addition to preventing the seed body 1122E from substantially rotating within the myocardium 605, the adjustable tines also reduce the likelihood of the seed body 1122E being pulled or torn from the heart wall. The seed 1120E may be exposed to various forces from the beating heart and the turbulence of the blood in the heart chambers. In some embodiments, the seed 1120E may be attached to the heart wall so that a threshold amount of pull force is required to remove the seed 1120E from the heart wall. Certain embodiments of seed 1120E may be secured to the heart wall such that a pull force of greater than 0.3 lbs. is required to remove the seed body 1122E from the heart wall. In some embodiments, the a seed 1120E may be secured to the heart wall such that a pull force of greater than 0.5 lbs., and preferably greater than 1.0 lbs., is required to remove the seed body 1122E from the heart wall.

In one example, several seeds 1120E were secured to the myocardium of a *Porcine* (pig) heart using the helical tine 1105E and three adjustable tines 1110E. The *Porcine* heart was delivered to a lab where a portion of it was removed by scalpel to reveal an internal heart chamber. Several seeds 1120E were secured to the *Porcine* heart wall from the internal heart chamber-first by rotating the helical tine 1105E into the myocardium and then by actuating the adjustable tines 1110E to a curled shape substantially within the myocardium tissue. Each of the seeds 1120E was secured to the heart wall such that a pull force of greater than 0.3 lbs. was required to remove the seed body 1122E from the heart wall, and in some instances, a pull force of greater than 1.0 lbs. was required.

Figure 11I:
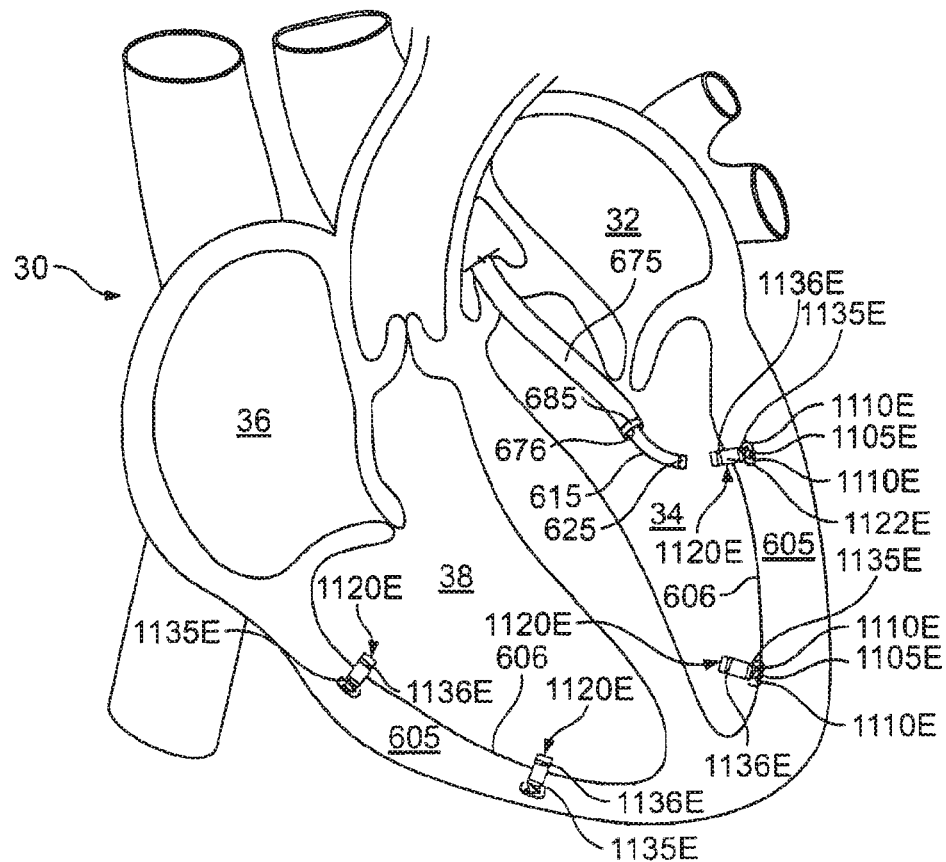

Referring now to FIG. 11I, helical tine 1105E and the adjustable tines 1110E may secure the seed 1120E to the myocardium 605 such that at least a portion of the seed body 1122E (e.g., the tip portion 1123E) penetrates into the myocardium 605. In some embodiments where the seed 1120E is substantially smaller than the myocardium wall thickness, the seed body 1122E may be fully inserted into the myocardium tissue. In the embodiments described in connection with FIGS. 11F-11H, a distal portion of the seed body 1122E extends into the myocardium 605 while a proximal portion of the seed body 1122E is exposed to the heart chamber (e.g., left atrium 32, left ventricle 34, right atrium 36, or right ventricle 38). As shown in those figures and in FIG. 11I, the seed body 1122E may be secured to the myocardium 605 so that the distal electrode 1135E is in contact with the myocardium while the proximal electrode 1136E is exposed to the heart chamber (and the blood therein). In certain cases, such positioning of the seed body 1122E may be dictated by a limited thickness in the myocardium wall.

Still referring to FIG. 11I, in some cases the seed body 1122E may not fully penetrate into the myocardium 605. For example, as shown by the lower seed 1120E secured in the left ventricle 34 shown in FIG. 11, a portion of the seed 1120E (e.g., the helical tine 1105E and the adjustable tines 1110E) may penetrate through the endocardium while the a substantial portion of the seed body 1122E does not fully penetrate into the myocardium tissue. In such circumstances, the tip portion 1123E may contact or penetrate into the endocardium (and perhaps partially into the myocardium), but the other portions of the seed body 1122E may not penetrate into the heart wall. Yet in this position, the seed 1120E may be capable of providing a pacing electrical pulse to the proximal heart tissue. The delivery of the pacing electrical pulse may be facilitated by using a surface of tip portion 1123E to function as the distal electrode 1135E.

In some cases, such positioning of the seed body 1122E may provide operational advantages. For example, if the distal electrode 1135E is a cathode that generally depolarizes nearby tissue cells, and if the proximal electrode 1136E is an anode that may hyper-polarize nearby tissue cells, the position of the seed body 1122E shown in FIGS. 11F-11I may reduce the effects of hyper-polarization. Because, in this example, the anode is generally exposed to blood in the heart chamber, the tissue cells in the myocardium are not necessarily hyper-polarized by the anode. In such circumstances, the pacing electrical charge between the cathode, the nearby myocardium, the nearby blood in the heart chamber, and the anode may reduce the hyper-polarization of local areas in the myocardium tissue-a factor that may limit pacing effectiveness.

Still referring to FIG. 11I, a distal end 676 of an access catheter 675 may be guided to a heart chamber where the seed 1120E is to be delivered. The access catheter 675 includes a lumen that extends from a proximal end to the distal end 676. The access catheter also includes a distal opening through which the delivery catheter 615 slidably passes as it is directed to the selected site proximal to the heart wall. In some embodiments, the access catheter 675 may be used to establish and maintain a valve crossing. In such circumstances, the delivery catheter 615 may be fully withdrawn from the patient's body after a first seed 1120E has been successfully implanted, yet the access catheter 675 can maintain its position in the heart chamber. Then, a new delivery catheter 615 and elongated shaft 1160E (with a second seed 1120E attached thereto) may be guided through the access catheter 675 are into the heart chamber. As shown in FIG. 11I, the access catheter 675 may approach the left ventricle 34 through the aorta (e.g., across the aortic valve and into the left ventricle 34). Other approaches are contemplated, depending on the targeted heart chamber, the conditions in the patient's heart vessels, the entry point into the patient's body, and other factors. For example, the access catheter 675 may approach the left ventricle 34 through the inferior vena cava, through a puncture in the atrial septum, and down through the mitral valve into the left ventricle 34.

As previously described, the delivery catheter 615 may include a steering mechanism, such as push or pull wires, to aid in placement of the distal end of the catheter 615 against a selected site on the wall of the heart. Similarly, the access catheter 675 may include a steering mechanism, such as push or pull wires, to aid in placement of the distal end 676 in the selected heart chamber. In this embodiment, the access catheter 675 includes an image device 685, such as an ultrasound probe or the like, proximal to the distal end 676 of the access catheter 675. The image device 685 is capable of providing the physician with visualization of the implantation site in the heart chamber. Because the inner surface of the heart chambers may be substantially irregular in surface topology as well as thickness, the image device 685 can be used by a physician to visualize the implantation site and possibly measure the myocardium wall thickness at that site. Such a feature may be particularly advantageous where the procedure is to be conducted on an active, beating heart.

Figure 11J:
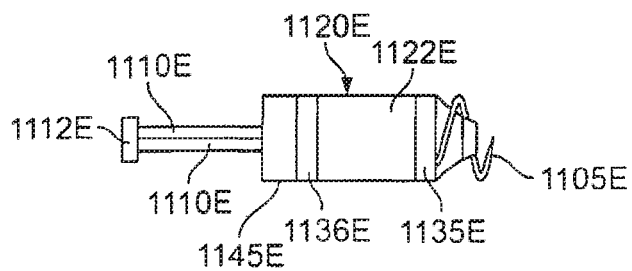
Figure 11J:
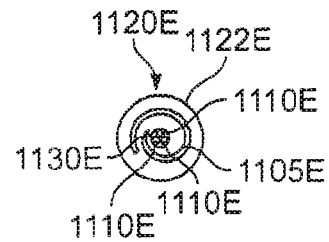
Figure 11K:
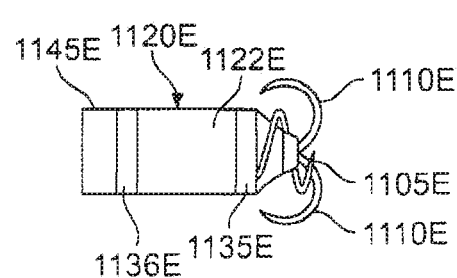
Figure 11K:
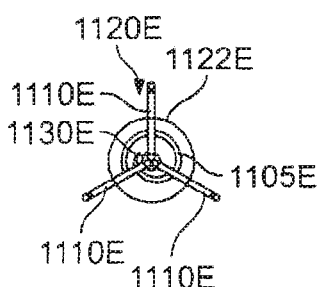

Referring now to FIGS. 11J-11K, the adjustable tines 1110E of the seed 1120E may be forced from a non-actuated position (e.g., FIG. 11J) to an actuated position (e.g., FIG. 11K). As previously described, the seed 1120E may include a plurality of adjustable tines 1110E. In this embodiment, the seed 1120E includes three adjustable tines 1110E that each extend from the common junction member 1112E. As shown in FIG. 11J, when the adjustable tines 1110E are in a non-actuated position, the junction member 1112E is offset from the seed body 1122E, and at least a portion of the adjustable tines 1110E are constrained in the central bore 1130E. When the junction member 1112E is forced in a generally distal direction toward the seed body 1122E, as shown in FIG. 11K, the adjustable tines 1110E are moved to an actuated position. As previously described, each of the tines 1110E may be biased to extend in a curled or hooked shape after being released from the central bore 1130E.

Figure 11L:
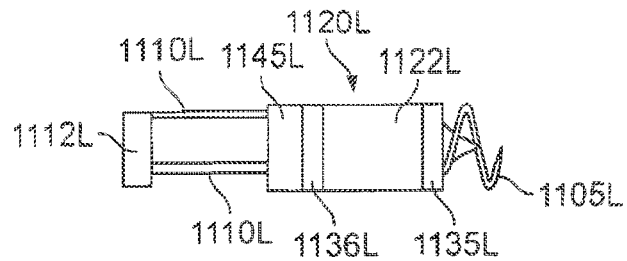
Figure 11L:
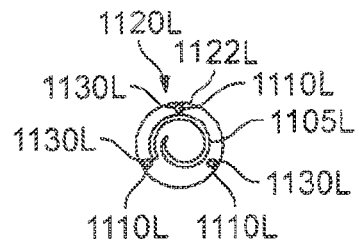
Figure 11M:
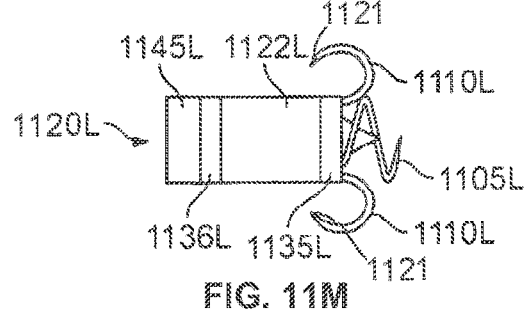
Figure 11M:
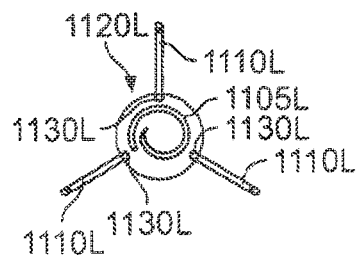
Figure 11N:
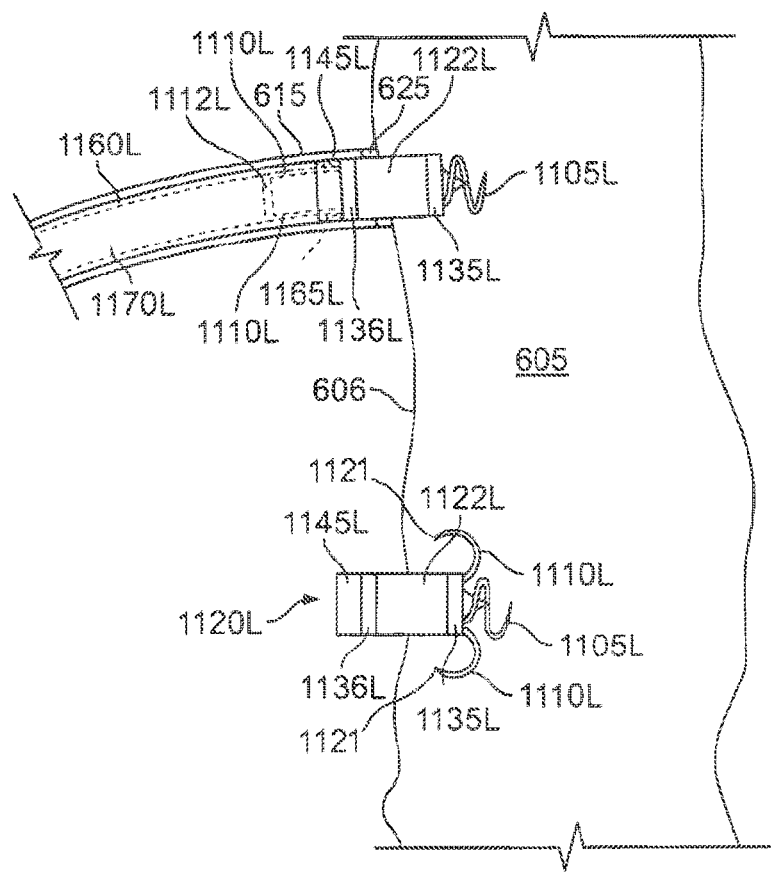

Referring now to FIGS. 11L-11N, alternate embodiments of the seed may include adjustable tines that are not disposed in a central bore of the seed body. For example, some embodiments of a seed 1120L may include a plurality of adjustable tines 1110L that are disposed in non-central bores 1130L that extend in a longitudinal direction near the periphery of the seed body 1122L. The adjustable tines 1110L of the seed 1120L may be forced from a non-actuated position (e.g., FIG. 11L) to an actuated position (e.g., FIG. 11M). In this embodiment, the seed 1120L includes a helical tine 1105L that extends distally from the seed body 1122L and includes three adjustable tines 1110L that each extend from a common junction member 1112L. As shown in FIGS. 11M and 11N, tines 1110L include a distal tip 1121. As shown in FIG. 11J, when the adjustable tines 1110L are in a non-actuated position, the junction member 1112L is offset from the seed body 1122L, and at least a portion of the adjustable tines 1110L are constrained in the associated peripheral bores 1130L. When the junction member 1112L is forced in a generally distal direction toward the seed body 1122L, as shown in FIG. 11K, the adjustable tines 1110L are moved to an actuated position. As previously described, each of the tines 1110L may be biased to extend in a curled or hook shape after being released from its associated bore 1130L. The tines 1110L may also extend from the sides of seed 1120L, such as through electrode 1135L, and could also operate to extend excitation signals from electrode 1135L into the tissue.

Referring to FIG. 11N, this embodiment of the seed 1120L may be directed to the targeted site of the heart wall using a delivery catheter 615 and an elongate shaft 1160L. The elongated shaft 1160L may include a detachment mechanism 1165L that engages/disengages with the seed 1120L. In this embodiment, the detachment mechanism 1165L includes a threaded member that engages a complementary threaded member of the seed's detachment mechanism 1145L. As previously described, the seed 1120L may be rotated such that the helical tine 1105L penetrates through the endocardium 606 and into the myocardium 605. When the seed 1120L is properly positioned, a force from an actuation rod 1170L may move the junction member 1112L in a distal direction toward the seed body 1122L. Such motion causes the adjustable tines 1110L to extend from the distal ends of the peripheral bores 1130L, thereby causing the adjustable tines 1110L and the helical tine 1105L to secure the seed 1120L to the myocardium 605. After the adjustable tines 1110L are moved to the actuated position, the elongate shaft 1160L may be rotated to release the seed 1120L at the detachment mechanisms 1145L and 1165L, which permits the delivery catheter 615 and the elongated shaft 1160L to be withdrawn from the implantation site.

Figure 11P:
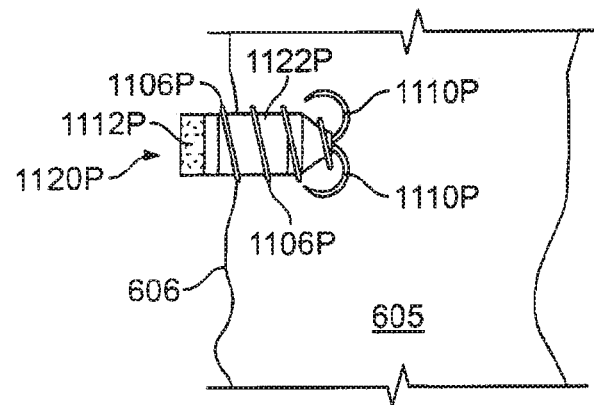

As previously described, the seed body may be secured to the heart tissue using tines, screws, barbs, hooks, or other fasteners. FIGS. 11P-11U illustrate further examples of such attachment mechanisms. Referring to FIG. 11P, some embodiments of a seed 1120P may include a body screw 1106P and adjustable tines 1110P to secure the seed 1120P to the myocardium 605. The body screw 1106P may include threads that are wound around the seed body 1122P so that rotation of the seed body 1122P causes that penetration through the endocardium 606 and into the myocardium 605. The threads may be interrupted and twisted in some circumstances to help ensure that the seed 1120P does not back out of the tissue.

Figure 11Q:
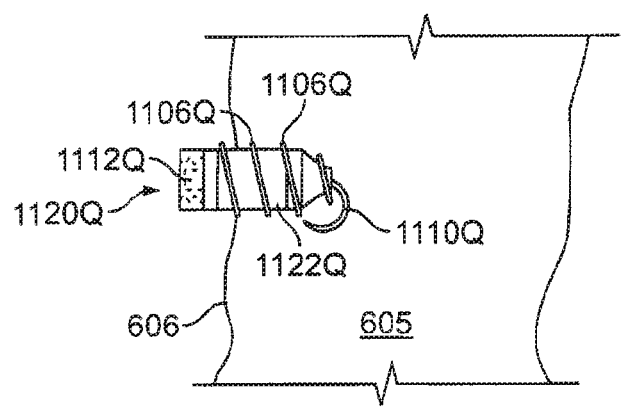

The adjustable tines 1110P may be actuated when a junction member 1112P is moved in a distal direction toward the seed body 1122P. Referring to FIG. 11Q, some embodiments of a seed may include a single adjustable tine that helps to secure the seed to the myocardium 605. For example, the seed 1120Q may include a body screw 1106Q and an adjustable tine 1110Q that is actuated by moving a junction member 1112Q toward the seed body 1122Q.

The embodiment of FIGS. 11P-11Q may provide additional benefits to advancing the seed 1120P into tissue. By providing a more tapered end on the seed body 1122P and connecting the body screw 1106Q to the seed body 1122P, the seed 1120P may create an opening for the passage of the seed body 1122P more easily into the tissue. In some cases where the body screw 1106Q is not used, the distal portion of the helical tine can pass into the heart wall tissue, but further progress may be blocked when the seed body 1122P abuts the tissue. Also, while the thread is shown in FIGS. 11P-11Q as being disposed tight to the seed body 1122P, it could also be separated slightly from the seed body 1122P, particularly around the front tapered portion of the seed body 1122P, and then connected back to the seed body 1122P, for example, by a thin webbed section that can itself cut into the tissue. While it is not necessary for all embodiments that the seed body be placed into the tissue, other appropriate arrangements may be used that allow the seed body 1122 to enter into the tissue without significant disruption to the physical structure of the tissue.

Figure 11R:
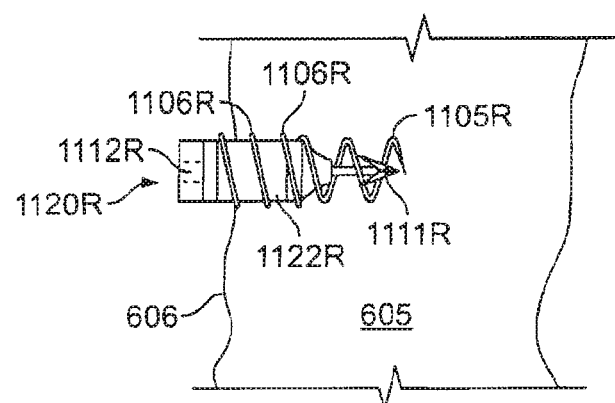
Figure 11S:
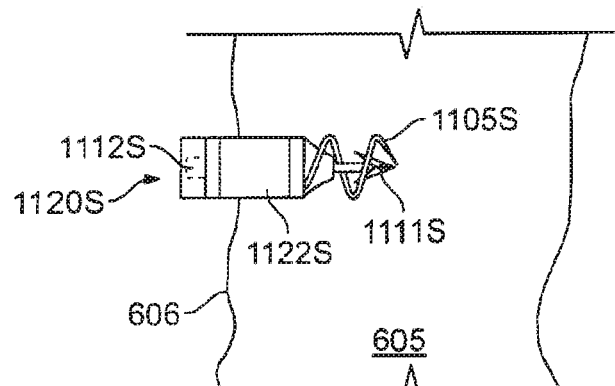
Figure 11T:
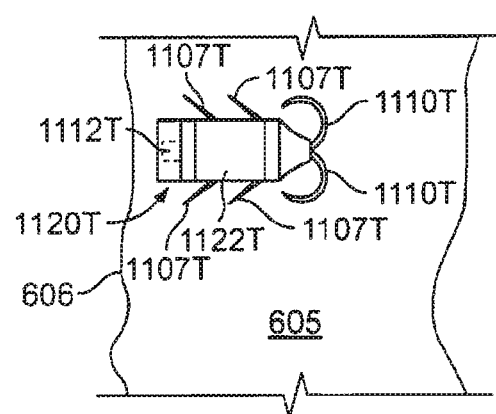
Figure 11U:
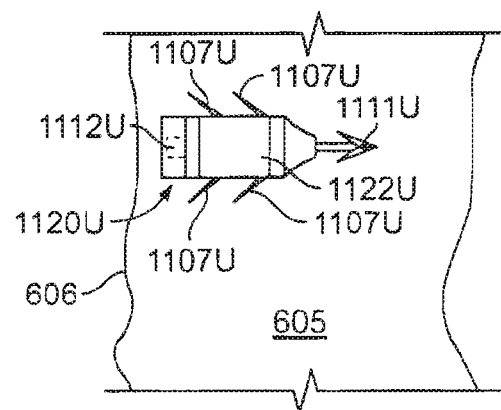

Referring to FIG. 11R, some embodiments of a seed may include an adjustable barb that helps to secure the seed to the myocardium 605. The adjustable barb may include biased extensions that outwardly shift when no longer constrained in a bore. For example, the seed 1120R may include a body screw 1106R that transitions into a helical tine 1105R and an adjustable barb 1111R that is actuated by moving a junction member 1112R toward the seed body 1122R. Referring to FIG. 11S, some embodiments of a seed 1120S may include a helical tine 1105S and an adjustable barb 1111S to secure the seed 1120S to the myocardium 605. The adjustable barb 1111S may be actuated by moving a junction member 1112S toward the seed body 1122S. Referring to FIG. 11T, some embodiments of a seed may include one or more body barbs 1107T that help to secure the seed to the myocardium 605. The body barbs 1107T may extend from the seed body 1122T and acts as hooks that prevent the retraction from the myocardium 605. For example, the seed 1120T may be fully embedded in the myocardium 605 and include body barbs 1107T and adjustable tines 1110T that can be actuated by moving a junction member 1112T toward the seed body 1122T. Referring to FIG. 11U, some embodiments of a seed 1120U may include body barbs 1107U and an adjustable barb 1111U to secure the seed 1120U to the myocardium 605. The adjustable barb 1111U may be actuated by moving a junction member 1112U toward the seed body 1122U.

Figure 11V:
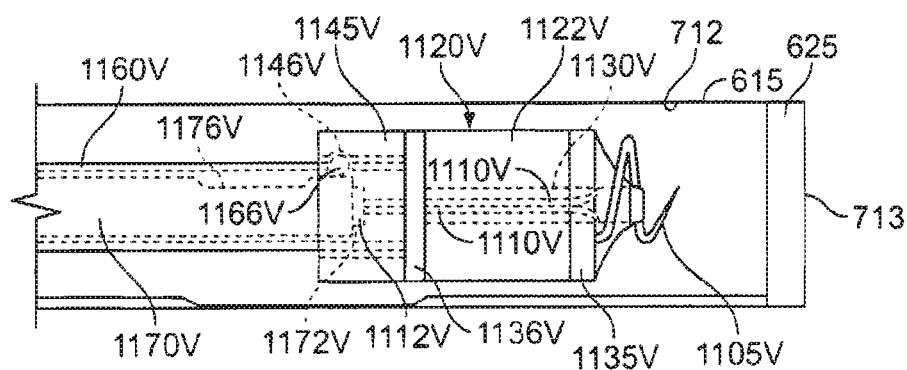
Figure 11W:
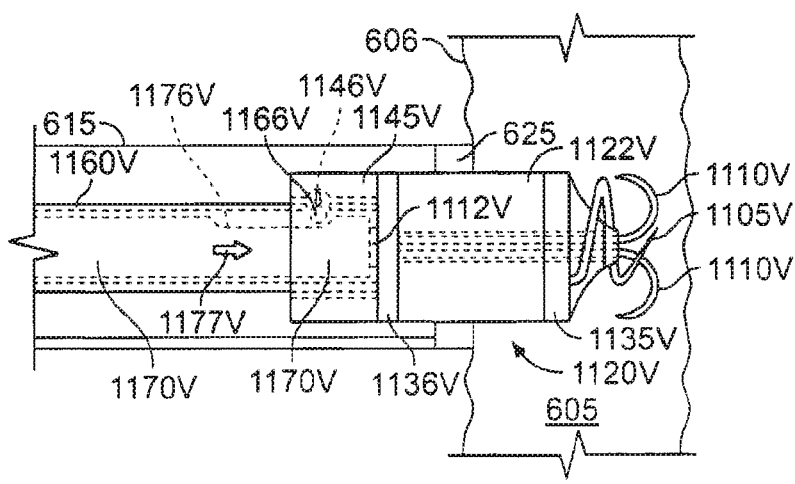

Referring now to FIGS. 11V-11W, some embodiments of the detachment mechanism between the elongate shaft and the seed may include a locking member that is movable between an engaged position (e.g., FIG. 11V) and a disengaged position (e.g., FIG. 11W). In such embodiments, the elongate shaft may have a noncircular outer cross-section (such as a square or hexagonal cross-sectional outer shape) to facilitate translation of rotational motion to the seed body.

Referring to FIG. 11V, the seed 1120V may include a body 1122V and electrodes 1135V and 1136V, as described in previous embodiments. Furthermore, the seed 1120V may include tines, screws, barbs, hooks, or other fasteners (such as a helical tine 1105V, adjustable tines 1110V that extend from a common junction member 1112V) as previously described. Also as previously described, the seed 1120V may be directed by an elongated shaft 1160V through a lumen 712 of a delivery catheter 615. The seed 1120V may include a detachment mechanism 1145V having a cavity 1146V shaped to receive at least a portion of a locking member 1166V. In the depicted embodiment, the cavity 1146V may be curved to fit a spherically shaped locking member 1166V like a small ball such that, when the locking member 1166V is engaged with the cavity 1146V, the elongate shaft 1160V is not retractable from the seed body 1122V.

Referring to FIG. 11W, when at least a portion of the seed 1120V is properly positioned in the myocardium 605, a force 1177V may be applied from the actuation rod 1170V may be to move the junction member 1112V toward the seed body 1122V. Such motion of the junction member 1112V may cause the adjustable tines 1110V to extend from the seed body 1122V, thereby securing the seed 1120V to the myocardium 605. In addition, the motion of the actuation rod 1170V may cause the locking member to move to a disengaged position. For example, the actuation rod 1170V may include a depressed surface 1176V that is substantially aligned with the locking member 1166V when the actuation rod 1170V forces the junction member 1112V to actuate the tines 1110V. As such, the locking member 1166V moves toward the depressed surface 1176V and disengages with the cavity 1146V. This disengagement permits the actuation rod 1170V, the elongate shaft 1160V, and the delivery catheter 615 to be withdrawn from the seed implantation site while at least a portion of the seed 1120V remains secured to the myocardium 605.

Detachment mechanisms other than those discussed above may also be used in appropriate situations. For example, multiple spherically shaped locking members like that discussed above may be attached along the length of a wire, such as by soldering. The wire may be passed down an interior passage of multiple seeds that are mounted end-to-end on the tip of a catheter. Each locking member may be located so as to extend out of a central bore inside the seeds to lock against a corresponding cavity on an internal surface of a seed. In operation, and with locking member holding each seed in place, the most distal seed may be driven into the tissue by rotating the seeds. The wire may then be withdrawn proximally the length of one seed, so that the locking member in the most distal seed is pulled back to the second-most-distal seed, and the other locking members move back one seed. Such a controlled withdrawal of the wire may be accomplished, for example, using an indexed trigger mechanism that is handled by the surgeon. The second seed-now the most distal seed—may then be implanted, and the wire withdrawn again. In such a manner, multiple seeds may be implanted from a single introduction of the mechanism into a heart chamber.

In addition, the seeds may be provided with alternative mechanisms for removal, such as for use when the primary attachment mechanisms are damaged, occluded, or otherwise unavailable. For example, several channels may be formed about the periphery of a proximal, nonimplanted electrode. The channels may proceed from shallow to deep so that, for example, a tool having radially-arranged fingers with inward extensions may position those extensions around the electrode. The fingers can then be contracted, such as by a sleeve that is slid down around the exterior of the fingers, and the extensions may be received into the channels. The tool may then be rotated so that the extensions move down into the deep portions of the channels and engage the seed in rotation so that the seed may be removed from the tissue.

Figure 12:
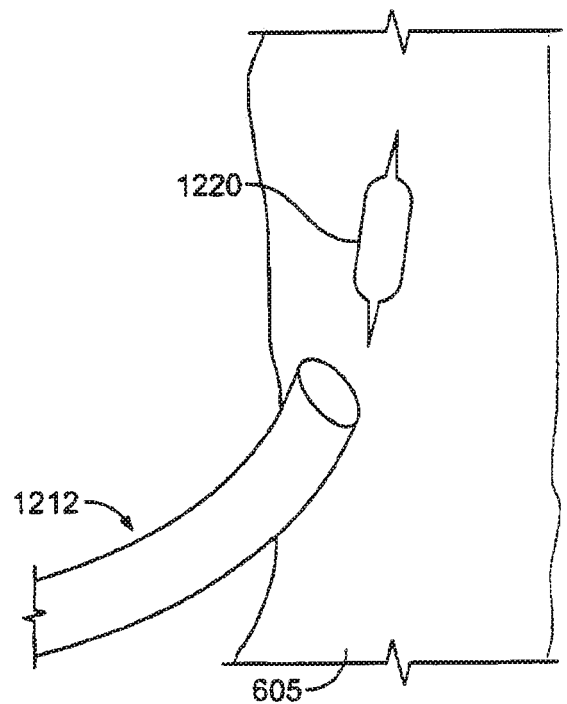
FIG. 12 is a diagram of a wireless electrode assembly and associated delivery catheter, with the wireless electrode assembly shown implanted within a myocardial wall in a position such that its longitudinal axis is parallel with the myocardial wall.
Figure 13:
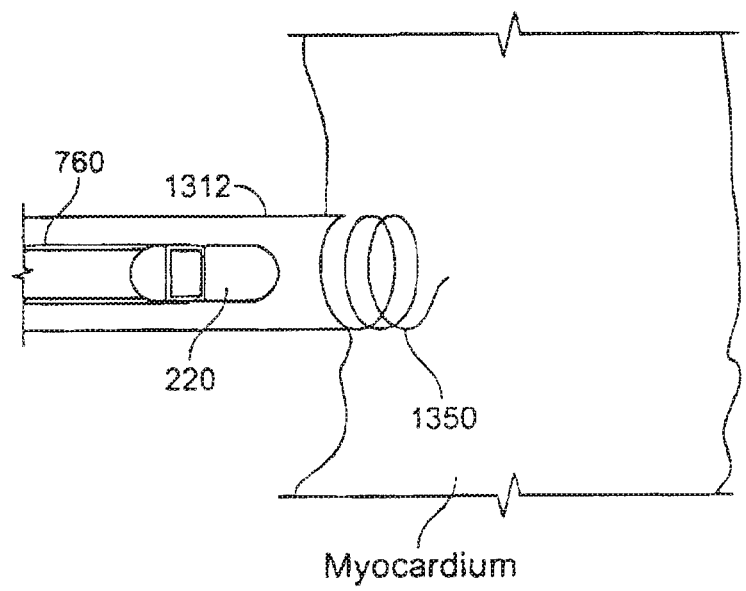
FIG. 13 is a diagram of a wireless electrode assembly and an another embodiment of an associated delivery catheter.

FIG. 12 illustrates the possibility that seeds 1220 may be placed parallel to the heart wall 605, in addition or in preference to transverse placement. This may be particularly necessary where the heart wall is thin, for example in the atria or in regions of the ventricles that contain scar tissue. Placement parallel to the wall is particularly required when the wall thickness is less than the seed length. Note that the catheter 1212 may be curved near its tip to facilitate parallel placement. Since the heart wall 605 is moving during the cardiac cycle, it may be necessary to secure the tip of the catheter 1212 to the heart tissue during seed placement. This concept is illustrated in FIG. 13, showing a cork screw 1350 temporary securement of the catheter 1312 to the wall 605. Tines that extend from the distal end of the catheter for penetration into the heart wall to secure and stabilize the catheter tip during seed delivery are also envisioned. The tines would be extended into the heart wall before seed placement, and retracted from the heart wall after seed placement.

Figure 14A:
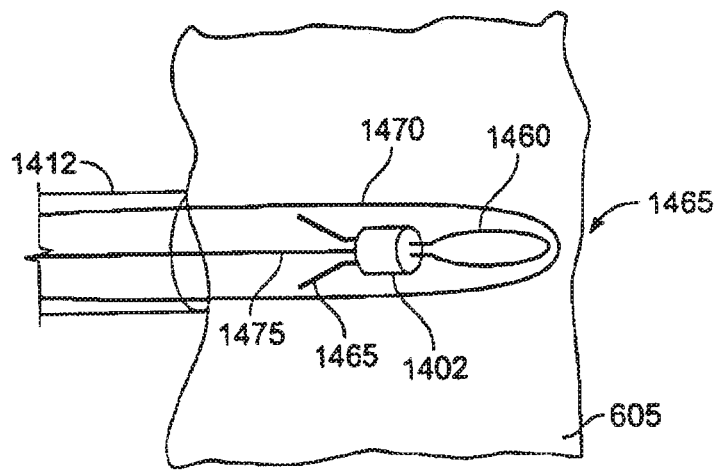
FIGS. 14A and 14B are diagrams of an alternative embodiment of a wireless electrode assembly and associated delivery catheter, with the wireless electrode assembly being shown being implanted within a myocardial wall.
Figure 14B:
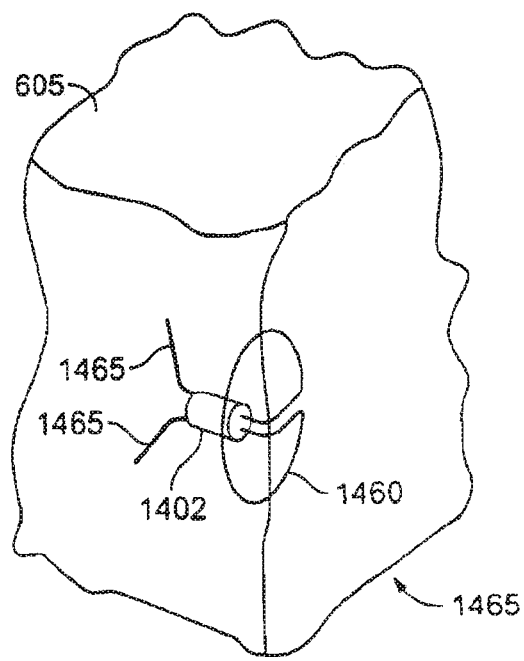

FIGS. 14A and 14B show a seed embodiment in which a seed pick-up coil 1460 also serves the function as a distal attachment, extending into the epicardial space 1465. The seed includes a seed body 1402, the distally extending coil 1460 and proximal tines 1465. The coil 1460 is wrapped down in a delivery tube 1470 provided by a catheter 1412, and expands to its full diameter after being pushed into the epicardial space 1465. The seed is pushed using a push rod, or wire, 1475 that operates to push the coil 1460 from the distal opening in the delivery tube 1470 and into the epicardial space. The seed body 1402 and proximal tines remain within the heart wall 605. The expanded coil 1460 has the advantage of collecting more magnetic flux by virtue of its larger diameter, leading to better coupling to the antenna, and a more efficient pacing system. The seed in FIGS. 14A-B can have a reduced diameter because it does not contain a relatively bulky coil. The seed body 1402 contains the capacitor and electronic components indicated in the schematic of FIG. 4. Proximal tines 1465 are shown attached to the seed for additional securement.

It is noted again, that it may be desirable to achieve maximum spacing between the proximal and distal electrodes to ensure conduction through the maximum volume of refractory tissue. For example, it may be possible for the bullet shaped seed of FIG. 4 to become encapsulated in fibrous, non-refractory tissue. In this case, the current density in tissue surrounding the fibrous capsule may be too low to cause depolarization. A solution to this problem is to use the furthest extremities of the seed as electrodes. For example, tines 715, 720, 750 and 755 (see FIG. 7) may be plated with a suitable conductive material to serve as electrodes that extend into the epicardial space. Current passing between the distal tines and the proximal seed electrode would then pass through refractory tissues. As a further precaution, the proximal tines 750 and 755 could be plated with a conductive material and serve as an extension of proximal electrode 710. Current passing between distal and proximal tines would encounter refractory tissues with a high degree of probability. Similarly, the epicardial coil 1460 of FIG. 14 may contain a central conducting coil surrounded by an electrical insulator, which is in turn coated with a conductive electrode material.

Figure 15:
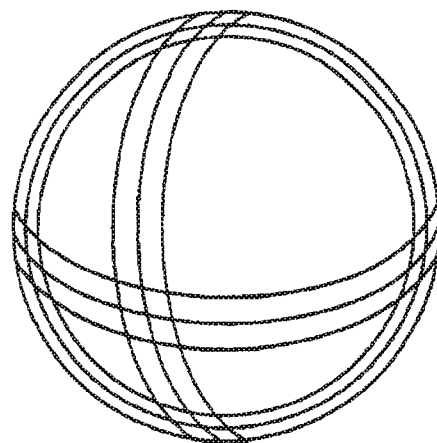
FIG. 15 is a diagram of an alternative embodiment of a coil for a wireless electrode assembly in which three orthogonal coils are wound on a single substrate.

For completeness, shown in FIG. 15 is an alternative seed coil embodiment in which three orthogonal coils are wound on a single substrate. The substrate may be made from a permeable material. Currents induced in each of the three coils would be rectified, and passed to a single capacitor. In this embodiment, the orientation of the seed relative to the transmit antenna is immaterial. This is important because there is no coupling between a coil having its axis parallel to the plane of the antenna, and it may not always be possible to implant a seed with its axis perpendicular to the plane of the antenna. The seed of FIG. 15 collects magnetic flux in each of three orthogonal directions, so that maximum flux is collected independent of the orientation of the incident magnetic field.

The electrical parameters in the seed circuit of FIG. 4, and the geometry of the antenna 260 of FIG. 6 may be optimized by the use of a computer model for the response of the seed to the magnetic field generated by the antenna. The fundamental requirement is that the energy stored on capacitor 405 of FIG. 4 after charging is complete be equal to the pacing threshold energy for the tissue surrounding the seed. For example, conventional pacemaker electrodes deliver on the order of four micro-Joules ($E_0$=4 µJ) of energy to pace the tissue each time the heart beats. This number depends upon the tissue type, pulse shape, and electrode geometry, but will be used here as an example. The total energy required to pace N sites is then on the order of N times the threshold energy $E_0$. For example, if ten sites are paced using ten seeds, then the total energy requirement will be on the order of $NE_0$=40 µJ for every heart beat. The energy that must be supplied by the antenna 260 on each heartbeat is this minimum pacing energy times the overall efficiency of coupling energy from the antenna to seeds.

The energy delivered to each seed in a charging time, τ, may be computed for a given set of seed circuit parameters and a measured or computed magnetic field versus time at the site of the seed in question. This is possible because the voltage induced in coil 410 is known to be equal to the time rate of change of magnetic flux linking the coil. The steps needed to compute the energy stored on a given seed capacitor are:

For a given antenna shape, location and orientation, and antenna current waveform, I(t):

1) Compute the magnetic flux linking a seed coil 410 at a given location and a given orientation relative to the antenna, residing in a tissue medium having realistic frequency dependent values of electrical conductivity and permittivity.

2) Compute voltage induced in the coil (and modeled as a voltage in series with the coil 410) as the time rate of change of the flux computed in step 1).

3) With the switch 418 in position 1, use seed circuit equations to compute the charge on capacitor 405 versus time, and therefore the energy stored on the capacitor (equal to square of charge divided by two times the capacitance of 405).

Generally speaking, the magnetic field falls off rapidly as the separation between the seed and the antenna increases. While this may not be true for very large antennas, the body dimensions limit the practical dimensions of the antenna. The exact location (and orientation if the seed does not have a tri-axial coil) of the seed will determine the antenna current magnitude and ON-time required to charge that seed. The seed that links the least magnetic flux from the antenna will then determine these antenna parameters, since all seeds must be capable of acquiring the threshold energy for pacing. We may refer to this seed as the "weakest link", and it alone will be used to compute optimal antenna current waveform and coupling efficiency.

The energy coupling efficiency is defined as the ratio of the total energy delivered to the seed capacitors, $NE_0$, divided by the sum of all energy lost by the antenna during the on-time. Antenna losses that may be included in simulations include:

Energy delivered to all seeds=$NE_0$

Power dissipated (as Ohmic heat) in seed circuit during charging

Power dissipated (as Ohmic heat) in antenna circuit during charging

Power dissipated (as Ohmic heat) by eddy currents induced in conductive body tissues The energy coupling efficiency is then given by $NE_0$ divided by the sum of losses listed above over the duration of the charging time. The Ohmic heat in the antenna circuit is primarily due to $I^2R$ losses in the antenna itself, and hysteresis losses in any magnetic materials that may be included in the antenna design. This statement is also true for Ohmic heating in the seed circuit. Once the parameters of the antenna current waveform needed to charge the weakest link seed to the pacing threshold energy have been determined, these losses may be computed. Once the antenna current waveform parameters have been determined, the electric field, E, generated at any point in the body may be computed. Then, given a knowledge of the electrical conductivity of all body parts affected by the antenna, the current density may be computed at any point in the body as $J=\sigma E$, where $\sigma$ is the electrical conductivity at that point. The Ohmic heating due to eddy currents is then found by integrating the power loss density $J \cdot E = \sigma |E|^2$ over the volume of the patient's body. Since both the magnetic field and the electric field produced by the antenna waveform at any point in space may be derived from the magnetic vector potential, the following further steps may be used to compute coupling efficiency:

4) Compute the vector potential, A, arising from a given current waveform in the seed medium, using realistic tissue conductivity and permittivity.

5) Compute the magnetic field at the site of the seeds as B=curl(A)

6) From 5) determine antenna current waveform parameters needed to charge the weakest link seed to the pacing threshold energy 7) Compute antenna circuit losses for the current waveform found in 6)

8) Compute the sum of all seed circuit losses given a set of seed locations and orientations to the field, and the field computed in 5) using 6)

9) Compute the electric field at points in space as $E=-\partial A/\partial t$

10) Integrate $\sigma |E|^2$ over the patient's body using known or estimated values for the electrical conductivity $\sigma$ at each point in space to determine energy lost to absorption by body tissues 11) Compute efficiency as charging energy delivered to seeds divided by the charging energy plus the losses computed in 7)-10)

Optimization of seed design, antenna design, and antenna circuit waveform is performed by iterating steps 1)-11) to maximize coupling efficiency. The lifetime of the transmitter battery is readily computed from the energy coupling efficiency since on each heart beat the antenna must supply the total pacing energy, $NE_0$ divided by the coupling efficiency. The total energy contained in the battery is its volume times its energy density. The total expected number of heartbeats that the system can pace is then the total battery energy times the energy coupling efficiency divided by the pacing energy per heartbeat, $NE_0$. Making an assumption about the average heart rate, say 72 beats per minute, then yields the battery lifetime in minutes.

In one example calculation a seed contained a coil 3 mm long by 2 mm diameter wound on a core with relative permeability equal to ten. The capacitance was chosen to make the coil resonant at the frequency of the applied magnetic field. A further constraint was made by choosing the Q of the coil (resonant frequency divided by the width of the resonance peak) equal to ten. This constraint of a modest Q provides a margin for possible frequency dispersion by conductive tissues, and a manufacturing margin. Given these assumptions it was found that a magnetic field directed along the axis of the coil must have a magnitude of about 0.001 Tesla (1 mT) to provide the minimum pacing energy of 4 µJ. The antenna model in this calculation was a five inch diameter circular loop of copper having a total weight of 100 grams. The tissue model employed was a combination of heart muscle and blood, having about the same electrical conductivity. When the weakest link seed was placed at a distance of three inches from the plane of the antenna, the following was determined: The optimal energy coupling occurred at a frequency of about 30,000 Hz (30 kHz), where efficiency peaked at about 0.5%, and the lifetime of a 100 gram battery with 720 Joules/gram energy density was about 2 months.

The efficiency can be improved by improving magnetic coupling between the seeds and the antenna. This may be accomplished by using multiple antennas, for example one loop on the ribs over the anterior side of the heart, and one loop on the ribs over the posterior side of the heart. Two or more antenna loops may insure that the weakest link seed is closer to a loop than the three inches used in the example above. An alternative location for an antenna loop may be a loop inserted into the right ventricle of the heart, and attached to a controller placed at the usual pectoral implant location. Such a loop would be located closer to all seeds, particularly since the antenna is energized during systole when the heart is contracted.

Battery lifetime can be extended indefinitely by employing a rechargeable battery. The battery may receive energy for recharging by inductive coupling to antenna 260. External antennae and transmitters for recharging could be located under or around the patient's bed or chair, or be integrated into special clothing. As an alternative to a rechargeable battery, the antenna, transmitter, and battery of FIG. 3 could be integrated into clothing or a disposable patch worn by the patient. ECG signals needed to time the seed pacing could be received via an inductive link from a conventional pacemaker with right atrial and right ventricle leads. In this case, elaborate antenna designs could be incorporated into the special clothing. For example, the antenna could have a portion that surrounds the chest at the latitude of the heart.

Figure 16:
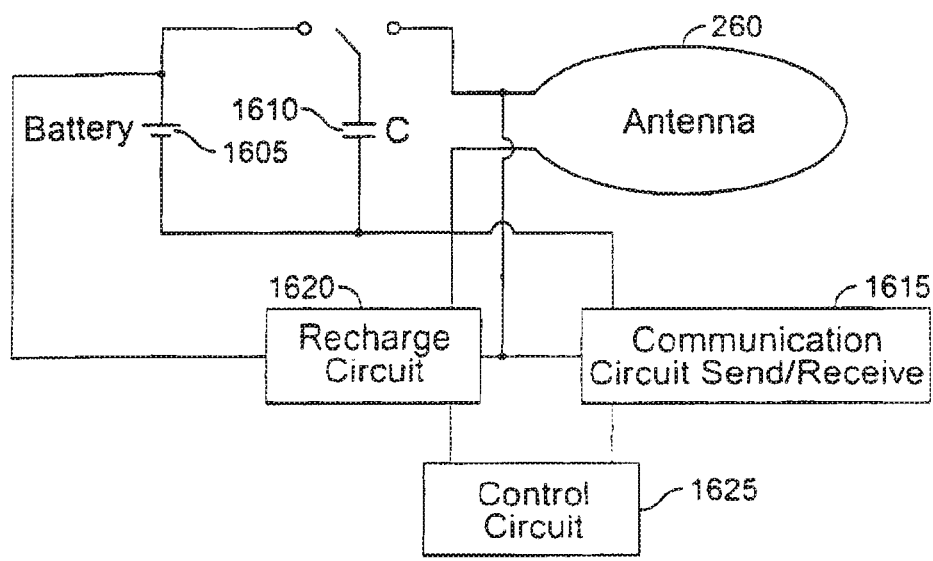
FIG. 16 is a part schematic and part block diagram of a circuit that may be included within embodiments of wireless electrode assemblies to enable them to receive and to transmit information.
Figure 17:
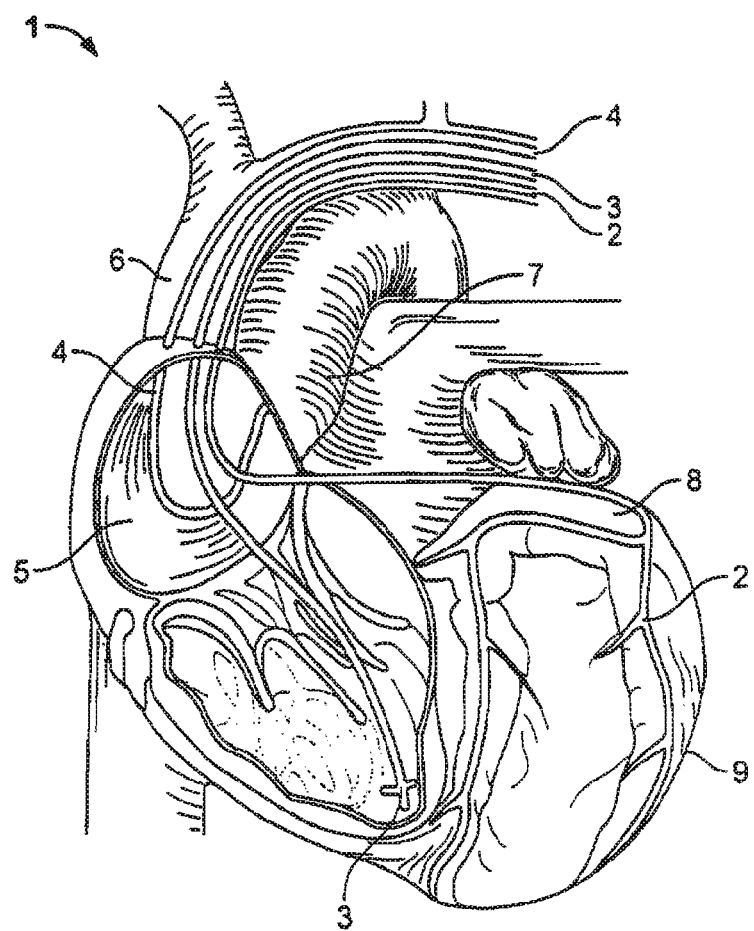
FIG. 17 is an example of a prior art, three-lead pacing system, showing one lead placed in a vein over the left ventricle.

FIG. 16 shows a schematic diagram of an antenna 260 with the charging current waveform being supplied by capacitive discharge through the antenna 260, and capacitor recharge provided by a battery 1605. The value chosen for the capacitor 1610 determines if the current waveform has a single peak or whether the current rings down in a damped sine waveform. Communications electronics 1615 sends pacing discharge signals to the seeds, but may also receive ECG signals from the seeds or a conventional pacemaker. The charge electronics 1620 receives energy via the antenna from an inductive link to an external antenna, to recharge the battery. A control circuit 1625 controls the operation of the recharge circuit 1620 and the communications electronics 1615.

It is also noted that alternative sources of power for the seeds may be used. For example, the mechanical energy of the beating heart is many orders of magnitude larger than the energy required to pace the seeds. At the site of a seed, the heart muscle thickens during systole and thins during diastole as the heart beats. It is estimated that a one mm diameter transducer placed across the heart muscle could generate μJ of energy due to the contraction of the heart, more than ten times the energy needed to pace. A simple mechanical to electrical transducer having nominal efficiency could provide the energy to pace a seed. Other miniature local sources of energy have been suggested in recent literature. These include: piezoelectric and electro-active polymer materials that transduce mechanical to electrical energy; bio-batteries that convert body heat and/or blood flow energy to electrical energy; and tiny amounts of radioactive material that emit short range alpha or beta particles that are readily shielded.

In addition, the seed circuit of FIG. 4 can be simplified by omission of the capacitor and voltage controlled switch. That is, the seed circuit may consist simply of a coil connected across electrodes in contact with tissue. In this case a magnetic field pulse induces a voltage pulse in the seed coil, and the induced voltage directly discharges into tissue. If all seeds are the same, pacing of all seeds is simultaneous. However, the rise time of the induced voltage can be adjusted by adjustment of the coil parameter number of turns, core permeability, and adjustment of a resistor in series with the coil. Thus, a collection of seeds having varying rise times may be used to synchronize the firing sequence of the seeds. The controller may sense a singe local ECG, for example the atrial or right ventricle electrode of a special transmitting seed or of a conventional pacemaker that transmits data to the controller. A burst of current into the antenna would then fire all seeds, with the precise time of firing determined by the electrical properties of each implanted seed.

Figure 18A:
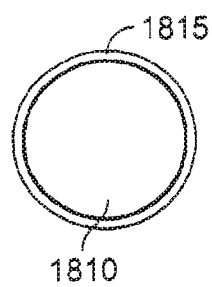
FIGS. 18A to 18C show views of a wireless electrode assembly and a wireless electrode assembly attached to a tissue equivalent circuit.
Figure 18B:
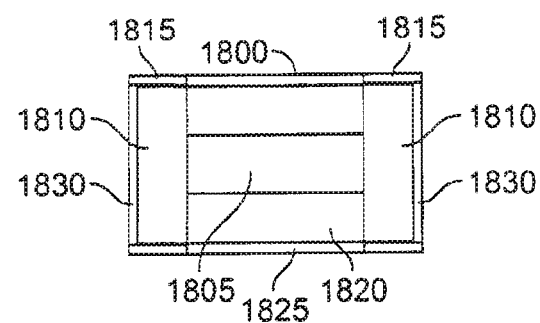
Figure 18C:
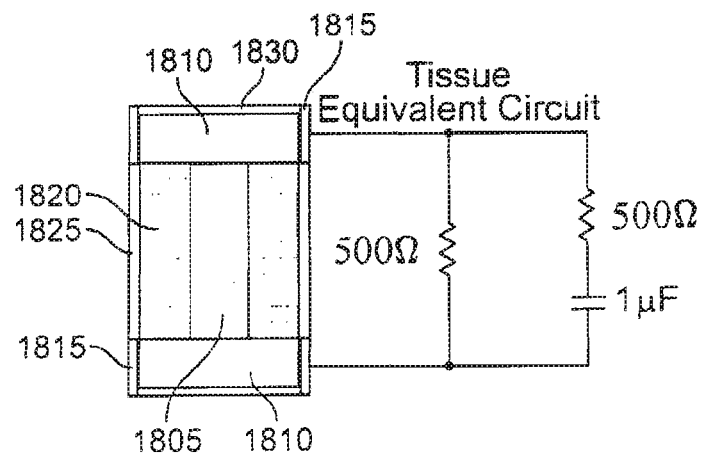

FIGS. 18A-18C show an end view, side view, and side view with equivalent circuit for a simplified seed 1800 for delivering stimulation to tissue, including myocardial tissue on the inside of a heart chamber. As shown, the seed does not have separate energy storage components such as a battery or a capacitor. It instead is comprised of a ferrite core 1805 which may be in the form of a cylinder approximately one mm in diameter and three mm long. At each end of the core 1805 are ferrite caps 1810 which may be in the form of circular disks about 1 mm thick and about 3 mm in diameter. The caps 1810 may be attached to the end of the core 1805, may have central holes through which the core 1805 is received, or may be integrally formed with the core 1805. Ring electrodes 1815 may be formed about the periphery of each cap. The ring electrodes 1815 may be formed of any appropriate materials such as platinum-iridium alloy. The ring electrodes 1815 may be bonded to the caps 1810 using medical grade epoxy, cyanoacrelate, or the like. Other arrangements for the electrodes and other components may also be used, and the particular layout and shape of components that is meant to be illustrative rather than limiting. Because the seed does not have a distinct energy storage device such as a battery or capacitor, it is referred to in this document as a direct activation electrode assembly or device.

The seed 1800 may receive signals using a long loop of wire 1820 wrapped around the core. For example, 99.99% silver wire that is 0.002 inches in diameter and is covered in a polyurethane nylon insulation may be used. The wire 1820 may be wrapped around the core 1805 in any appropriate manner and may comprise, for example, about 900 turns of wire. In general, the voltage induced in the coil is proportional to the number of turns of wire. Wire having a smaller diameter yields more turns when the wire fills the empty volume over the core (nominally 3 mm long gap with 3 mm outside diameter and 1 mm inside diameter). However, smaller diameter wire has a higher electrical resistance, and if the coil resistance becomes comparable to the impedance of the tissue being paced, the net energy delivered to the tissue will diminish. In general the electrical resistance of the wire should not exceed a few hundred Ohms. The measured electrical resistance of the 900 turns of wire 1820 is about 60 Ohms.

The seed 1800 may also be covered as appropriate to protect the materials in the seed 1800 and to insulate them from the tissue and fluids around the seed 1800. For example, a hermetic epoxy layer 1830 may be applied to the ends of both caps 1810, and another hermetic epoxy layer 1825 may be applied around the outside of the coiled wire 1820. In general, the ring electrodes will not be insulated, though they may otherwise be treated, so that they can deliver sufficient energy to the tissue surrounding the seed 1800. The coil 1105E and/or one or more of tines 1110E, and/or the seed distal curved face 1123E may be electrically connected to and part of the distal electrode 1135E. Alternatively, one or more of 1105E, 1110E and 1123E may be used in place of ring 1135E as the distal electrode.

In general, the seed 1800 should be small enough to be delivered easily, such as through a 9 French delivery catheter. Exemplary dimensions of such a seed are 5 mm long and 3 mm in diameter. Also, the seed just described may be incorporated with the delivery and anchoring mechanisms discussed earlier in this document. Typical parameters for the seed 1800 would be a voltage pulse amplitude greater than 0.5 volts (with 2 volts being typical), and a pulse duration of approximately 0.4 msec. In addition, to neutralize charge on the electrodes, the electrical waveform that seed 1800 delivers to the tissue will generally have the pacing pulse described above (with the distal electrode being the cathode) followed by a smaller-amplitude, longer-duration pulse of the opposite polarity so that the integral of the waveform over time will be zero.

Advantageously, the described seed is extremely uncomplicated and is thus capable of delivery one or more specific benefits. First, the simple design allows the seed to take a very small form factor. A small seed can be used with less tissue trauma to a patient, and may also be implanted more easily and at more locations using, for example, percutaneous tranluminal implantation with catheters, as discussed above. This form factor can be reached without extreme engineering for miniaturization, such as would be required for a system using electrical storage devices in the seed.

The simple design is also likely to provide excellent reliability, as there are very few parts to the system, and very little to wear out or otherwise fail. The simple design also contributes to manufacturability, as the seed is fairly simple to make, and thus should be lower in cost and also be manufactured with fewer errors. In addition, the described antenna circuit is small and simple, which may facilitate implantation, lower costs, and improve manufacturability and reliability in similar ways.

The simple seeds also provide operational flexibility. Specifically, the pacing waveform parameters may be adjusted at the antenna circuit without a need to communicate with each of the multiple implanted wireless electrodes. In addition, the seed can provide extremely fast rise times (e.g., an "instant ON" characteristic), which allows possible voltage limiters in the seeds to give all electrodes the same pacing pulse amplitude with nearly the same rise time.

The equivalent circuit attached to seed 1800 in FIG. 18C is designed to represent the features of tissue around the seed 1800. The equivalent circuit comprises two parallel impedances 1830, 1835, with impedance 1830 representing extracelular conductive fluid with a resistor, and impedance 1835 representing muscle cell impedance by cell capacitance in series with a resistor representing intra-cellular fluid. The equivalent circuit is useful in testing candidate wireless electrode or seed designs to determine which will provide the best treatment under particular conditions. The equivalent circuit can also be used after the design phase, during manufacture, to test seeds to ensure that they are working properly. For example, manufactured seeds can be placed in a magnetic field having a waveform substantially identical to that used in the implanted systems, and their reaction may be measured to ensure that they meet manufacturing requirements. In this manner, the equivalent circuit may be particularly useful in two phases of the process-design and manufacture.

The design of the seed can be expressed mathematically by starting with an expression for the voltage induced around the perimeter of an area element whose surface is perpendicular to a time varying magnetic field:

$$V_{ind} = -A(dB/dT) \quad (1)$$

where
$V_{ind}$=induced voltage in volts
A=surface area in m$^2$
B=applied magnetic field in Tesla In Eq. (1), the magnetic field is assumed to be constant in space over the area of the surface. The induced voltage is present throughout space surrounding the source of the magnetic field. A current will flow in a conductive element placed in the time varying magnetic field. For example, the source of the magnetic field may be a current pulse flowing in an antenna, as described above. In a coil aligned with the external magnetic field, the voltage of Eq. (1) is induced in each turn of the coil. If the coil is wound on a magnetically permeable core material, the voltage is further multiplied by the effective permeability of the core. If the coil has multiple layers, the area of Eq. (1) is larger for each successive layer.

Under these observations, the net voltage induced in a coil wound on a permeable core is:

$$V_{ind} = -\beta(dB/dt) \quad (2)$$

where
$\beta = \mu N(\pi/12)(D_i^2 + D_i D_o + D_o^2)$
$\mu$=effective permeability of the core (unitless)
N=the total number of windings on the coil
$D_i$=inside diameter of the coil in meters
$D_o$=outside diameter of the coil in meters If the magnetic field is created by a pulse of current in the antenna, then the time integral of the induced voltage in Eq. (2) is zero, because the field itself is zero at both time zero and after the pulse is delivered. Such a seed thus meets the standard, discussed above, that the integral of the waveform over time is zero.

Considering now the case of a magnetic field generated by a circular loop antenna, the magnetic field at a distance, z, along the axis from the center of a circular loop carrying a current, I, is:

$$B = (\mu_o N_a I/D)[1+(2z/D)^2]^{-3/2} = \gamma I \quad (3)$$

where
$\mu_o$=permeability of free space=$4\pi \times 10^{-7}$ Weber/Amp-m
$N_a$=number of windings on the antenna
D=antenna diameter is meters
z=distance along axis from antenna center in meters
$\gamma = (\mu_o N_a/D)[1+(2z/D)^2]^{-3/2}$ in Tesla/amp The current, I, through the antenna may be made a pulse whose time derivative yields an appropriate pacing waveform when Eq. (3) is inserted into Eq. (2). A relatively simple circuit, like that shown in FIG. 16 can produce an appropriate pulse. In that figure, the capacitor 1610 may be charged to the voltage, V, of the battery 1605. A microprocessor controller, such as control circuit 1625 may be configured to operate the switch near capacitor 1610 and may sense the p-wave in a patient's cardiac ECG. The ECG may be sensed, for example, near the site of the controller implant, or via skin patch electrodes in the case of an external antenna. Alternatively, an implanted sensing lead or wireless electrode may transmit the ECG signal or p-wave trigger to the controller. When the capacitor is switched across the circular loop antenna in FIG. 16, the current flowing in the antenna is given by:

$$I=(CVQ^2/\tau S)[e^{-(1+S)t/(2\tau)} - e^{-(1-S)t/(2\tau)}] \quad (4)$$

where
C=capacitance in farads
V=voltage applied in volts
Q=quality factor (unitless)=$(1/R)(L/C)^{1/2}$
$\tau$=L/R (time constant) in seconds
L=antenna inductance in Henries
R=antenna and capacitor resistance in Ohms
$S=(1-[2Q]^2)^{1/2}$ Combining Eqs. (2)-(4) provides the voltage induced in the wireless electrode coil:

$$V_{ind} = \beta\gamma(CVQ^2/2\tau^2 S)[(1+S)e^{-(1+S)t/(2\tau)} - (1-S)e^{-(1-S)t/(2\tau)}] \quad (5)$$

By evaluating Eq. 5 numerically, one can determine that the waveform is a damped sinusoid when Q>0.5, and is a pulse waveform when Q<0.5. A pulse waveform is appropriate for pacing, and by numerical evaluation of Eq. (5), the pulse has maximum amplitude when Q=0.5. Thus, for this idealized model, antenna components may be selected to achieve Q=0.5, so that Eqs. (4) and (5) become (in the limit of Q→0.5 and S→0):

$$I=(CVt/4\tau^2)e^{-t/2\tau} \quad (6)$$

$$V_{ind} = \beta\gamma(CV/4\tau^2)(1-t/2\tau)e^{-t/2\tau} \quad (7)$$

The waveform of Eq. (7) has a positive pulse with a zero crossing at t=2t, followed by a shallow negative wave that falls exponentially with time. The wave form of Eq. (7) integrates to zero, as is discussed above as being desirable. For a desired pulse width of 0.4 msec, $\tau$ is selected as 0.2 msec. Equation (7) is shown plotted in FIG. 19, with a voltage at time zero taken as 0.23 volts. The solid line in the figure represents computed values, while the triangles represent measure values using a seed like that shown in FIGS. 18A and 18B. Specifically, the measured data was taken with a seed electrode body 5 mm long comprising a coil wound on a ferrite bobbin having core dimension of 1 mm and end flange thickness of 1 mm on each end—the coil of wire being 3 mm long with an inside diameter of 1 mm and an outside diameter of 3 mm, wound on the ferrite bobbin with 900 turns of 0.002 inch insulated silver wire. Using Eq. (2), these parameters produce a value of $\beta=0.003$ m$^2$. The measurements were generated using an antenna having a diameter of seven inches that was constructed from four turns of AWG #8 copper wire.

The wireless electrode was placed at the center of the circular antenna, where the parameters of Eq. (3) yield $\gamma=2.8\times 10^{-5}$ Tesla/amp. The antenna circuit capacitor had C=0.02 Farads, and the applied voltage was V=15 volts. With $\tau$=0.2 msec, the voltage at time zero computed from Eq. (7) and these parameter values is $V_{ind}$=0.16 volts, compared to $V_{ind}$=0.23 volts in the computed plot of FIG. 19.

Further testing was conducted on seeds having end caps of varying thickness, with the coil wound on a 1 mm ferrite core and the gap filled with wound insulated silver wire. The seed with the highest induced voltage had end caps 1 mm thick, with 3 mm of wound wire between them, and a total diameter of 3 mm.

Figure 19:
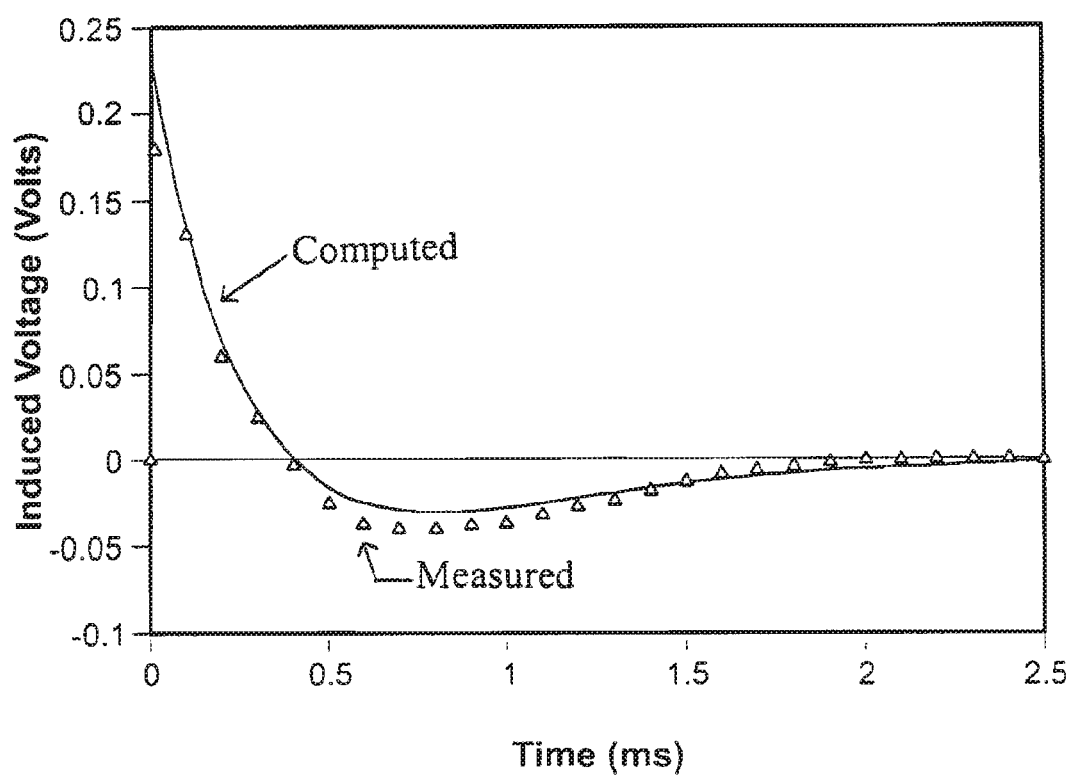
FIG. 19 is a graph of voltage, both computed and measured, induced in a wireless electrode assembly versus time.
Figure 20:
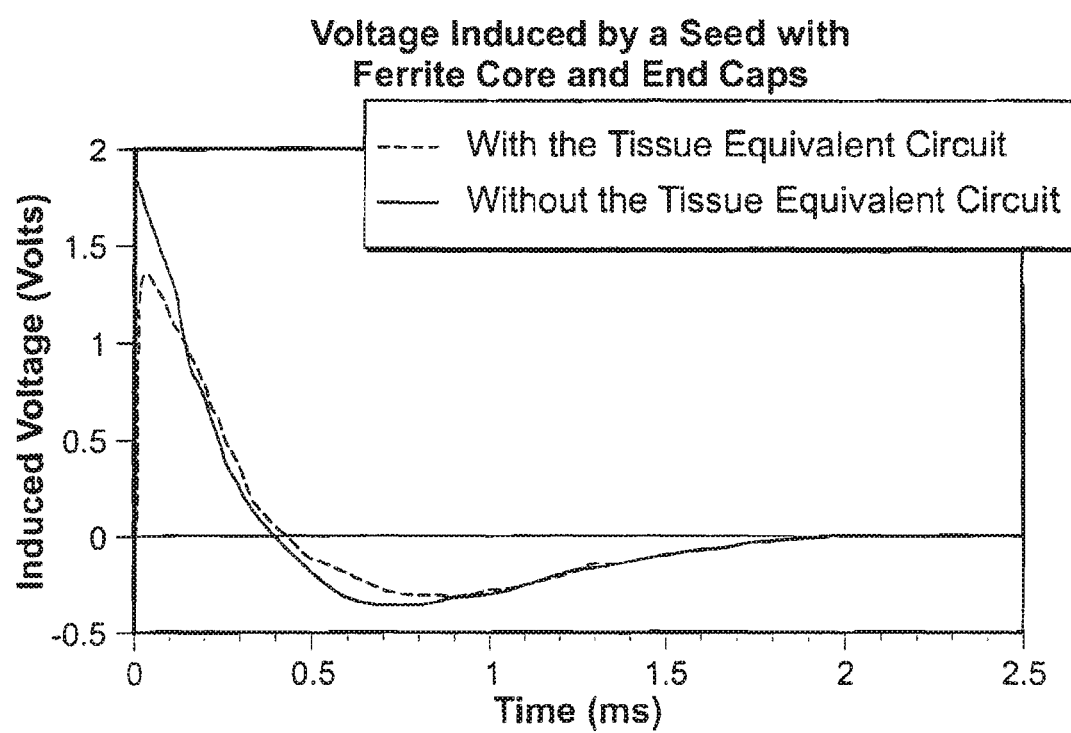
FIG. 20 is a graph of voltage induced in a particular wireless electrode assembly versus time, with and without a tissue equivalent circuit attached across the electrodes.

This seed was tested with and without the equivalent circuit of FIG. 18C attached to the electrodes. FIG. 20 shows a plot of the voltage induced in such a seed when it is placed at the center of the seven inch circular loop antenna discussed above, with voltage V=15 volts and conductance C=0.02 Farads. The figure indicates that the wireless electrodes are not loaded down significantly by the tissue impedance, and pacing voltages larger than one volt are readily attained in the presence of tissue. The waveform of the figure is also appropriate for cardiac pacing using a simple and small wireless electrode and simple antenna circuit. A comparison of FIG. 20 without the equivalent circuit and FIG. 19 shows that the seed has an effective permeability of 1.8/0.18=10 (equal to the ratio of peak induced voltages, since the seeds have the same geometry and number of turns).

A passive voltage limiting element such as a Zener diode may be added to the seed across the stimulation electrodes to control the voltage pulse amplitude. For example, when multiple seeds are located at multiple distances from the antenna, the magnitude of the applied magnetic field will vary from seed to seed according to Eq. (3). The voltage limiting element may help ensure that the pulse amplitude is the same for all seeds and all antenna configurations when the seeds are close enough to the antenna to generate the limit voltage.

A number of embodiments of the invention have been described. Nevertheless, it will be understood that various modifications may be made without departing from the scope of the invention. For example, although the disclosure discusses embodiments in relation to cardiac tissue, the systems and methods described herein are applicable to excitation of other cells, tissues, and organs that may be stimulated to achieve some benefit or result.

In some embodiments, the systems and methods described herein may be used in certain neurological applications. For example, the wireless electrode assemblies and the related systems described herein may be employed to limit pain, control muscle spasms, prevent seizures, treat neurohormonal disorders, and the like.

In other embodiments, the leadless electrode assemblies may be delivered through other conduits other than blood vessels. For example, wireless electrode assemblies described herein may be delivered through the esophagus to the stomach lining or other tissue in the digestive tract. By using the electrode assemblies to electrically stimulation of the stomach tissue or other tissue in the digestive tract, the systems described herein may be used to treat digestive disorders or control hunger sensations.

In certain embodiments, the wireless electrode assemblies described herein may be deployed in the urogenital tract. In such embodiments, organs tissue in the abdominal area may be accessed percutaneously via catheters through the peritoneal space.

Also, the apparatuses, systems, and methods described herein and related to leadless stimulation of tissue may be combined with elements of other types of seeds and/or related apparatuses, systems, and methods. Such elements may be other than those described in this document, such as the seeds, also referred to as microstimulators, and related elements of apparatuses, systems, and methods described in co-pending application Ser. Nos. 10/607,963; 10/609,449; 11/034,190; 11/043,642; 10/607,962; 11/043,404; 10/609,452; 10/609,457; and 10/691,201, each of which is assigned to Advanced Bionics Corporation, and each of which is incorporated herein by reference in its entirety.

For example, the microstimulators described in these applications may be employed as seeds (modified so as to provide an appropriate excitation or stimulation signal), may be provided with the delivery and attachment or anchoring features described herein, and may be implanted using the devices and methods described herein. Alternatively, the apparatuses, systems, and methods related to seeds as described herein may be modified so as to include at least one element of the apparatuses, systems, and methods related to microstimulators described in these incorporated applications. Such at least one element may relate to implantation and/or explantation; fixation and/or anchoring or seeds and/or microstimulators; power transfer and/or data communication between seeds, microstimulators, and other implanted or external power transfer and/or data communications devices; methods of manufacture; electronic circuitry; mechanical packaging of hermetically-sealed seeds and/or microstimulators; materials; and all other elements of apparatuses, systems, and methods described in these incorporated applications.

What is claimed:

1. An implantable leadless cardiac pacing assembly, comprising:
   a body having a proximal end region and a distal end region;
   a first electrode positioned at the distal end region of the body;
   a second electrode spaced proximally away from the first electrode on the body; and
   a plurality of tines arranged radially around the first electrode, wherein each of the plurality of tines assumes a hooked configuration configured to anchor into tissue of a heart wall with the first electrode in contact with the tissue, wherein each of the plurality of tines includes a base, a distal tip and a curved region located between the base and the distal tip in the hooked configuration, wherein the curved region extends distal of the first electrode in the hooked configuration and the distal tip is located proximal of the first electrode in the hooked configuration.

2. The implantable leadless cardiac pacing assembly of claim 1, wherein the curved region extends to a distalmost extent of the implantable leadless cardiac pacing assembly in the hooked configuration.

3. The implantable leadless cardiac pacing assembly of claim 1, wherein the plurality of tines are circumferentially arranged around the distal end region of the body, wherein the plurality of tines are spaced substantially equidistant from one another.

4. The implantable leadless cardiac pacing assembly of claim 1, wherein the distal tip of each of the plurality of tines points toward the body in the hooked configuration.

5. The implantable leadless cardiac pacing assembly of claim 1, wherein the base of each of the tines is attached to a common junction member.

6. The implantable leadless cardiac pacing assembly of claim 1, wherein the body has a cylindrical outer surface.

7. The implantable leadless cardiac pacing assembly of claim 6, wherein the curved region of each of the tines extends radially outward of the cylindrical outer surface of the body in the hooked configuration.

8. The implantable leadless cardiac pacing assembly of claim 6, wherein the second electrode extends around the cylindrical outer surface.

9. The implantable leadless cardiac pacing assembly of claim 1, wherein the base of each of the tines is moveable relative to the body.

10. An implantable leadless cardiac pacing assembly, comprising:
a body having a proximal end region and a distal end region;
a power source contained within the body, the power source configured to be entirely implanted within a target region of a heart with the body;
a first electrode disposed at a distal end of the body and extending distally therefrom; and
a plurality of tines equidistantly spaced around the distal end region of the body, wherein each of the plurality of tines is in a hooked configuration in an equilibrium state;
wherein a distalmost extent of each of the plurality of tines is located distal of the first electrode in the hooked configuration; and
wherein a tip of each of the plurality of tines is located proximal of the distalmost extent of each of the plurality of tines in the hooked configuration.

11. The implantable leadless cardiac pacing assembly of claim 10, wherein each of the plurality of tines includes a base at an end opposite from the tip, wherein the base of each of the plurality of tines is attached to a common junction member.

12. The implantable leadless cardiac pacing assembly of claim 10, wherein each of the plurality of tines extends radially outward beyond the body in the hooked configuration.

13. The implantable leadless cardiac pacing assembly of claim 12, wherein the distal tip of each of the plurality of tines points toward the body in the hooked configuration.

14. The implantable leadless cardiac pacing assembly of claim 10, wherein each of the plurality of tines extends in a longitudinal orientation when deflected into a delivery configuration.

15. The implantable leadless cardiac pacing assembly of claim 14, wherein the distal tip of each of the plurality of tines points toward a target tissue implantation site when in the delivery configuration.

16. An implantable leadless cardiac pacing assembly, comprising:
a cylindrical body having a proximal end region and a distal end region;
a power source contained within the body, the power source configured to be entirely implanted within a target region of a heart with the body;
a first electrode positioned at a distal end of the body and extending distally therefrom;
a second electrode spaced proximally away from the first electrode on the body; and
a plurality of tines equidistantly spaced around the distal end region;
wherein each of the plurality of tines includes a proximal base, a distal tip, and an intermediate region between the proximal base and the distal tip;
wherein the proximal base of each of the plurality of tines is attached to a common junction member;
wherein each of the plurality of tines is biased to have a hooked configuration when unconstrained; and
wherein the distal tip of each of the plurality of tines is located proximal of the intermediate region in the hooked configuration.

17. The implantable leadless cardiac pacing assembly of claim 16, wherein each of the plurality of tines extends radially outward beyond the body in the hooked configuration.

18. The implantable leadless cardiac pacing assembly of claim 16, wherein the distal tip of each of the plurality of tines points toward the body in the hooked configuration.

19. The implantable leadless cardiac pacing assembly of claim 16, wherein the plurality of tines are arranged circumferentially around the first electrode.

20. The implantable leadless cardiac pacing assembly of claim 16, wherein the proximal base of each of the tines is moveable relative to the body.

* * * * *